US009365655B2

(12) United States Patent
Craig et al.

(10) Patent No.: US 9,365,655 B2
(45) Date of Patent: Jun. 14, 2016

(54) SOLUBLE HEAVY-CHAIN ONLY ANTIBODIES

(71) Applicants: Roger Kingdon Craig, Cheshire (GB); Franklin Gerardus Grosveld, Rotterdam (NL); Richard Wilhelm Janssens, Rotterdam (NL); Dubravka Drabek, Rotterdam (NL); Tao Chen, Rotterdam (NL); Ernie De Boer, Rotterdam (NL)

(72) Inventors: Roger Kingdon Craig, Cheshire (GB); Franklin Gerardus Grosveld, Rotterdam (NL); Richard Wilhelm Janssens, Rotterdam (NL); Dubravka Drabek, Rotterdam (NL); Tao Chen, Rotterdam (NL); Ernie De Boer, Rotterdam (NL)

(73) Assignee: Erasmus University Medical Center, Rotterdam (NL)

( * ) Notice: Subject to any disclaimer, the term of this patent is extended or adjusted under 35 U.S.C. 154(b) by 111 days.

(21) Appl. No.: 13/815,812

(22) Filed: Mar. 15, 2013

(65) Prior Publication Data

US 2013/0323235 A1 Dec. 5, 2013

Related U.S. Application Data

(63) Continuation of application No. 13/259,472, filed as application No. PCT/GB2010/000500 on Mar. 19, 2010, now Pat. No. 8,883,150.

(30) Foreign Application Priority Data

Mar. 24, 2009 (GB) ................. 0905023.8

(51) Int. Cl.
| | |
|---|---|
| A01K 67/00 | (2006.01) |
| C07K 16/46 | (2006.01) |
| C07K 16/00 | (2006.01) |
| C07K 16/10 | (2006.01) |
| C07K 16/12 | (2006.01) |
| C07K 16/28 | (2006.01) |
| C12N 15/85 | (2006.01) |

(52) U.S. Cl.
CPC ............... *C07K 16/46* (2013.01); *C07K 16/00* (2013.01); *C07K 16/1018* (2013.01); *C07K 16/1271* (2013.01); *C07K 16/2896* (2013.01); *C12N 15/8509* (2013.01); *A01K 2267/01* (2013.01); *C07K 2317/21* (2013.01); *C07K 2317/22* (2013.01); *C07K 2317/24* (2013.01); *C07K 2317/565* (2013.01); *C07K 2317/567* (2013.01); *C07K 2317/569* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,591,669 A | 1/1997 | Krimpenfort et al. | |
| 5,843,440 A | 12/1998 | Pouletty et al. | |
| 5,877,397 A | 3/1999 | Lonberg et al. | |
| 6,150,584 A | 11/2000 | Kucherlapati et al. | |
| 6,162,963 A | 12/2000 | Kucherlapati et al. | |
| 7,731,969 B1 | 6/2010 | Tucker et al. | |
| 7,785,903 B2 | 8/2010 | Bond et al. | |
| 2003/0022240 A1* | 1/2003 | Luo .................. | C07K 16/00 435/7.1 |
| 2006/0246477 A1 | 11/2006 | Hermans et al. | |
| 2007/0292936 A1 | 12/2007 | Barthelemy | |

FOREIGN PATENT DOCUMENTS

| | | | | |
|---|---|---|---|---|
| EP | 0368684 B2 | 3/1994 | | |
| EP | 1399559 B1 | 3/2004 | | |
| NL | WO 2006008548 A2 * | 1/2006 | ............. | C07K 16/00 |
| NL | WO 2008035216 A2 * | 3/2008 | ............. | C07K 16/00 |
| RU | 2335507 C2 | 10/2008 | | |
| WO | WO94/04678 | 3/1994 | | |
| WO | 02066630 A1 | 8/2002 | | |
| WO | WO-02/085944 A2 | 10/2002 | | |
| WO | WO 02/100348 A2 | 12/2002 | | |
| WO | WO-03/035694 A2 | 5/2003 | | |
| WO | WO-2004/049794 A2 | 6/2004 | | |
| WO | WO-2004/076677 A2 | 9/2004 | | |
| WO | WO-2006/008548 A2 | 1/2006 | | |
| WO | WO 2006008548 A2 * | 1/2006 | | |
| WO | WO 2006122825 A2 * | 11/2006 | | |
| WO | 2007096779 A2 | 8/2007 | | |
| WO | WO-2007/096779 A2 | 8/2007 | | |
| WO | WO-2008/035216 A2 | 3/2008 | | |
| WO | WO 2008035216 A2 * | 3/2008 | | |
| WO | WO-2008/151081 A1 | 12/2008 | | |
| WO | 2009013620 A2 | 1/2009 | | |
| WO | WO2011/072204 A1 | 6/2011 | | |

(Continued)

OTHER PUBLICATIONS

Watson et al., Recombinant DNA, 2nd edition, Scientifican American Books, 1992, chapter 14 "The Introduction of Foreign Genes into Mice" pp. 255-272.*

(Continued)

*Primary Examiner* — Michael Szperka
(74) *Attorney, Agent, or Firm* — Saul Ewing LLP

(57) ABSTRACT

The present invention provides a high affinity, antigen-specific, soluble heavy chain-only antibody which: lacks hallmark camelid-related amino acid substitutions and has FR2 substitutions which are not found in antibodies which comprise heavy and light chain; shows increased net hydrophobicity within CDR1 and an increased number of charged amino acids present in CDR3; and comprises one or more amino acid substitutions within the framework β-pleated sheet leading to increased net hydrophobicity within FR1 and increased number of charged amino acids present in FR3. Also provided are VH domains having the same properties, gene segments for their production, methods for their production, transgenic animals and uses of the antibody of the VH domains in therapy.

8 Claims, 30 Drawing Sheets

(56) References Cited

FOREIGN PATENT DOCUMENTS

| WO | WO2012/122512 A1 | 9/2012 |
| WO | WO2012/141798 A1 | 10/2012 |

OTHER PUBLICATIONS

Anderson, S.M. et al., "New markers for murine memory B cells that define mutated and unmutated subsets," J. Exp. Med., vol. 204, No. 9, pp. 2103-2114, 2007.

Barthelemy, P.A. et al., "Comprehensive Analysis of the Factors Contributing to the Stability and Solubility of Autonomous Human VH Domains," J. Biol. Chem., vol. 283, pp. 3639-3654, 2008.

Bernasconi, N.L. et al., "Maintenance of Serological Memory by Polyclonal Activation of Human Memory B Cells," Science, vol. 298, No. 5601, pp. 2199-2202, 2002.

Boersma, W.J.A. et al., "Summary of workshop findings for porcine B-cell markers," Veterinary Immunology and Immunopathology, vol. 80, Nos. 1-2, pp. 63-78, 2001.

Bond, C.J. et al., "Contributions of CDR3 to VHH domain stability and the design of monobody scaffolds for naive antibody libraries," J. Mol. Biol., vol. 332, No. 3, pp. 643-655, 2003.

Bruggemann, M. et al., "Heavy-chain-only antibody expression and B-cell development in the mouse," Critical Reviews in Immunology, vol. 26, No. 5, pp. 377-390, 2006.

Colbere-Garapin, F. et al., "A new dominant hybrid selective marker for higher eukaryotic cells," J. Mol. Biol., vol. 150, pp. 1-14, 1981.

Crotty, S. et al., "Cutting Edge: Long-Term B Cell Memory in Humans after Smallpox Vaccination," J. Immunology, vol. 171, pp. 4969-4973, 2003.

Denham, S. et al., "Monoclonal antibodies putatively identifying porcine B cells," Veterinary Immunology and Immunopathology, vol. 60, Nos. 3-4, pp. 317-328, 1998.

Dolk, E. et al., "Isolation of Llama Antibody Fragments for Prevention of Dandruff by Phage Display in Shampoo," Applied Environmental Microbiology, vol. 71, No. 1, pp. 442-450, 2005.

Dumoulin, M. et al., Single-domain antibody fragments with high conformational stability:, Protein Science, vol. 11, No. 3, pp. 500-515, 2002.

Ellyard, J.I. et al., "Antigen-selected, immunoglobulin-secreting cells persist in human spleen and bone marrow," Blood, vol. 103, No. 10, pp. 3805-3812, 2004.

Ewert, S. et al., "Biophysical Properties of Camelid VHH Domains Compared to Those of Human VH3 Domains," Biochemistry, vol. 41, No. 11, pp. 3628-3636, 2002.

Fahrner, R.L. et al., Industrial purification of pharmaceutical anitbodies: development, operation, and validation of chromatography processes:, Biotechnol. Gen. Eng. Rev., vol. 18, pp. 301-327, 2001.

Geraldes, P. et al., "Immunoglobulin heavy chain and the life of memory B cells," FASEB Journal, vol. 19, No. 4, Suppl. S. Part 1., pp. A21-A22, 2005.

Geraldes, P. et al., "Ig heavy chain promotes mature B cell survival in the absence of light chain," Journal of Immunology, vol. 179, No. 3, pp. 1659-1668, 2007.

Hamers-Casterman, C. et al., "Naturally occurring antibodies devoid of light chains," Nature, vol. 363, No. 6428, pp. 446-448, 1993.

Hartman, S.C. et al., "Two dominant-acting selectable markers for gene transfer studies in mammalian cells," Proc. Natl. Acad. Sci. USA, vol. 85, No. 21, pp. 8047-8051, 1988.

Heinrich, G. et al., Characterization of a human T cell specific chimeric antibody (CD7) with human constant and mouse variable regions, J. Immunol.,, vol. 143, No. 11, pp. 3589-3597, 1989.

Janeway, C.A. et al., "The Development of B Lymphocytes," Immunobiology, 3rd Edition, Garland Publishing Inc., pp. 5:1-5:33 and 8:1-8:17, 1997.

Janssens, R. et al., "Generation of heavy-chain-only antibodies in mice," Proc. Natl. Acad. Sci. USA, vol. 103, No. 41, pp. 151_Jkan30-15135, 2006.

Jaton, J.C. et al., "Recovery of Antibody Activity upon Reoxidation of Completely Reduced Polyalanyl Heavy Chain and Its Fd Fragment Derived from Anti-2,4-dinitrophenyl Antibody," Biochemistry, vol. 7, No. 12, pp. 4185-4195, Dec. 1968.

Kandavelou, K. et al., "Targeted manipulation of mammalian genomes using designed zinc finger nucleases," Biochem. Biophys. Res. Commun., vol. 388, No. 1, pp. 56-61, 2009.

Kim, C.W. et al., "Members of the syndecan family of heparan sulfate proteoglycans are expressed in distinct cell-, tissue-, and development-specific patterns," Mol. Biol. Cell., vol. 5, No. 7, pp. 797-805, 1994.

Kitamura, D., and Rajewsky, K., "Targeted disruption of mu chain membrane exon causes loss of heavy-chain allelic exclusion," Nature, vol. 356, No. 6365, pp. 154-156, 1992.

Klein, U. et al., Human immunoglobulin (Ig)M+IgD+ peripheral blood B-cells expressing the CD27 cell surface antigen carry somatically mutated variable region genes: CD27 as a general markerfor somatically mutated (memory) B Cells, J. Exp. Med., vol. 188, No. 9, pp. 1679-1689, 1998.

Kokubu, F. et al., "Diverse Organization of Immunoglobulin VH-Gene Loci in a Primitive Vertebrate," Embo J., vol. 7, No. 11, pp. 3413-3422, 1988.

Maruyama, M. et al., "Memory B-cell persistence is independent of persisting immunizing antigen," Nature, vol. 407, No. 6804, pp. 636-642, 2000.

Meijer, P.J. et al., "Human Antibody Repertoires," Therapeutic Antibodies: Methods and Protocols, vol. 525, pp. 261-277, 2009.

Morrison, S.L. et al., "Chimeric human antibody molecules: Mouse antigen-binding domains with human constant region domains," Proc. Natl. Acad. Sci. USA, vol. 81, pp. 6851-6855, Nov. 1984.

Naessens, J., "Surface Ig on B lymphocytes from cattle and sheep." Int. Immunol., vol. 9, No. 3, pp. 349-354, 1997.

Neuberger, M.S. et al., "A hapten-specific chimaeric IgE antibody with Human physiological effector function," Nature, vol. 314. No. 6008, pp. 268-270, 1985.

Neuberger, M.S. et al., "Construction of novel antibodies by use of DNA transfection: design of plasmid vectors" Phil Trans. R Soc. Lond., vol. 317, No. 1540, pp. 425-432, 1986.

Nguyen, V.K. et al., "Heavy-chain only antibodies derived from dromedary are secreted and displayed by mouse B cells," Immunology, vol. 109, No. 1, pp. 93-101, 2003.

Radbruch, A. et al., "Competence and competition: the challenge of becoming a long-lived plasma cell," Nature Reviews Immunology, vol. 6, No. 10, pp. 741-750, 2006.

Remy, S. et al., "Zinc-finger nucleases: a powerful tool for genetic engineering of animals," Transgenic Res., vol. 19, No. 3, pp. 363-371, 2010, (Sep. 26, 2009 [Epub ahead of print]).

Riechmann, L., "Rearrangement of the Former VL Interface in the Solution Structure of a Camelised, Single Antibody VH Domain," J. Mol. Biol., vol. 259, No. 5, pp. 957-969, 1996.

Riechmann, L. et al., "Single domain antibodies: comparison of camel VH and camelised human VH domains," J. Immunol. Methods, vol. 231, Nos. 1-2, pp. 25-38, 1999.

Rosenberg, A.S., "Effects of protein aggregates: an immunologic perspective," The AAPS Journal, vol. 8, No. 3, Article 59, pp. E501-E507, 2006.

Sakurai, K. et al., "Efficient integration of transgenes into a defined locus in human embryonic stem cells," Nucleic Acids Res., vol. 38, No. 7, e96., [Epub Jan. 13, 2010].

Sanderson, R.D. et al., "B lymphocytes express and lose syndecan at specific stages of differentiation," Cell Regulation, vol. 1, No. 1, pp. 27-35, 1989.

Santerre, R.F. et al., "Expression of Prokaryotic Genes for Hygromycin B and G418 Resistance as Dominant-Selection Markers in Mouse L Cells," Gene, vol. 30, Nos. 1-3, pp. 147-156, 1984.

Scheid, J.F. et al., "Broad Diversity of Neutralizing Antibodies Isolated from Memory B Cells in HIV-Infected Individuals," Nature, vol. 458, No. 7238, pp. 636-640, 2009.

Sehgal, D. et al., "Distinct clonal Ig diversification patterns in young appendix compared to antigen-specific clones," J. Immunol., vol. 168, No. 11, pp. 5424-5433, 2002.

Singh, N. et al., "Biallelic germline transcription at the kappa immunoglobulin locus," J Exp. Med., vol. 197, No. 6, pp. 743-750, 2003.

(56) References Cited

OTHER PUBLICATIONS

Sitia, R. et al., "Developmental Regulation of IgM Secretion: The Role of the Carboxy-Terminal Cysteine," Cell, vol. 60, pp. 781-790, 1990.
Slifka, M.K. et al., "Humoral immunity due to long-lived plasma cells," Immunity, vol. 8, No. 3, pp. 363-372, 1998.
Smith, B. et al., Prolonged in Vivo Residence Times of antibody Fragments Associated with Albumin:, Bioconjugate Chem., vol. 12, pp. 750-756, 2001.
Sun, L.K. et al., "Chimeric antibody with human constant regions and mouse variable regions directed against carcinoma-associated antigen 17-1A," Proc. Natl. Acad. Sci. USA, vol. 84, (No. 1), pp. 214-218, Jan. 1987.
Tangye, S.G. and Tarlinton, D.M., "Memory B cells: effectors of long-lived immune responses," Eur. J. Immunol., vol. 39, No. 8, pp. 2065-2075, 2009.
Tanha, J. et al., "Optimal design features of camelized human single-domain antibody libraries," J. Biol. Chem., vol. 276, pp. 24774-24780, 2001.
Vara, J.A. et al., "Expression in Mammalian Cells of a Gene from *Streptomyces alboniger* Conferring Puromycin Resistance," Nucleic Acids Research, vol. 14, No. 11, pp. 4617-4624, 1986.
Ward, E.S. et al., "Binding Activities of a Repertoire of Single Immunoglobulin Variable Domains Secreted from *Escherichia coli*," Nature, vol. 341, pp. 544-546, 1989.
Worn, A., and Pluckthun, A., "Different equilibrium stability behavior of ScFv fragments: identification, classification, and improvement by protein engineering," Biochemistry, vol. 38, No. 27, pp. 8739-8750, 1999.
Wrammert, J. et al., "Rapid Cloning of High-Affinity Human Monoclonal Antibodies Against Influenza Virus," Nature, vol. 453, No. 7195, pp. 667-672, 2008.
Xu, J.L., and Davis, M.M., "Diversity in the CDR3 region of V(H) is sufficient for most antibody specificities," Immunity, vol. 13, pp. 37-45, 2000.
Zou, X. et al., "Dominant Expression of a 1.3 Mb Human IgK Locus Replacing Mouse Light Chain Production," The FASEB J., vol. 10, No. 10, pp. 1227-1232, 1996.
Zou, X. et al., "Expression of a Dromedary Heavy Chain-Only Antibody and B Cell Development in the Mouse," J. Immunology, vol. 175, pp. 3769-3779, 2005.
Zou, X. et al., "Heavy chain—only antibodies are spontaneously produced in light chain—deficient mice," J. Exp. Med., vol. 204, No. 13, pp. 3271-3283, 2007.
International Search Report based on International Application No. PCT/GB2010/000500 dated Dec. 21, 2010.
Co-pending U.S. Appl. No. 13/259,472, filed Feb. 22, 2012.
U.S. Appl. No. 11/658,361, filed Oct. 10, 2008, now abandoned.
Co-pending U.S. Appl. No. 12/645,653, filed Dec. 23, 2009.
Co-pending U.S. Appl. No. 12/645,684, filed Dec. 23, 2009.
Co-pending U.S. Appl. No. 13/013,156, filed Jan. 25, 2011.
Co-pending U.S. Appl. No. 13/837,520, filed Mar. 15, 2013.
Co-pending U.S. Appl. No. 13/837,402, filed Mar. 15, 2013.
EP Communication dated Feb. 27, 2014 regarding European Patent Application No. 10179784.3.
"Shin-Seikagaku Jikken Kouza 12, Bunshi-Men'ekigaku III—Kougen, Koutai, Hotai-" (New Biochemical Experimental Seminar 12, Molecular Immnology III—antigen, antibody, and complement-) 1992, K.K. Tokyo Kagaku Dojin, pp. 1-11, English Translation Excerpts.
Japanese Patent Office Inquiry dispatched on Mar. 11, 2014. English translation.
Crescendo Biologics, "Crescendo Biologics Announces the Crescendo Mouse," 2013, retrieved from the Internet, URL: http://www.crescendobiologics.com/dev/uploads/Downloads/160113 Crescendo Mouse Press Release.pdf, retrieved on Jul. 30, 2014.
Pharma Focus Asia, "VelocImmune—A novel platform," 2009, retrieved from the Internet, URL: http://www.pharmafocusasia.com/clinical_trials/human_antibody_discovery.htm, retrieved on Jul. 30, 2014.
Inquiry by Japanese Patent Office dated Jun. 24, 2014, regarding Russian Patent Application No. 2011/166561, filed on Jul. 29, 2011.
Kriangkum, J. et al., "Bispecific and bifunctional single chain recombinant antibodies," Biomolecular Engineering, vol. 18, pp. 31-40 (2001).
Brorson, K. et al., "Mutational Analysis of Avidity and Fine Specificity of Anti-Levan Antibodies," J. Immunol., vol. 163, pp. 6694-6701 (1999).
Brummell, D.A. et al., "Probing the Combining site of an anti-carbohydrate antibody by saturation-Mutagenesis: role of the heavy-chain CDR3 residues."
Burks, E. et al., "In vitro scanning saturation mutagenesis of an antibody binding pocket," PNAS, vol. 94, pp. 412-417 (1997).
Colman, P.M. et al., "Effects of amino acid sequence changes on antibody-antigen interactions," Research in Immunol., vol. 145, pp. 33-36 (1994).
Jang, Y.J. et al., "The structural basis for DNA binding by an anti-DNA autoantibody," Molec. Immunol., vol. 35, pp. 1207-1217 (1997).
Kobayashi, H. et al., "Tryptophan H33 plays an important role in pyrimidine (6-4) pyrimidine photoproduct binding by a high-affinity antibody," Protein Engineering, vol. 12, pp. 879-844 (1999).
Kumar, S. et al., "Molecular Cloning and Expression of the Fabs of Human Autoantibodies in *Escherichia coli*," J. Biol. Chem., vol. 275, pp. 35139-35136 (2000).
Smith-Gill, S. et al., "Contributions of Immunoglobulin Heavy and Light Chains to Antibody Specificity for Lysozyme and Two Haptens," J. Immunol., vol. 139, pp. 4135-4144 (1987).
Song, M.K. et al., "Light Chain of Natural Antibody Plays a Dominant Role in Protein Antigen Binding," Biochem. Biophys. Res. Comm., vol. 268, pp. 390-394 (2000).
Decision of Grant by Russian Patent Office dated May 21, 2014, regarding Russian Patent Application No. 2011/142759, filed on Mar. 19, 2010.
Lefranc et al., Immunoglobulin Facts Book, Academic Press, pp. 3-44, 97-428, 2001.
Murphy, A., "VelocImmune: Immunoglobulin Variable Region Humanized Mice," in M. Little (ed.), Recombinant Antibodies for Immunotherapy, pp. 100-107, Cambridge University Press, New York, NY, 2009.
Tanha, et al., Selection by phage display of llama conventional VH fragments with heavy chain antibody VHH properties, Recombinant Technology, Journal of Immunological Methods, 2002, pp. 97-109, vol. 263, Published by Elsevier Science B.V.
Babcock, John S. et al., A novel strategy for generating monoclonal antibodies from single, isolated lymphocytes producing antibodies of defined specificities (PCR/antibody-forming cells/VH and VL genes/immunoglobulin/plaque assays), Proceedings of the National Academy of Science, Jul. 1996, pp. 7843-7848, vol. 93, Immunology, USA.
Coronella, J. A. et al., Amplification of IgG VH and VL (Fab) from single human plasma cells and B cells, Nucleic Acids Research, 2000, pp. 1-7, vol. 28, No. 20 e85, Oxford University Press.
Ja'Kemp, Third Party Observations, The European Patent Office, Munich, Germany, Jul. 1, 2015, pp. 1-5.
Janeway-Travers, Immunobiology the Immune System in Health and Disease, 1st Edition, 1994, 11 pp., (selected excerpts).
Wols, Heather A. Minges, Plasma Cells, Encyclopedia of Life Sciences, 2005, pp. 1-8, John Wiley & Sons, Ltd., USA.

* cited by examiner

Figure 3

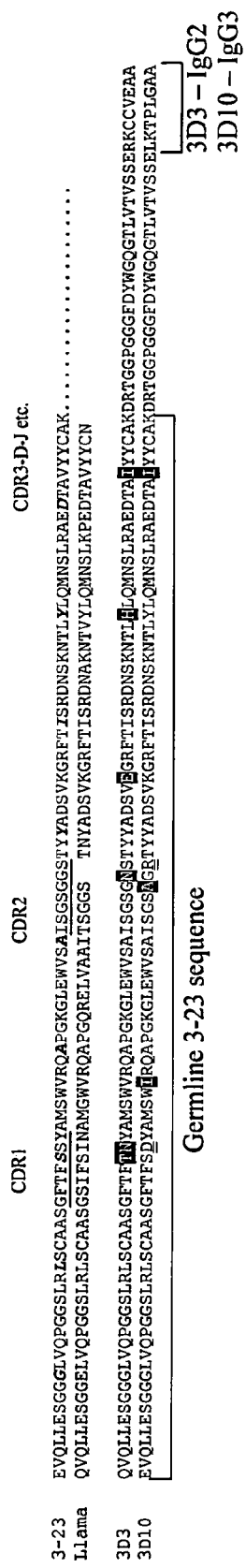

Figure 4

```
              CDR1                          CDR2                                                CDR3-D-J etc.
3-23    EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAK..........
Llama   QVQLLESGGGELVQPGGSLRLSCAASGSIFSINAMGWVRQAPGQRELVAAITSGGS    TNYADSVKGRFTISRDNAKNTVYLQMNSLKPEDTAVYYCN 3D3     QVQLLESGGGLVQPGGSLRLSCAASGFTFTNYAMSWVRQAPGKGLEWVSAISGSGNSTYYADSVEGRFTISRDNSKNTIHLQMNSLRAEDTAIYYCAKDRTGPGGGEDYWGQGTLVTVSSERKCCVEAA
3D10    EVQLLESGGGLVQPGGSLRLSCAASGFTFSDYAMSWIRQAPGKGLEWVSAISGSAGRTYYADSVKGRFTISRDNSKNTLYLQMNSLRAEDTAIYYCAKDRTGPGGGFDYWGQGTLVTVSSELKTPIGAA
                           Germline 3-23 sequence                                                                        3D3 – IgG2
                                                                                                                          3D10 – IgG3
```

The first two amino acids of 3D3 are to be ignored. Changes are likely due to degenerate primer.
Amino acids highlighted in black are mutations different from 3-23 or between clones.
Bold italicised amino acids are every 10 amino acids.
Double underlined residues are differences between clones with the same VDJ rearrangement.
Single underlined CDR1, CDR2 and CDR3 etc.

Figure 5

```
Degen. Primer              CDR-1                    CDR-2                                                      DJ loop                              hinge
                          -------                  -------                                                    -------                              -----
3.23---EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYC----------------------------WYRGEGTLVTVSSELKTPLG
```

(multiple sequence alignment of antibody variable regions follows, grouped into phage display (upper bracket) and hybridomas (lower bracket) sets)

Double underlined: mutations caused by the use of a degenerate primer
Highlighted in black: mutations
Groupings: different VDJ rearrangements
Italicised (bottom group): IgG2, while the rest is IgG3

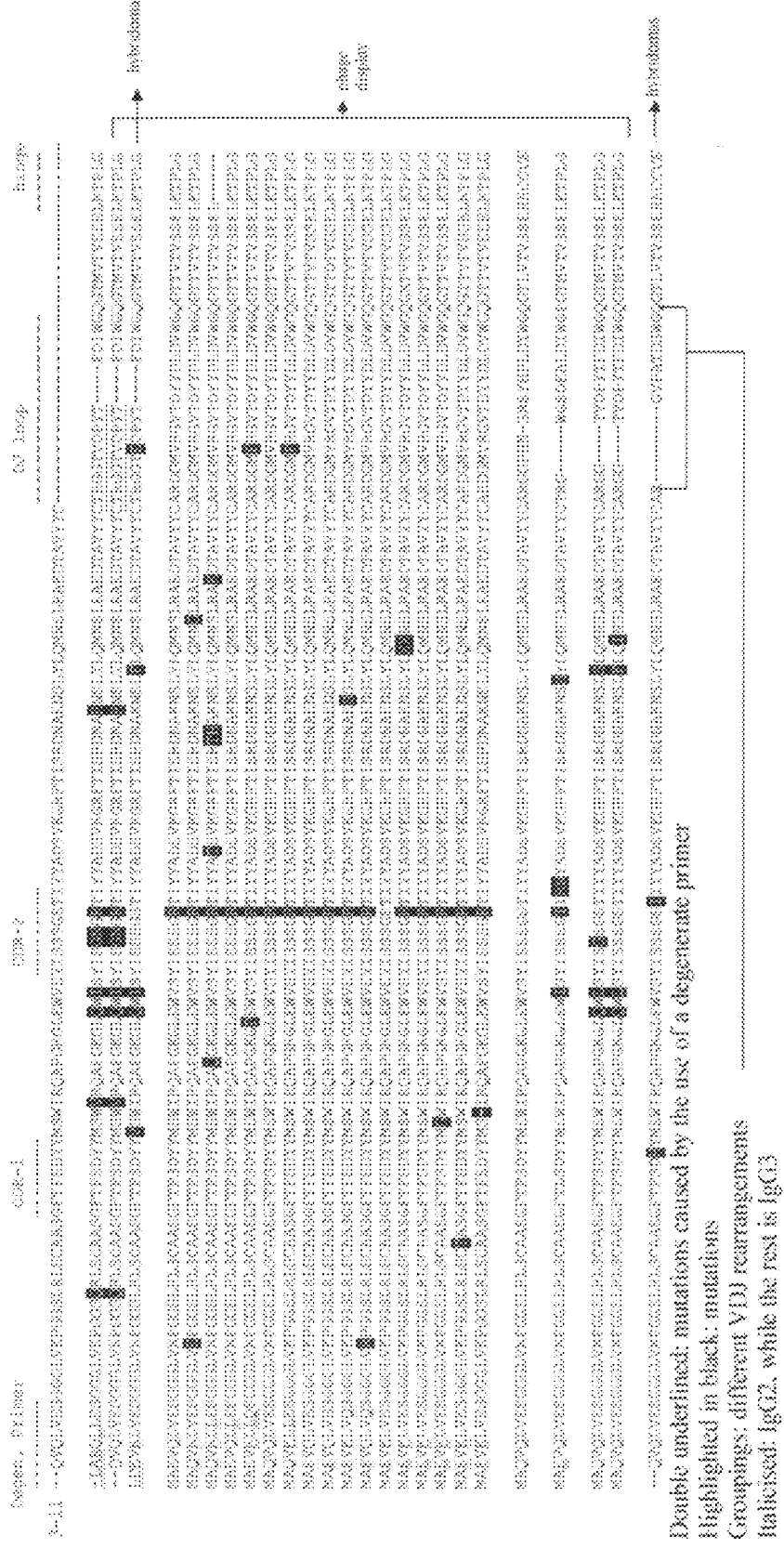

Figure 10

Solubility of αCR1 VH domains

A1   4.6 mg/ml
A9   11.5 mg/ml
B1   5.1 mg/ml
E1   5.3 mg/ml
G11  5.8 mg/ml

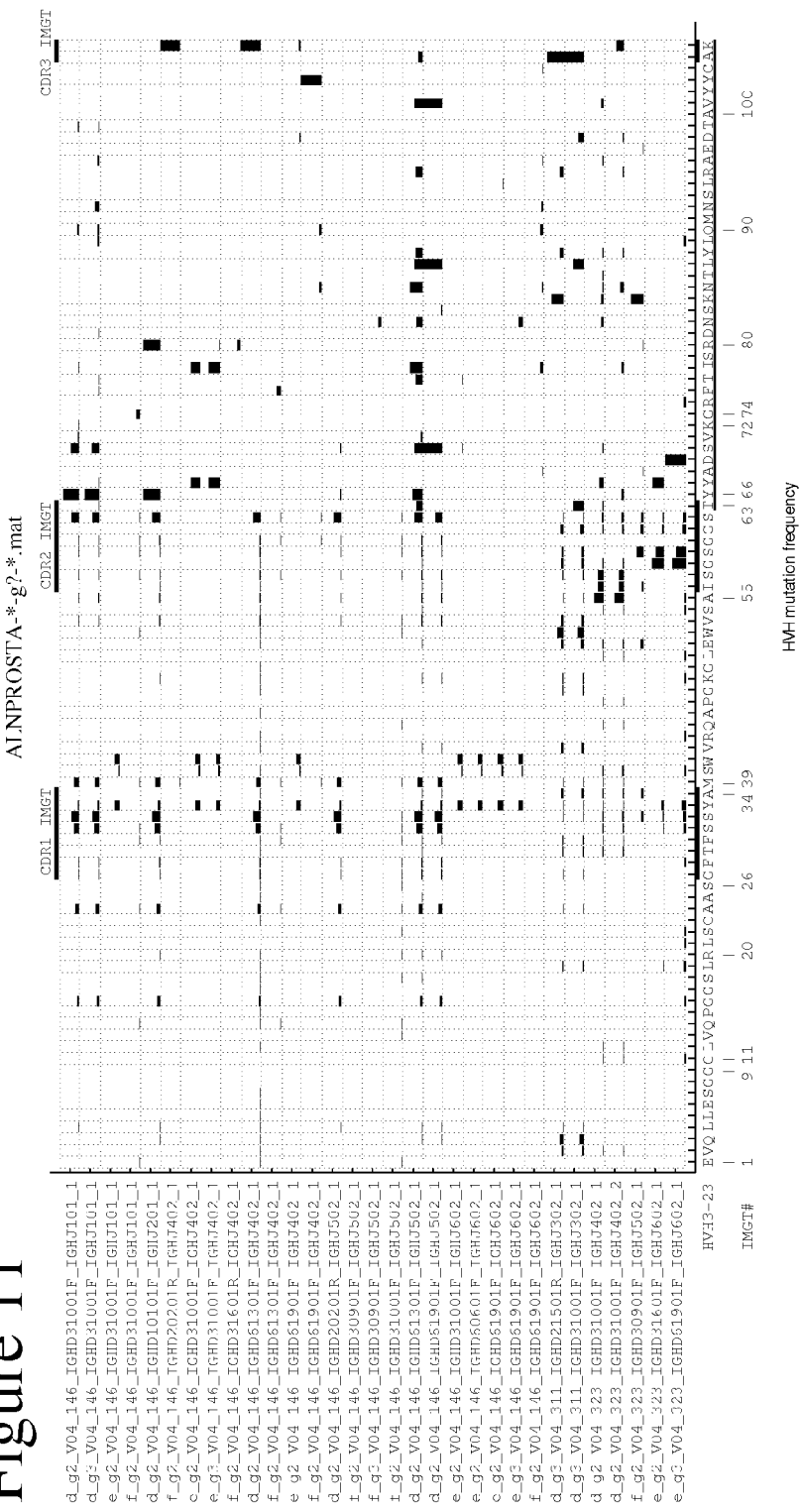

Figure 11

The sequences were obtained by forward (amino acids 1 to 62) and reverse (amino acids 63 to 106) sequencing. The sequences have been classified by D and J regions (left numbering, e.g. D31 or J1 in the top sequence). The mutations indicated are averages of mutations occurring at a particular position. White indicates no mutations, while an increase in the size of the black bar indicates an increase of mutation frequency at that position. Immediately apparent in addition to the expected CDR1, 2 and 3 region mutations are the framework mutations. Numbering is according to the IMGT standard.

SOLUBLE HEAVY-CHAIN ONLY ANTIBODIES

CROSS-REFERENCE TO RELATED APPLICATIONS

The present application is a continuation of U.S. application Ser. No. 13/259,472, filed Feb. 22, 2012, which is the U.S. National Phase entry under 35 U.S.C. §371 of PCT International Application No. PCT/GB2010/000500, filed Mar. 19, 2010, which claims the benefit of priority under 35 U.S.C. §119(a) of British Application No. 0905023.8, filed Mar. 24, 2009, all applications are hereby incorporated by reference in their entireties.

FIELD OF THE INVENTION

The present invention relates to improved methods for isolating from transgenic non-human mammals a diverse repertoire of functional, soluble, heavy chain-only antibodies and soluble VH domains derived therefrom which are structurally distinct from VH domains derived from antibodies comprising heavy and light chains. Preferably, the heavy chain-only antibodies and soluble VH domains are derived from long-lived plasma cells or memory B-cells.

BACKGROUND TO THE INVENTION

Monoclonal antibodies or variants thereof will represent a high proportion of new medicines launched in the 21st century. Monoclonal antibody therapy is already accepted as a preferred route for the treatment for rheumatoid arthritis and Crohn's disease and there is impressive progress in the treatment of cancer. Antibody-based products are also in development for the treatment of cardiovascular and infectious diseases. Most marketed monoclonal antibody products recognise and bind a single, well-defined epitope on the target ligand (e.g. TNFα).

The structure of antibodies is well known in the art. Most natural antibodies are tetrameric and comprise two heavy chains and two light chains. The heavy chains are joined to each other via disulphide bonds between hinge domains located approximately half way along each heavy chain. A light chain is associated with each heavy chain on the N-terminal side of the hinge domain. Each light chain is normally bound to its respective heavy chain by a disulphide bond close to the hinge domain.

When an antibody molecule is correctly folded, each chain folds into a number of distinct globular domains joined by a more linear polypeptide sequence. For example, the light chain folds into a variable (VL) and a constant (CL) domain. Heavy chains have a single variable domain (VH) adjacent the variable domain (VL) of the light chain, a first constant domain (CH1), a hinge domain and two or three further constant domains. Interaction of the heavy (VH) and light (VL) chain variable domains results in the formation of an antigen-binding region (Fv).

The interaction between the heavy and light chains is mediated by the first constant domain of the heavy chain (CH1) and the constant domain (CL) of the light chain. However, there is also an interface between the heavy chain variable domain (VH) and the light chain variable domain (VL) which is involved in the interaction between the heavy chain and the light chain.

As the variable domains have variable amino acid sequences, a system has been devised for numbering the amino acid residues in these domains. This numbering system is described by Kabat et al. ((1991) US Public Health Services, NIH publication 91-3242) and is used in the present specification. In the heavy chain variable domain, framework 1 (FR1) includes residues 1 to 30, framework 2 (FR2) includes residues 36 to 49, framework 3 (FR3) includes residues 66 to 94 and framework 4 (FR4) includes residues 103 to 113. Also, in the heavy chain variable domain, the complementarity determining regions (CDRs) include residues 30 to 35 (CDR1), residues 50 to 65 (CDR2) and 95 to 102 (CDR3).

Normal human B-cells contain a single heavy chain locus on chromosome 14 from which the gene encoding a heavy chain is produced by rearrangement. In the mouse, the heavy chain locus is located on chromosome 12. A normal heavy chain locus comprises a plurality of V gene segments, a number of D gene segments and a number of J gene segments. Most of a VH domain is encoded by a V gene segment, but the C terminal end of each VH domain is encoded by a D gene segment and a J gene segment. VDJ rearrangement in B-cells, followed by affinity maturation, provides each VH domain with its antigen-binding specificity. Sequence analysis of normal tetrameric antibodies demonstrates that diversity results primarily from a combination of VDJ rearrangement and somatic hypermutation (Xu and Davies, (2000) Immunity, 13, 37-45). There are over 50 human V gene segments present in the human genome of which only 39 are functional. In normal diploid antibody-producing B-cells, each cell produces a tetrameric antibody from a single set of heavy and light chain antibody loci. The other set of loci are used, but not productively as the result of a process called allelic exclusion (see Singh et al., (2003) J. Exp. Med., 197, 743-750 and Immunology $5^{th}$ edition, R. Goldsby, T. Kindt, B. Osborne, J. Kuby (2003) W.H. Freeman and Company NY, N.Y. and references therein).

The ability to "remember" encounters with pathogens is a defining feature of the immune system in higher vertebrates. The contribution of B-cells to "memory" appears to be a function of two distinct B-cell populations, long-lived plasma cells and memory B-cells (for review, see Tangye and Tarlinton (2009) Eur. J. Immunol., (2009) 39, 2065-2075). These are generated as a result of the initial primary immune response (antigen challenge) of naïve B-cells. One population is represented by long-lived plasma cells, B-cells which continue to secrete high levels of neutralising antibody for long periods (months) well after the antigen has been cleared. Plasma cells are terminally differentiated and comprise rearranged, affinity-matured immunoglobulin loci encoding high affinity, antigen-specific antibodies. These contrast with short-lived plasma cells, with a life span of a few days, which die as a result of stress caused by the massive production of antigen-specific antibody (see Radbruch et al. (2006) Nature Reviews Immunology, 6, 741-750). In contrast, the second population of antigen-specific memory B-cells represents a B-cell population also comprising rearranged, affinity-matured immunoglobulin loci encoding high affinity antigen-specific antibodies, but which do not secrete antibody at high levels. Memory B-cells have the ability to rapidly divide and differentiate into antibody secreting plasma cells following recurrent exposure to the initial immunising antigen. This results in the rapid enrichment of the pool of antigen-specific immunoglobulin available to respond to a given antigen challenge. Work on smallpox vaccination demonstrates a memory B-cell response in immunised individuals over a period of 50 years (Crotty et al. (2003) J. Immunology, 171, 4969-4973).

In humans, memory B-cells survive in secondary lymphoid organs, comprise rearranged, somatically-mutated immunoglobulin genes and mediate secondary immune responses on re-challenge (see Bernasconi et al. (2002) Science, 298, 2199-2202). The human spleen in particular would appear to be a major site for memory cells (for review, see Tangye and Tarlinton (2009) Eur. J. Immunol., (2009) 39, 2065-2075).

Long-lived antibody-secreting plasma cells survive in secondary lymphoid organs and bone marrow for months. For example, antigen-selected immunoglobulin-secreting cells persist in human spleen and bone marrow (Ellyard et al. (2004) Blood, 103, 3805-3812).

In other mammals, such as the mouse, the primary long-term antibody response appears to be a function of long-lived plasma cells. Thus, in the mouse, terminally-differentiated, long-lived plasma cells, present in bone marrow and spleen, survive and continue to secrete antibodies for extended periods of time, in excess of one year (see Slifka et al. (1998) Immunity, 8, 363-372; Maruyama et al. (2000) Nature, 407, 636-641). Whilst the precise relationship between memory cells and terminally-differentiated, long-lived plasma cells in different mammals remains to be established with certainty, two pools of long-lived B-cells exist in mammals, each comprising rearranged, affinity-matured immunoglobulin loci encoding high affinity antigen-specific antibodies. One has the capacity to divide rapidly. The other does not divide but retains the capacity to secrete antibody over long periods.

Antigen-specific human tetrameric antibodies produced by patients provide a potential source of clinically and commercially relevant antigen-specific antibodies. These may also be derived directly from EBV-transformed human B-cells, preferably from EBV transformed human memory B-cells, optionally transformed in the presence of polyclonal B-cell activators (PCT/IB04/01071).

As yet, memory cells and long-lived plasma cells have not been utilised as a source of transgene-encoded, high affinity antibodies, in particular human antibodies or hybrid antibodies comprising human VH and VL domains.

VH Domain Engineering and Heavy Chain-Only Antibodies

The ability of heavy chain-only antibodies devoid of light chain to bind antigen was established in the 1960s (see Jaton et al. (1968) Biochemistry, 7, 4185-4195). Heavy chain immunoglobulin physically separated from light chain retained 80% of antigen-binding activity relative to the tetrameric antibody. Moreover, binding activity was associated with an amino-terminal fragment (Fd) of the heavy chain. Whilst these experiments used well-characterised, antigen-specific, rabbit polyclonal antibody, they are representative of any polyclonal population comprising a tetrameric antibody of mammalian, including human, origin. The heavy chain dimer retained the CH1 light chain binding domain.

In the 1980s, a number of publications described the in vitro manipulation of heavy chain genes to construct novel antibodies. Much of this work was based on a rearranged mouse antibody µ gene (IgM) encoding an antibody raised against a well-characterised antigen. A feature of this antibody was that antigen-binding specificity was known to reside in the VH domain, since assembly and secretion with an irrelevant light chain showed retention of antigen binding (see Neuberger and Williams (1986) Phil. Trans. R. Soc. Lond., A317, 425-432). Using this system, it was shown that a mouse, antigen-specific VH binding domain could be used to derive a novel antibody comprising a human εconstant region fused to a mouse, antigen-specific VH domain. The resulting chimeric IgE retained antigen specificity and showed effector activity expected of an IgE (see Neuberger et al. (1985) Nature, 314, 268-270).

Other literature examples of heavy chain engineering include the production of a chimeric, mouse-human antibody comprising a mouse VH fused to human IgA or IgG constant regions (see Morrison et al. (1984) PNAS, 81, 6851-6855; Sun et al. (1987) PNAS, 84, 214-218); and Heinrich et al. (1989) J. Immunol., 143, 3589-97). Thus, by the end of the 1980s, the concept of heavy chain engineering was well established. Any characterised VH binding domain could be fused with any antibody constant region, resulting in the retention of antigen-specific binding activity. Effector function was determined by the heavy chain constant region selected (e.g. IgG1, IgG2, IgG3, IgG4, IgA, IgE etc.). The final expressed chimeric antibody in all instances comprised a tetrameric antibody.

To engineer a fully human heavy chain requires a source of human VH domains of defined binding specificity. This problem was partially resolved by the development of human VH binding domain array libraries derived using combinations of naïve germ-line human V, D and J segments or affinity-matured VH domains derived from tetrameric antibodies sourced from human lymphocytes. Antigen-specific VH domains with binding affinities in the 20 nM to 100 nM range could then be isolated from VH binding domain display libraries derived from the mRNA of human antibody-producing peripheral blood B-cells (see Ward et al. (1989) Nature, 341, 544-546) or from random VDJ arrays derived from naïve human germ line DNA (see EP-A-0 368 684). These approaches provided a source of antigen-specific, mammalian VH domains and in particular human VH domains.

It was proposed that:

"Isolated variable (VH) domains may offer an alternative to monoclonal antibodies and serve as a key to building high-affinity human antibodies";

"By attaching variable domains to light or suitable heavy chain constant domains and expressing the assembled genes in mammalian cells, complete antibodies may be made and should possess natural effector functions such as complement lysis"; and "This approach could prove valuable for building human antibodies of therapeutic value" (see Ward et al. (1989) Nature, 341, 544-546 and EP-A-0 368 684).

Using an alternative approach, Sitia et al. ((1990) Cell, 60, 781-790) demonstrated that removal of the CH1 domain from a rearranged mouse µ gene resulted in the synthesis and secretion of a heavy chain-only antibody devoid of light chain by mammalian cells in culture. In this instance, the secreted heavy chain comprised a VH binding domain and a constant region consisting of a flexible hinge domain and IgM CH2, CH3 and CH4 constant domains, providing for heavy chain dimerisation and effector function.

Thus, by 1990, the basic tools were available for the in vitro engineering of human heavy chain-only antibody homodimers (sometimes described as Dabs-Fc) with defined VH binding specificities and a choice of heavy chain effector regions devoid of CH1.

The problem with the approach was two-fold:

VH domains selected by array approaches were of relatively low (20-100 nM) antigen-binding affinity; and VH domains in the absence of light chain were "sticky", insoluble and prone to aggregation, and so not suited to pharmaceutical applications.

The tendency for isolated VH domains to aggregate is a consequence of the absence of light chain. When light chain is absent, certain hydrophobic side chains, which are normally buried within the heavy/light chain interface, are exposed. Furthermore, thermodynamic stability is compromised as stability of VH domains is dependent on contacts at the light chain interface (see Worn and Pluckthun (1999) Biochemistry, 38, 8739-8750).

The description by Hamers-Casterman of a naturally-occurring IgG homodimeric heavy chain-only antibody devoid of light chain which circulated in camelids, in addition to normal camelid tetrameric antibody (see Hamers-Casterman et al. (1993) Nature, 363, 446-448) provided insight into the solubility problem. Consistent with the molecule engineered by Sitia et al. ((1990) Cell, 60, 781-790), CH1 domain functionality was absent in camelid heavy chain-only antibody due to an alternative splice site which eliminated CH1 from the processed antibody heavy chain mRNA.

The VH domains of camelid heavy chain-only antibodies (which are hereafter referred to as VHH domains, in accordance with common usage) derived by antigen challenge are affinity-matured in B-cells in vivo, have binding affinities in the low nanomolar range, are soluble and are not prone to aggregation (see Ewert et al. (2002) Biochemistry, 41, 3628-3636). Camelid VHH domains also generally show increased heat stability relative to germ-line-derived VH domains isolated by display approaches and some retain binding activity in the presence of denaturing agents, such as detergents and bleaching agents, and after heat treatment (see Dumoulin et al. (2002) Protein Science, 11, 500-511 and Dolk et al. (2005) Applied Environmental Microbiology, 71, 442-450).

Antigen-specific heavy chain-only antibodies can be recovered from camelid B-cell mRNA by standard cloning technology or by phage or other display technology (see Riechmann and Muyldermans (1999) J. Immunol. Methods, 231, 25-38). Heavy chain-only antibodies derived from camelids are of high affinity. Sequence analysis of mRNA encoding heavy chain-only antibody demonstrates that diversity results primarily from a combination of VHHDJ rearrangement and somatic hypermutation, as is also observed in the production of normal tetrameric antibodies. However, it remains to be established whether the production by camelids of heavy chain-only antibodies, as opposed to tetrameric antibodies, is by normal B-cells. Indeed, little is known about pre-B cell development in camelids (see WO2004/049794 and Zou et al. (2005) J. Immunology, 175, 3769-3779). Furthermore, it remains to be established whether camelid heavy chain-only antibodies, like immunoglobulin tetramers comprising heavy and light chain, participate in long-term antibody responses via memory cells or long-lived plasma cells.

A particular feature of camelid heavy chain-only antibodies is that some amino acid residues which, in a normal VH domain, interact with the VL domain, are mutated in a VHH domain. Thus, the leucine found at position 45 in 98% of human and murine VH sequences has been mutated. It has been proposed that these camelid mutations, which are conserved in the germ-line, are consistent with maintaining VHH solubility in the absence of light chain. Other hallmark amino acid mutations in camelid VHH domains, as compared to normal VH domains, have also been described. Of these, the most common and important changes occur at four positions (VHH tetrad) in the second framework region and function to reduce the hydrophobicity of the former light chain interface. Generally Glu-44 and Arg-45 are found in place of the less hydrophilic Gly-44 and Leu-45 present in normal VH domains, whilst the hydrophilicity at position 47 is increased by the substitution of Trp with smaller residues. The fourth change requires the replacement of Val-37 by Phe or Tyr. Structural analysis reveals that this nucleates a small hydrophobic core typically involving Tyr-91, Trp-103, Arg-45 and hydrophobic residues present in the VHH domain CDR3 loop. These changes increase the hydrophilicity of the former light chain interface by direct substitution with more hydrophilic side chains or by sequestration of hydrophobic side chains from solvent by interaction between the CDR3 and framework residues (see Bond et al. (2003) J. Mol. Biol., 332, 643-655).

In the VHH domain, the CDR3 loop is enlarged relative to that present on camelid tetrameric antibodies and other well-characterised tetrameric antibodies from man and mouse (see Riechmann and Muyldermans (1999) J. Immunol. Methods, 231, 25-38). The role of key hydrophobic residues present in the VHH CDR3 loop, for example in the llama VHH domain, demonstrates a structural role for CDR3 in the stability and solubility of VHH domains (see Bond et al. (2003) J. Mol. Biol., 332, 643-655). Collectively, structural studies on VHH domains demonstrate that the stability and solubility of these domains are dependent on CDR3, in addition to framework residues, and that the requirement for key hydrophobic residues places significant constraints on the type of CDR3 loop compatible with the favourable biophysical characteristics of VHH domains relative to VH domains (see Barthelemy et al. (2008) J. Biol. Chem., 283, 3639-3654).

However, in spite of a high degree of sequence conservation between camelids and man, camelid VHH domains remain of camelid origin and so are potentially antigenic in man. Humanisation in vitro may diminish this risk but at the expense of potentially decreased affinity and solubility as a result of the in vitro engineering involved.

Human VH Binding Domains and the Solubility Problem

The poor biophysical characteristics of human and other mammalian VH domains derived from germ-line sequences or from normal tetrameric antibodies relative to camelid VHH domains, in particular the tendency to aggregate, currently limits their utility as reagents, diagnostics and as medicines (see Rosenberg (2006) The AAPS Journal, 8(3), Article 59 E501-E507 and Fahrner et al. (2001) Biotechnol. Gen. Eng. Rev., 18, 301-327).

Initial attempts to resolve solubility issues relied on the introduction of camelising amino acid sequences into selected human VH binding regions at the VH/VL interface. This approach has proved disappointing since stability and solubility cannot be addressed by "camelisation" at position 45 of the VH/VL interface alone (see Domantis submissions dated 18 May 2007 and 5 Jun. 2007 in opposition to EP-B-0 656 946). Indeed, the introduction of targeted "camelising" mutations is not sufficient to resolve issues of "stickiness" in isolated human VH domains (see Riechmann and Muyldermans (1999) J. Immunol. Methods, 231, 25-38). The introduction of camelising mutations leads to deformations in the framework β-pleated sheet potentially responsible for the reduced protein stability observed as an outcome of these experiments (see Riechmann (1996) J. Mol. Biol., 259, 957-969). Moreover, the role of CDR3, comprising key hydrophobic residues, in maintaining structural stability and solubility of VHH domains in the absence of light chain adds to the complexity, potentially limiting the diversity of CDR3 sequences to those compatible with the camelid framework (see Barthelemy et al. (2008) J. Biol. Chem., 283, 3639-3654).

Thus, mammalian VH domains, including those from man, derived from affinity-matured natural tetrameric antibodies or from naïve arrays of germ-line VDJ segments are, in the absence of light chain, relatively insoluble and prone to aggregation. Such VH domains lack the necessary biophysical characteristics of a soluble VH domain suited to use as medicines.

Heavy Chain-Only Antibodies and Soluble Human VH Domains Generated In Vivo by Transgenesis For pharmaceutical applications, soluble VH binding domains will be preferably of human origin with features such as high antigen-binding affinity and solubility under physiological conditions in the absence of aggregation. Such soluble VH binding domains can also be used as diagnostics and reagents and will have widespread applications in industry and agriculture.

An alternative approach for generating antigen-specific heavy chain-only antibodies is to use transgenic mice comprising heavy chain loci devoid of CH1 functionality (see Janssens et al. (2006) PNAS, 103:15130-5 and WO02/085944).

At the outset, it was not known whether normal murine B-cells would be activated and secrete heavy chain-only antibodies as a result of antigen challenge or whether such antibodies would prove soluble. Furthermore, it was not known whether IgM was required or, as in the camelid, whether expression would be limited to Igγ2 and Igγ3 classes of antibody, or even whether potentially insoluble VH domains could be secreted by normal murine B-cells.

Janssens et al. ((2006) PNAS, 103:15130-5) describe a chimeric heavy chain gene locus comprising two llama VHH gene segments, all human D and J gene segments and combinations of gene segments encoding human Cµ and Cγ2 and Cγ3 constant regions, all lacking CH1 functionality. The choice of the llama VHH gene segments ensured that germline framework mutations maintained in camelids at the VH/VL interface are also present in the expressed camelised human locus so as to enhance the possibility that the resulting "camelised" VH domain might retain the characteristics of solubility and stability exhibited by the camelid VHH, so increasing the likelihood of a functional response to antigen challenge even in the absence of a CDR3 loop derived from camelid.

The outcome demonstrated that a heavy chain-only antibody transgene is expressed in a B-cell specific manner, that B-cell expansion occurs and that, in the absence of CH1 functionality, the presence of any functional light chain gene is irrelevant. Heavy chain-only transgenes undergo VDJ rearrangement, followed by B-cell activation and affinity maturation in response to antigen challenge. Class switching between heavy chain-only IgM and IgG also occurs, as does Cγ isotype switching. In the absence of Cµ from the locus, Cγ is used equally well. Specificity of the antibodies is largely determined by the VDJ (CDR3) rearrangement, while analysis of somatic mutations shows that these occur throughout the VH region, with a preference for the CDR1 and CDR2 regions of the expressed llama VHH gene segment. Of the limited number of camelised human heavy chain-only antibodies characterised, all proved soluble whether derived from splenic B-cells by phage display of VH domains or by hybridoma selection, in spite of the fact that the CDR3 loop, which was derived entirely from human sequences, was smaller than those found in camelid VHH domains.

The best hybrid llama/human heavy chain-only antibodies of this limited series had affinities in the 1-3 nM range. The mouse also treats the transgene as another heavy chain locus in that B-cell expansion and splenic architecture is essentially normal even in the absence of light chain rearrangement (see Janssens et al. (2006) PNAS, 103:15130-5). Moreover, allelic exclusion mechanisms determine whether the endogenous mouse heavy chain locus or the heavy chain transgene lacking CH1 functionality is productively expressed (see WO2007/09677).

The observations of Janssens et al. ((2006) PNAS, 103:15130-5) demonstrate surprisingly that stable, soluble, camelised heavy chain-only antibodies may be derived using a camelid framework even in the absence of CDR3 loop comprising camelid sequences.

As an extension of these experiments (see WO2006/008548), additional transgenic mouse lines have been built which comprise fully human heavy chain-only gene loci, and so lack sequence encoding the camelid VHH framework and, in addition, comprise CDR3 loops derived from non-camelid sequences.

In this approach, four natural human germ line VH gene segments (V4 natural locus) have been introduced, so relying entirely on natural selection through affinity maturation for the generation of antigen specificity and structural stability of the resultant soluble human VH domains. Both loci comprise all human D and J gene segments, human Cγ2 and Cγ3 constant region gene segments, each lacking CH1, the human immunoglobulin enhancer regulatory elements and, preferably, the antibody heavy chain LCR.

The human V4 locus is functional and human heavy chain-only antibodies circulate in the plasma of unchallenged animals. Following antigen challenge, antigen-specific human antibodies are detected using routine Elisa assays. Human loci comprising engineered V gene segments (V17 locus) (see also WO2008/035216) are also functional (see also The Antibody Engineering and Antibody Therapeutics Meeting. F. Grosveld presentation, San Diego Antibody Meeting, Dec. 3-4, 2007).

Furthermore, surprisingly, antigen challenge of transgenic mice comprising V4 loci allows the isolation and characterisation of soluble, antigen-specific, high affinity human VH domains in the absence from the germ-line of camelid hallmark framework mutations and the camelid-like CDR3 loop typical of camelid VHH domains. Moreover VH domains derived from antigen-specific human heavy chain-only antibodies are soluble (see WO2006/008548). Following antigen challenge, VDJ rearrangement and subsequent B-cell expansion, splenic architecture in mice comprising the human V4 locus is essentially similar to a wild type mouse immunoglobulin response to antigen challenge. Light microscopy shows segregation of T cell clustering in the peri-arteriolar lymphocyte sheet (PALS) surrounded by B-cell-rich areas containing follicles and marginal zones present at the outer boundaries of the white pulp. There are also structures similar to germinal centres in B-cell follicles of secondary lymphoid tissues comparable to wild type mice during T-cell-dependent antibody responses.

An alternative display approach to the identification and engineering of synthetic human VH domains which is not dependent on predictive analysis of natural camelid VHH domain sequences also demonstrates that autonomous VH domains with structural properties beyond the scope of natural frameworks can be derived using non-natural mutations which differ from those found in camelid (see Barthelemy et al. (2008) J. Biol. Chem., 283, 3639-3654 and U.S. patent application Ser. No. 11/102,502). However, the data do not demonstrate whether such VH domains retain the biophysical characteristics of solubility under physiological conditions in the absence of aggregation in combination with binding affinities in the low nanomolar range.

Approaches for the identification and engineering of synthetic human VH domains by display, whilst elegant, are labour intensive and limited in scope to the availability of human VH domains and camelid VHH three dimensional structural information. Subtle differences will become apparent dependent on the VDJ combinations used, which will limit the development of synthetic array-based VH libraries with CDR3 diversities unconstrained by structural demands which maintain high affinity antigen-binding. Whilst the outcomes demonstrate that, in contrast to camelid VHH domains, soluble, stable conformations of human VH domains are not dependent on interactions between the CDR3 loop and camelid hallmark amino acid substitutions at the former light chain interface, the data are limited to biophysical characteristics. For example, the maintenance of high affinity antigen binding in the context of these changes has not been considered.

The Invention

The present invention describes novel soluble high affinity heavy chain-only antibodies and soluble VH domains structurally distinct from VH domains derived from normal tetrameric antibodies or germ-line arrays, so suited to use as medicaments, and preferred routes for isolating such novel heavy chain-only antibodies and soluble VH domains from transgenic animals following antigen challenge.

Accordingly, the first aspect of the present invention provides a novel high affinity, antigen-specific, soluble heavy chain-only antibody which:

lacks hallmark camelid-related amino acid substitutions and has FR2 substitutions which are not found in normal tetrameric antibodies;

shows increased net hydrophobicity within CDR1 and an increased number of charged amino acids present in CDR3; and comprises one or more amino acid substitutions within the framework β-pleated sheet leading to increased net hydrophobicity within FR1 and an increased number of charged amino acids present in FR3.

The heavy chain-only antibody preferably is a human antibody. The human heavy chain-only antibody lacks hallmark camelid-related amino acid substitutions and has FR2 substitutions which are not found in normal human tetrameric antibodies.

The heavy chain-only antibody preferably has a binding affinity of 10 nM or better, and acts as a soluble monomer on gel filtration under physiological buffering conditions.

The present invention also provides a high affinity, antigen-specific soluble VH domain which:

lacks hallmark camelid-related amino acid substitutions and has FR2 substitutions which are not found in normal tetrameric antibodies;

shows increased net hydrophobicity within CDR1 and an increased number of charged amino acids present in CDR3; and comprises one or more amino acid substitutions within the framework β-pleated sheet leading to increased hydrophobicity within FR1 and an increased number of charged amino acids present in FR3.

The soluble VH domain is preferably of human origin. The soluble human VH domain lacks hallmark camelid-related amino acid substitutions and has FR2 substitutions which are not found in normal human tetrameric antibodies.

The soluble VH domain preferably has a binding affinity of 10 nM or better and acts as a soluble monomer on gel filtration under physiological buffering conditions.

The present invention further provides a V gene segment which, when recombined with a D gene segment and a J gene segment and subsequently undergoes affinity maturation, encodes a soluble VH domain according to the invention.

Optionally, the sequence of the V gene segment may be engineered by way of at least one substitution, insertion or deletion, or a combination thereof, relative to the natural germ-line sequence of the V gene segment so that it includes codon(s) encoding amino acid residues or amino acid sequences which differ from the germ line sequence of the host animal, are not hallmark camelid-related amino acid substitutions, and may be FR2 substitutions which are not generally found in normal tetrameric antibodies. Such changes may include substitutions, insertions or deletions, or a combination thereof within the CDR1 and/or CDR2 regions of the V gene segment so as to enhance the diversity of amino acids available for antigen binding relative to germ-line sequences.

The present invention further provides a D gene segment which, when recombined with a V gene segment according to the invention and a J gene segment, encodes a VH domain according to the invention.

Optionally the sequence of the D gene segment may be engineered by way of at least one substitution, insertion or deletion, or a combination thereof, relative to the natural germ-line sequence of the D gene segment. Such substitution, insertion or deletion, or a combination thereof, such that the D gene segment may include codons encoding amino acid residues which have been determined to contribute to maintaining solubility and stability of a soluble VH domain, including sequences encoded by the D gene segment, or alternatively may enhance the diversity of the D gene segment in any resulting CDR3 loop relative to germ-line sequences.

The present invention yet further provides a J gene segment which, when recombined with a V gene segment according to the invention and a D gene segment, encodes a soluble VH domain according to the invention.

Optionally, the sequence of the J gene segment may be engineered by way of at least one substitution, insertion or deletion, or a combination thereof, relative to the natural germ-line sequence of the J gene segment. Such substitution, insertion or deletion, or a combination thereof such that the J gene segment may include codons encoding amino acid residues which have been determined to contribute to maintaining solubility and stability of a VH domain including sequence encoded by the J gene segment, or alternatively may enhance the diversity of the J gene segment in any resulting CDR3 loop relative to germ-line sequences.

The present invention preferably provides a heterologous heavy chain-only locus comprising one or more V gene segments according to the invention, one or more D gene segments according to the invention, one or more J gene segments according to the invention and one or more constant effector region gene segments, each of which encodes an antibody constant effector region lacking CH1 functionality, wherein the gene segments are arranged such that a V, a D and a J gene segment and a constant region gene segment can recombine to produce a rearranged gene encoding a high affinity, antigen-specific, soluble heavy chain-only antibody according to the invention.

The heavy chain-only locus has a vertebrate heavy chain constant effector region(s) which are preferably of mammalian origin, more preferably derived from human, mouse, rat or camelid.

Preferably, the heavy chain locus is arranged to produce a heavy chain-only antibody comprising a soluble human VH domain and a constant effector region of mammalian origin.

The invention yet further provides a transgenic non-human mammal comprising a heterologous heavy chain locus according to the invention. Preferably, the mammal is a rodent, most preferably a mouse or a rat. Preferably, the endogenous heavy chain locus of the transgenic non-human mammal has been functionally impaired by any method known in the art, or silenced by deletion (see U.S. Pat. Nos. 5,591,669; 6,162,963; and No. 5,877,397; Kitamura and Rajewsky (1992) Nature, March 12; 356(6365) :154-6). Alternatively, B-cells which express endogenous immunoglobulin genes, as opposed to transgenes, may be ablated. Endogenous kappa and lambda light chain genes may retain functionality or optionally may be functionally silenced or deleted (EP139959). Less preferably, the transgene may be a normal heavy chain antibody locus which comprises CH1 functionality in a host background devoid of endogenous heavy or light chain gene functionality (see EP139959 and Zou et al. J. Exp. Med., 204, 3271-3283).

The heavy chain-only immunoglobulin transgene may also comprise endogenous heavy chain immunoglobulin gene loci which have been engineered to eliminate CH1 functionality, and optionally further engineered to introduce or replace one or more endogenous V, D and J gene segments with alternative V, D and J gene segments, preferably of human origin.

The present invention, in another aspect, provides a method for the production of a high affinity, antigen-specific, soluble heavy chain-only antibody, which comprises challenging a transgenic non-human mammal according to the invention with an antigen. Preferably, the soluble heavy chain-only antibody is human.

Preferably, the method includes the step of immortalising antibody-producing cells from the mammal. The cells may be immortalised by fusion with a myeloma cell or may be immortalised by transformation with a virus, such as the EBV.

Preferably, the method further includes the step of isolating either the soluble VH domain or a nucleic acid encoding the soluble VH domain from a B-cell or an immortalised cell line producing a heavy chain-only antibody of desired antigen-specificity.

Alternatively, the method may further include the step of isolating either a soluble VH domain or a nucleic acid encoding a soluble VH domain from a heavy chain-only antibody-producing cell produced by the mammal or from an immortalised heavy chain-only antibody-producing cell produced by the mammal by a display approach.

The present invention also provides use of a soluble VH domain or a nucleic acid encoding a soluble VH domain obtained by the method of the invention in the production of a heavy chain-only antibody, a VH intrabody, a VH polyprotein, a VH domain complex or a VH fusion.

The present invention further provides a heavy chain-only antibody, a VH intrabody, a VH polyprotein, a VH domain complex or a VH fusion including at least one soluble VH domain according to the invention.

The present invention yet further provides a heavy chain-only antibody, a VH intrabody, a VH polyprotein, a VH domain complex or a VH fusion including at least one soluble VH domain according to the invention for use in therapy.

The present invention also provides use of a heavy chain-only antibody, a VH intrabody, a VH polyprotein, a VH domain complex or a VH fusion including at least one soluble VH domain according to the invention in the preparation of a medicament for use in treatment of diseases or disorders including but not limited to: wound healing, cell proliferative disorders, including neoplasm, melanoma, lung, colorectal, osteosarcoma, rectal, ovarian, sarcoma, cervical, oesophageal, breast, pancreas, bladder, head and neck and other solid tumours; myeloproliferative disorders, such as leukemia, non-Hodgkin lymphoma, leukopenia, thrombocytopenia, angiogenesis disorder, Kaposis' sarcoma; autoimmune/inflammatory disorders, including allergy, inflammatory bowel disease, arthritis, psoriasis and respiratory tract inflammation, asthma, immunodisorders and organ transplant rejection; cardiovascular and vascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; developmental disorders; metabolic disorders including diabetes mellitus, osteoporosis, and obesity, AIDS and renal disease; infections including viral infection, bacterial infection, fungal infection and parasitic infection, pathological conditions associated with the placenta and other pathological conditions and for use in immunotherapy.

The present invention yet further provides a cassette for producing a soluble VH domain according to the invention, which comprises gene sequences encoding FR1, FR2 and FR3, wherein the gene sequences encoding FR1 and FR2 and FR2 and FR3 are separated by sequences allowing the introduction of suitable CDR1- and CDR2-encoding sequences and, at the 3' end of the sequence encoding FR3, there is a sequence allowing the introduction of a sequence encoding suitable CDR3-encoding sequences.

The invention takes advantage of natural mammalian B-cell mechanisms in a non-human transgenic mammal, preferably a mouse or rat, to generate novel high affinity, soluble heavy chain-only antibodies in response to antigen challenge. The soluble heavy chain-only antibodies of the invention have binding affinities of 10 nmol or better.

Sequence analysis of soluble human VH binding domains derived from antigen-specific, high affinity human heavy chain-only antibodies devoid of light chain reveals, surprisingly, that all amino acid hallmark consensus sequences typical of camelid VHH domains are absent. Indeed, natural selection does not compensate by the selection of camelid-like hallmark sequences as a consequence of affinity maturation. Thus, where camelid hallmark sequences are absent from the germ-line, different mechanisms operate in vivo which compensate for the absence of light chain so as to maintain structural stability and solubility of the human VH domain.

The most surprising feature is that not only are antigen-specific, high affinity human heavy chain-only antibodies devoid of light chain soluble, but that the antigen-binding regions (CDRs) must play a role in structural stability and solubility, in addition to antigen-binding, and that the hallmark camelid VHH germ-line-encoded framework consensus amino acid substitutions, which compensate for the absence of light chain at the former light chain interface, are not only absent in the transgenic heavy chain-only loci but are not inserted as a result of affinity maturation to compensate for solubility during natural selection processes. In transgene-encoded soluble human VH domains, alternative amino acid substitutions can occur within all three framework regions following affinity maturation. The framework mutations reside predominantly, but not exclusively, within the β-pleated sheet at the former light chain interface, so compensating for the absence of light chain.

Comparative analysis of the net charge and hydrophobicity of framework and CDR regions of human antigen-binding VH domains derived in the presence and absence of light chain reveal significant changes in the absence of light chain. In the absence of light chain, there is increased net hydrophobicity of amino acids present in CDR1 and an increase of charged amino acids present in CDR3. Amino acid substitutions within the framework β-pleated sheets lead to a decrease in overall hydrophobicity and an increase in charged amino acids present in framework 3. There is an increase in the number of charged amino acids and hydrophobicity in framework 1 and a small reduction of hydrophobicity in framework 2. This is in some contrast to the VHH domains of camelids, such as llama, where a comparable analysis reveals features common with the human VH domain in the absence of light chain, but also differences. In camelids, such as the llama, there is significant reduction in the net hydrophobicity with framework 2, consistent with the increased hydrophilicity introduced by the hallmark amino acid substitutions at the former light chain interface, and increased net charge within CDR3.

Thus, following antigen challenge, B-cells compensate for the absence of light chain, even when necessary amino acid substitutions are absent from the germ-line, as found in camelids, such as llamas and related species.

In the absence of germ-line sequences which compensate for the absence of light chain, different solutions are found in vivo, all leading to the production of high affinity, stable soluble heavy chain-only antibodies and soluble VH domains in the absence of light chain.

These observations are consistent with a major role for the antigen-binding regions (CDRs) in the stabilisation of the VH domain in addition to antigen-binding. This is complemented by subsequent rare or novel amino acid substitutions within the framework, particularly within the β-pleated sheet at the former light chain interface. In soluble VH domains of non-camelid origin derived in vivo by transgenesis, the hallmark camelid amino acid substitutions central to VHH solubility and stability are absent.

Non-camelid antigen-specific heavy chain-only antibodies comprising these features are soluble and do not aggregate under normal physiological conditions. Moreover, soluble VH domains isolated from these antibodies retain the favourable features of VH domain stability and solubility. These heavy chain-only antibodies and soluble VH domains derived from them evolve by natural selection mechanisms in a B-cell specific manner following antigen challenge. High affinity antibodies (10 nm or better) derived from the same VDJ rearrangement generally comprise more framework substitutions than those observed in heavy chain-only antibodies of lower affinity.

Thus, the antigen-binding domains (CDRs) and the β-pleated framework contribute to overall stability, solubility and binding affinity of these heavy chain-only antibodies devoid of light chain or the soluble VH domains derived therefrom.

Sequence analysis of stable, high affinity antigen-specific soluble VH binding domains identifies that:

selection and affinity maturation within the antigen-binding regions (CDRs) is consistent with overall increased hydrophobicity and charge, leading to specificity and affinity of antigen binding and structural stability;

mutations present in frameworks 2 and 3 around the former light chain interface are consistent with improved VH domain solubility and stabilisation and consequently improved antigen-binding affinity;

mutations within frameworks 1 and 3 are consistent with compensatory structural mutations which enhance the overall stability of the VH domain.

Thus, in the absence of antibody light chain, a mammalian B-cell can compensate by affinity maturation and selection for the inherent instability and insolubility of the heavy chain VH binding domain whilst maintaining antigen-binding affinity.

Our analysis shows that natural mechanisms appear to act independently of the V gene segment used. Thus, mass sequencing of human VH domains generated in the human V4 transgenic mouse spleen in the absence of light chain allows a comparative analysis of mutation frequency. The greatest mutational load is observed within CDR1 and CDR2. However, hotspots of mutational load can be discerned within framework 1, framework 2 and broadly across framework 3. The overall pattern which emerges does not appear to be peculiar to the specific V gene segment used since, in this series of experiments, high affinity antibodies have been obtained using V3-23, V3-11 and V1-46 with similar patterns of mutational load emerging. Similarly, in CDR3, J4 predominates but is not used exclusively.

It would appear that B-cell affinity maturation mechanisms have multiple roles in the processing and secretion of soluble VH domains in the absence of light chain. Hypermutation within the CDRs primarily reflects antigen-binding affinity, but would appear also to play a role in structural stability. Hypermutation within the framework regions compensates for the absence of light chain, but also appears to enhance stability and hence solubility of the VH domain and, through this, also maximises antigen-binding affinity. We would presume that solubility and stability of heavy chain-only antibodies lacking light chain is a requirement for efficient intracellular trafficking to the cell surface, presentation and subsequent B-cell expansion.

Favourable framework mutations may also be built into new germ-line heavy chain-only antibody loci comprising engineered human V segments each comprising preferred amino acid substitutions.

Similarly, preferred amino acid substitutions maybe engineered into J and D gene segments to further enhance the solubility and stability of VH domains following VDJ rearrangement.

Thus, there are provided high affinity, soluble, human heavy chain-only antibodies which lack hallmark camelid-related amino acid substitutions and which show increased hydrophobicity within CDR1 and increased charged amino acids within CDR3, relative to VH domains found in normal tetrameric human antibodies. High affinity, soluble, human heavy chain-only antibodies also comprise one or more amino acid substitutions within the framework β-pleated sheet, leading to increased overall hydrophobicity in framework 1, decreased hydrophobicity in framework 3 and an increase in charged amino acids present in framework 3 relative to normal tetrameric human antibodies.

The approach allows for the natural selection of novel heavy chain-only antibodies. The soluble VH domains derived from such antibodies comprise mutations which are rare or absent from those observed in natural tetrameric antibodies where VH solubility is dependent on interaction with the VL domain of immunoglobulin kappa or lambda light chains. In the absence of light chain, the amino acid substitutions observed confer preferred biophysical attributes to resultant antigen-specific heavy chain-only antibodies and soluble VH domains. In particular, heavy chain-only antibodies and soluble VH domains derived by this method lack the tendency of natural VH domains derived from germ-line arrays or natural tetrameric antibodies to be "sticky", relatively insoluble and prone to aggregation. These heavy chain-only antibodies and soluble VH domains of the invention are of high affinity (10 nM or better), are soluble in the absence of aggregation and are particularly suited to use as medicaments.

Superimposing the amino acid substitutions found in high affinity human soluble VH antigen-binding domains on the known 3D structure of the human VH domain present in a normal tetrameric antibody provides insight into the position and functional effect of defined amino acid substitutions. For example:

Framework 1 substitutions were observed from amino acids 13 to 15, with a prevalence for position 13, leading to an overall increase in hydrophobicity. Changes at position 13 are located in a small loop leading to localised increased hydrophilicity;

Framework 2 substitutions can occur within the β-pleated sheet at the former light chain interface, focused around positions 35 and 50; and Framework 3 substitutions appear prevalent at the framework/CDR interfaces, for example at the end of CDR2 (positions 56 and 57) and at the beginning of CDR3 (position 93).

The invention optionally provides for preferred novel framework amino acid insertions or substitutions engineered into natural V gene segments for use in optimised transgenic heavy chain-only antibody loci for the derivation of high affinity, heavy chain-only antibodies and VH domains with preferred biophysical characteristics, including solubility in the absence of aggregation.

Thus, selected soluble human VH domains with preferred biophysical characteristics, such as solubility in the absence of aggregation, are provided. These provide a source of natural heavy chain framework regions which, when combined with one or more CDRs, provides for the further generation of libraries of VH binding proteins, a source for novel antigen-binding proteins (see U.S. patent application Ser. Nos. 11/102,502 and 11/745,644).

The present inventors have also surprisingly shown that transgene-encoded heavy chain-only antibodies are also expressed by murine long-lived plasma cells or memory B-cells, purified from the secondary lymph glands, bone marrow and spleen of antigen-challenged transgenic animals comprising heavy chain-only gene loci. Furthermore, more highly efficient methods have been developed which negate the need for hybridomas or classic display approaches for the recovery of antigen-specific heavy chain-only antibodies or soluble VH domains.

Advantageously cloned cDNA encoding heavy chain-only antibody or soluble VH domains derived from purified plasma cell or memory cell populations of antigen-challenged transgenic animals may be expressed in any cell-line of choice capable of expressing, accumulating, secreting or presenting a VH domain fusion protein or heavy chain-only antibody on the cell surface. The preferred choices are microbial cell-lines or mammalian cell-lines suited to the manufacture of clinical grade material.

Thus according to the second aspect of the invention the heavy chain-only antibodies and soluble VH domains of the first aspect of the invention are derived from host memory B-cells or long-lived plasma cells.

The second aspect of the invention provides a method of producing a heavy chain-only antibody which binds specifically to an antigen comprising:

(a) immunising a non-human transgenic mammal with the antigen, wherein the mammal expresses heavy chain-only antibodies which lack CH1 functionality in the transcribed and processed heavy chain mRNA;

(b) isolating long-lived plasma cells or memory B-cells from the immunised mammal;

(c) isolating an mRNA population from cells derived from step (b);

(d1) cloning a cDNA population derived from the mRNA isolated in step (c) into an expression vector and expressing the cDNA in a cell-line of choice;

(e1) selecting at least one cell-line which produces a heavy chain-only antibody which binds specifically to the antigen; or (d2) cloning a cDNA population comprising VH domains derived from the mRNA isolated in step (c) into expression vector of choice such that a VH fusion protein, which may comprise a heavy chain effector region, is expressed in a cell-line of choice;

(e2) selecting at least one cell-line which produces a VH fusion protein which binds specifically to the antigen.

The cell-line of choice is preferably of mammalian origin but maybe derived from yeast or any organism able to accumulate or secrete heavy chain-only antibodies and VH domain fusion proteins, or present said heavy chain-only antibodies and VH domain fusion proteins on the cell surface.

The method is suited for the isolation of heavy chain-only antibodies, whether produced naturally in the host organism, such as llama, or as a result of an expressed transgenic locus in a non-human host organism.

Preferably, the mammalian cell-line of choice is suited to the production of clinical grade material, e.g. CHO cells.

The method is simple, highly efficient, and well suited to automation, since heavy chain-only antibodies are homodimers, not complex tetramers. There is no need to search for the cognate light chain, a problem which has added greatly to the complexity of deriving antigen-specific tetrameric antibodies from memory cell and plasma cell populations (see Meijer et al. (2009) Therapeutic Antibodies: Methods and Protocols, 525, 261-277).

B-cell populations enriched in long-lived plasma cells or memory cells may be isolated from the host organism by a number of techniques well established in the art. The preferred host organism is a mouse. In the mouse, B-cell populations are well characterised and cell surface markers can be used to differentiate between different sub-populations. For example, mouse plasma cells express CD138 (Syndecan-1) on the cell surface. CD138 expression on cells of the B-cell lineage correlates with developmental stage, location and adhesion (see Sanderson et al. (1989) Cell Regulation, 1, 27-35; Kim et al (1994) Mol. Biol. Cell., 5, 797-805). CD $138^+$ plasma cells are found predominantly in spleen, lymph nodes and bone marrow. Plasma cells may be further distinguished from murine naïve B-cells, memory B-cells and non-B-cell populations in that they are CD138+, CD45R (B220) low/negative and CD19 low/negative.

The availability of antibodies recognising cell surface markers permits the separation of plasma cells from other B-cell populations by fluorescence activated cell sorting, or well established cell separation technologies widely available in kits based, for example, on magnetic, column or centrifugation separation procedures using antibodies conjugated to a solid substrate which allows the binding of one cell population from another. Thus, for example magnetic beads comprising anti CD45R (sometime known as B220) will eliminate most non-plasma cells from a mixed B-cell population. A subsequent incubation with magnetic beads comprising anti-CD138 will capture a highly enriched plasma cell population (see magnetic sorting kit for mouse CD138+ plasma cell isolation from Miltenyi Biotec). Other cell surface markers can also be used to isolate these cells (e.g. Anderson et al. (2007) J. Exp. Med., 204, 2103-14). Also, the starting cell population could be derived from lymph nodes and/or Peyer's patches.

Where cocktails of antibodies which differentiate between given host B-cell lineages are not available, then a combination of B-cell isolation from bone marrow and lymph nodes, followed by B-cell purification using an antibody against a pan B-cell surface marker, will also provide a highly enriched plasma cell population.

This is particularly relevant to species such as cow, rabbit, sheep etc and even human, where cell surface markers such as CD138 may not be available. Markers are available to select for particular B-cell populations of other species (e.g. http://www.miltenyibiotec.com/en/PG_91_625_CD138_Plasma_Cell_Isolation_Kit.a spx; Klein et al., Human immunoglobulin (Ig)M+IgD+ peripheral blood B-cells expressing the CD27 cell surface antigen carry somatically mutated variable region genes: CD27 as a general marker for somatically mutated (memory) B cells, (1998) J. Exp. Med., 188, (9), 1679-89; Denham et al., Monoclonal antibodies putatively identifying porcine B cells, (1998) Vet Immunol Immunopathol. 30; 60(3-4):317-28; Boersma et al., Summary of workshop findings for porcine B-cell markers, (2001) Vet. Immunol Immunopathol., 80, (1-2), 63-78; Naessens, Surface Ig on B lymphocytes from cattle and sheep, (1991) Int. Immunol., 9, (3), 349-54; Sehgal et al., Distinct clonal Ig diversification patterns in young appendix compared to antigen-specific splenic clones, (2002) J. Immunol., 168, (11), 5424-33).

Following mRNA isolation from isolated plasma or memory cell populations, cDNA (representing either the HCAb or VH domains alone) is cloned into the expression vector of choice, and the vector transfected into a target cell population for the expression of heavy chain-only antibodies or VH fusion proteins. Cells expressing antigen-specific heavy chain-only antibodies can be selected, for example by standard Elisa in a 96 well format, or in a microarray format or using fluorescence activated cell sorting (FACS) for the derivation of cell-lines.

Preferably in order to maximise the efficiency of the process, the expression vector is first transfected into bacteria and the colonies containing the cloned cDNA in the expression vector are picked into a 96 well (or other high throughput automatable) format, grown up in the 96 well format and the DNA isolated in the same format. The plasmid DNA is subsequently transfected in the same format into the expression cells (e.g. HEK cells or yeast etc) and the transformants grown up in the same 96 well format. The supernatant of the cells is subsequently tested in the same format (or another, preferably higher density, format such as a microarray, using less antigen) for antigen binding. The antigen-positive HCAb-expressing cells can then be further expanded and the positive cDNAs are immediately available from the original 96 well format in which the DNA was prepared for further characterisation, such as sequence analysis, or the relevant VH domain can be immediately cloned onto a different backbone, e.g. a different constant region from the same species or a different species. The DNA can also immediately be transfected into other cells types to establish other cell lines.

Cell-lines expressing high affinity antibodies may then be expanded, cell banks established, and used as a source of target heavy chain-only antibody for research purposes or potentially pre-clinical or clinical studies. Thus, the method further includes the step of maintaining a selected cell line which produces a heavy chain-only antibody or VH fusion protein which binds specifically to the target antigen.

This direct cloning method would also be advantageous for normal transgene derived tetrameric antibodies where single CD138+ cells are used per well. The (abundant) mRNA coding for the heavy and light chains would be PCR amplified separately using chain-specific primers and each then cloned into the expression vector. Co-transfection of the two would results in the expression of a tetrameric antibody that could be identified in the same way as described for the heavy chain-only antibody.

The expression vectors of choice will be familiar to those skilled in the art and will be designed to drive efficient heavy chain-only antibody or VH fusion protein expression in the cell type of choice. Where secretion is contemplated, the vector will incorporate a signal peptide at the amino terminus Where cell surface expression is contemplated, then there will also be a hydrophobic peptide sequence at the carboxyl terminus. Preferably, but not essentially, such amino and carboxyl peptides may be derived from mammalian heavy chain immunoglobulins. Vectors will be designed in cassette format such that soluble VH domains cloned from antigen-specific heavy chain-only antibodies may be produced as fusion proteins. The resultant fusion protein may be a heavy chain-only antibody, and will comprise a soluble VH domain and the heavy chain effector domain of choice. If the soluble VH domain and the chosen effector domain are of human origin, then the resulting fusion protein will be a human heavy chain-only antibody of the class (and sub-type) specified by the choice of effector region (e.g. IgM, IgG, IgA, IgE or IgD). In any heavy chain-only antibody, the soluble VH domain and the constant effector regions will be linked by a hinge region. Preferably, but not essentially, this will be a natural heavy chain immunoglobulin hinge region derived from the appropriate class or subtype.

The advantage of the above method over other methods, such as phage display or hybridomas using materials derived from total spleen, is that the method selects for the high affinity heavy chain-only antibodies (10 nmol or better) produced in plasma or memory cells following as yet unknown in vivo selection processes. Such B-cell populations yield heavy chain-only antibodies (HCAbs) that are soluble and do not accumulate in intracellular compartments (such accumulation would otherwise lead to apoptosis). Such HCAbs can be expressed efficiently using standard expression systems, in particular in established mammalian cell-lines such as HEK or CHO. Transfected cells may then be arrayed using established technology, typically automatable microwell format (e.g. 96 wells). Those cells expressing high affinity HCAb antigen binders, or alternatively cells expressing HCAbs which bind antigen in a defined range of affinities, can then be selected for further analysis. Alternatively, high affinity binders can be selected by FACS analysis. The use of memory cells or plasma cells derived from one or more antigen-challenged transgenic non-human animals, for example a mouse, which express antigen-specific HCAbs as a source of HCAb mRNA provides an extraordinarily efficient route for HCAb selection, allowing the selection of potentially millions of HCAb-producing cells for subsequent analysis. Selected cells expressing high affinity HCAb antigen binders can then be expanded in culture, providing a source of HCAb-producing cells in the absence of additional cloning steps.

Optionally, the isolated long-lived plasma cells or memory B-cells may be immortalised prior to mRNA isolation and cloning of antigen-specific heavy chain-only antibodies or VH domains.

The present invention also provides a transgenic non-human mammal which has a transgenic heavy chain locus or heavy chain-only locus (lacking CH1 functionality) which includes a dominant selective marker gene. The inclusion of more than one selective markers is also contemplated, each marker being linked to a different locus or group of loci, permitting the preferential selection of hybridomas expressing one as opposed to another locus or group of loci capable of expressing heavy chain-only antibodies.

The use of multiple selective markers on different loci relies on the discovery that, where a transgenic non-human mammal possesses multiple heavy chain-only loci, these loci are subject to allelic exclusion (PCT/IB2007/001491). Therefore, following antigen challenge, only one locus is stochastically chosen and recombined successfully, resulting in the production of a heavy chain-only antibody. Multiple VH heavy chain-only loci can, therefore, be used in the same transgenic non-human mammal to maximise the antibody repertoire and diversity obtainable from the mammal. When antigenically challenged, the transgenic non-human mammal will carry out random recombinations in one locus after another, not preferring any given locus, until one of the recombinations is "productive", i.e. resulting in the generation of an antibody. Further recombination is stopped, thereby "excluding" other alleles (loci). The cells that produce high affinity antibody will be preferentially expanded.

Typically, the dominant selective marker genes will be of prokaryotic origin and will be selected from a group which either confers resistance to toxic drugs, such as puromycin, hygromycin and G418, or comprises genes which obviate certain nutritional requirements such that their expression converts a toxic substance into an essential amino acid, for example the conversion of indole to tryptophan or the conversion of histidinol to histidine. A necessary requirement is that, if a dominant selective marker is used, it is co-expressed with the desired heavy chain-only immunoglobulin allele, so ensuring B-cell expression and integration site-independent expression of a transgenic locus. Alternatively, the drug resistance gene maybe inserted into an endogenous or exogenous (transgenic) immunoglobulin locus using homologous recombination in combination with ES cells or nuclear transfer approaches.

Accordingly, there is provided a method for the production of a monoclonal antibody requiring the selection of a hybridoma or transformed B-cell-line preferably derived from memory or plasma cells expressing a defined immunoglobulin heavy chain-only locus, comprising one of multiple heavy chain-only gene loci present in the non-human transgenic mammal, said locus comprising a co-expressed dominant selective marker gene inserted within said locus.

Preferably, the locus is a heavy chain-only locus comprising a dominant selective marker gene, which locus expresses a heavy chain-only antibody. Preferably, the heavy chain-only antibody is produced from an endogenous heavy chain-only locus engineered to lack CH1 functionality, or an introduced heavy chain transgene lacking CH1 functionality, optionally in the absence of immunoglobulin light chain gene expression. Said locus may also comprise a dominant selective marker and a heavy chain locus in the absence of light chain loci, said heavy chain gene, when expressed, spontaneously giving rise to an mRNA transcript which lacks CH1 functionality, resulting in heavy chain-only antibody expression in a B-cell dependent manner.

According to the third aspect of the invention, where hybridoma or B-cell transformation approaches are contemplated for the immortalisation of plasma or memory cells, then the inclusion of a functional dominant selective marker gene in each heavy chain locus permits the subsequent selection and stable maintenance of hybridoma or transformed B-cell-lines expressing a locus of interest following antigen challenge, whilst losing all the hybridoma cells or transfomed B-cells not expressing that locus of interest. For the purpose of the invention, any dominant selective marker gene can be used, provided that expression of the gene confers a selective benefit to hybridomas in the presence of a selective, for instance toxic, challenge (see Vara et al. (1986) NAR, 14, 4617-4624; Santerre et al. (1984) Gene, 30, 147-156; Colbere-Garapin et al. (1981) 150, 1-14; Hartmann and Mulligan (1988) PNAS, 85, 8047-8051).

The Heterologous Heavy Chain-Only Locus

In the context of the present invention, the term 'heterologous' means a nucleotide sequence or a locus as herein described not endogenous to the mammal in which it is located or an endogenous locus which has been modified by the replacement or removal of endogenous sequences.

A "heavy chain-only locus" in the context of the present invention relates to a locus encoding a VH domain comprising one or more V gene segments, one or more D gene segments and one or more J gene segments, operationally linked to one or more heavy chain effector regions (each lacking CH1 domain functionality).

V gene segment complexity may be increased by increasing the number of V gene segments present in the locus or by using different loci, each comprising different V gene segments.

Preferably, the heavy chain-only locus comprises from five to twenty different V gene segments derived from any vertebrate species.

Preferably, the V gene segments are of human origin, optionally selected or engineered for improved solubility.

Preferably, the heavy chain-only locus comprises from two to forty (2, 3, 4, 5, 6, 7, 8, 9, 10, 12, 14, 16, 18, 20, 30 or 40) or more D gene segments. The D gene segments may be derived from any vertebrate species but, most preferably, the D gene segments are human D gene segments (normally 25 functional D gene segments).

Preferably, the heavy chain-only locus comprises from two to twenty (2, 3, 4, 5, 6, 7, 8, 9, 10, 12, 14, 16, 18 or 20) or more J gene segments. The J gene segments may be derived from any vertebrate species but, most preferably, the J gene segments are human J gene segments (normally 6 J gene segments).

Preferably, the heavy chain-only locus comprises two or more V gene segments, twenty-five functional human D gene segments and 6 human J gene segments.

The term 'V gene segment' encompasses a naturally occurring V gene segment derived from a vertebrate, including camelids and human, which have optionally been selected, mutated or engineered for improved characteristics, such as solubility. V gene segments are also found in other vertebrate species such as shark (see Kokubu et al. (1988) EMBO J., 7, 3413-3422) or have evolved to provide diverse VH-like families of binding proteins exemplified, for example, in the evolution of the antibody light chain VL repertoire or the T-cell receptor VH repertoire.

The V gene segment must be capable of recombining with a D gene segment, a J gene segment and a heavy chain constant (effector) region (which may comprise several exons but excludes a CH1 exon) according to the present invention to generate a heavy chain-only antibody when the nucleic acid is expressed.

A V gene segment according to the present invention also includes within its scope any gene sequence encoding a homologue, derivative or protein fragment which is capable of recombining with a D gene segment, a J gene segment and a heavy chain constant effector region (comprising one or more exons but not a functional CH1 exon) according to the present invention to generate a heavy chain-only antibody as defined herein. The heavy chain constant effector region may comprise a CH1 domain under circumstances where an immunoglobulin heavy chain locus is expressed in a host animal background devoid of immunoglobulin light chain gene expression.

Thus, VH coding sequences may be derived from a naturally occurring source or they may be engineered or synthesised using methods familiar to those skilled in the art.

A "soluble VH domain" in the context of the present invention refers to an expression product of a V gene segment when recombined with a D gene segment and a J gene segment as defined above. Following natural selection and affinity maturation of the parent HCAb, the soluble VH domain as used herein following expression and isolation remains in solution in the absence of aggregation and is active in a physiological medium without the need for any other factor to maintain solubility. The soluble VH domain alone can also be engineered with diverse protein domains to produce fusion proteins for targeted therapeutic and diagnostic purposes, for example with toxins, enzymes and imaging agents, or with blood proteins such as albumin to manipulate soluble VH domain pharmacokinetics and tissue distribution in vivo (see U.S. Pat. No. 5,843,440 and Smith et al. (2001) Bioconjugate Chem., 12, 750-756).

In the context of the present invention, the terms 'a D gene segment' and 'a J gene segment' include naturally-occurring sequences of D and J gene segments. Preferably, the D and J gene segments are derived from the same vertebrate from which the V gene segment is derived. For example, if a V gene segment is derived from a human and then solubilised or engineered, the D and J gene segments are preferably also derived from a human. Alternatively, the V gene segments may be derived, for example, from rat or mouse and the D and J gene segments from camel or human.

The terms D gene segment and J gene segment also include within their scope derivatives, homologues and fragments thereof as long as the resultant segment can recombine with the remaining components of a heavy chain antibody locus as herein described to generate a heavy chain-only antibody as herein described. D and J gene segments may be derived from naturally-occurring sources or they may be synthesised using methods familiar to those skilled in the art and described herein. D and J gene segments may incorporate defined additional amino acid residues or defined amino acid substitutions or deletions with a view to increasing CDR3 diversity.

The V, D and J gene segments are capable of recombination and preferably undergo somatic mutation.

The V, D and J gene segments are preferably derived from a single vertebrate species. This may be any vertebrate species but is preferably a human.

Hallmark sequences are four well defined germ-line encoded amino acid sequence substitutions (VHH tetrad) present in camelid VHH domains but not in soluble VH domains. These are all present in the second framework region and function to reduce the hydrophobicity of the former light chain interface. Glu-44 and Arg-45 are found in place of the less hydrophilic Gly-44 and Leu-45 present in VH domains, whilst the hydrophilicity at position 47 is increased by the substitution of Trp with smaller residues. The fourth change requires the replacement of Val-37 by Phe or Tyr.

The Heavy Chain Constant Region

Operationally, a heavy chain constant region is encoded by a naturally occurring or engineered gene segment that is capable of recombining with a V gene segment, a D gene segment and a J gene segment in a B cell. Preferably the heavy chain constant region is derived from an antibody locus.

Each heavy chain constant region essentially comprises at least one heavy chain constant region gene, which is expressed without a functional CH1 domain so that generation of heavy chain-only antibody can occur. In the absence of endogenous immunoglobulin light chain gene expression, then the heavy chain constant region may comprise CH1 functionality which may be spontaneously deleted at low frequency during heavy chain gene expression. Each heavy chain constant region may also comprise one or more additional heavy chain constant region exons, which are selected from the group consisting of Cδ, Cγ1-4, Cμ, Cε and Cα1-2. The heavy chain constant region gene segments are selected depending on the preferred class or mixture of antibody classes required. Optionally, the heterologous heavy chain locus is Cμ- and Cδ-deficient.

For instance, the expression of all or part of a heterologous heavy chain Cγ locus devoid of CH1 will produce optionally some or all IgG isotypes, dependent on the IgG1, IgG2, IgG3 and IgG4 isotypes present in the heterologous IgG locus.

Alternatively, selected mixtures of antibodies may be obtained. For example, IgA and IgM may be obtained when the heavy chain constant region comprises a Cα and a Cμ gene.

The heavy chain constant region present in the transgenic locus may be of human origin, but may be the same as or closely related to that of the host mammal so as to maximise antigen responses in vivo. Thus, for the derivation of heavy chain—only antibodies or soluble VH domains to be used for therapeutic applications in humans, the VDJ genes present in the locus will be derived from human germ-line sequences, optionally modified, and the constant regions may be of rodent origin if the host animal is a rodent for example a mouse. Selected heavy chain-only antibodies comprising soluble human VH binding domains and rodent constant effector regions may then be cloned, and the rodent effector regions replaced by human constant effector regions of choice, or the soluble VH domain used to derived alternative VH fusion proteins, VH domain antibody complexes and the like.

Where the heavy chain-only antibodies are to be used for veterinary or alternative purposes, the V, D and J gene segments are preferably derived from the vertebrate or mammal best suited to the intended purpose. For example, V gene segments and D and J gene segments may be derived from other mammals (e.g. mouse, rat, pig, cow, goat, sheep, camel etc) dependent on the intended use, e.g. veterinary, industrial, agricultural, diagnostic or reagent applications.

A 'heavy chain constant region exon' ('CH exon') as herein defined includes the sequences of naturally occurring vertebrate, but especially mammalian, CH exons. This varies in a class specific manner For example, IgG and IgA are naturally devoid of a CH4 domain. The term 'CH exon' also includes within its scope derivatives, homologues and fragments thereof in so far as the CH exon is able to form a functional heavy chain-only antibody as herein defined when it is a component of a heavy chain constant region.

Mammals

The transgenic mammal used in the methods of the invention is not a human. The transgenic mammal is preferably a rodent such as a rabbit, guinea pig, rat or mouse. Mice and rats are especially preferred. Alternative mammals, such as goats, pigs, cattle, sheep, cats, dogs or other animals, may also be employed.

Preferably, transgenic animals comprising heterologous heavy chain-only antibody loci integrated in the germ-line are generated using established oocyte injection technology and, where established, ES cell technology, iPS cell technology or nuclear transfer (cloning) technology. Alternatively, the loci may be introduced into the above cells or directly into fertilised eggs using zinc finger nucleases (Remy et al. (2009) Transgenic Res., 2009 Sep. 26. [Epub ahead of print], Kandavelou et al. (2009) Biochem. Biophys. Res. Commun.; 388, (1), 56-61) or recombination enzyme technology (e.g. Sakurai et al. (2010) Nucleic Acids Res., January 13 [Epub ahead of print] and references therein) such as cre etc.

Standard homologous recombination in ES cells may also be used to eliminate CH1 functionality from endogenous heavy chain genes and to replace elements or sequences within endogenous V genes segments or D and J gene segments, resulting in the production of heavy chain-only antibodies from the endogenous heavy chain loci.

Advantageously, heterologous heavy chain-only gene loci transgene expression is enhanced, where antibody heavy loci endogenous to the mammal are deleted or silenced or have a reduced capacity to produce endogenous antibodies. Where the endogenous host heavy chain loci have been engineered to eliminate CH1 functionality, and VDJ and optionally the constant effector regions replaced by sequence from other species, preferably human, then the addition of further transgenic heavy chain loci is unnecessary.

This approach of generating heavy chain-only antibodies and soluble VH domains as described above maybe of particular use in the generation of soluble antibodies and antibody complexes free of aggregates for human therapeutic use. Therefore, in a further aspect, the present invention provides a transgenic mammal expressing a heterologous heavy chain locus according to the present invention in response to antigen challenge.

Antibody-producing cells may be derived from transgenic animals according to the present invention and used, for example, in the preferred embodiment, for the recovery of memory cells or long-lived plasma cells, but also for the production of heavy chain-only antibodies from hybridomas or by array approaches as herein defined. In addition or alternatively, nucleic acid sequences encoding heavy chain-only antibodies and/or soluble VH domains may be isolated from B-cells, especially memory cells or long-lived plasma cells, of transgenic mammals according to the present invention following antigen challenge and used to produce soluble VH domain heavy chain-only antibodies, soluble bi-specific/bi-functional VH domain complexes, or soluble VH domain polyproteins (see WO 99/23221) using recombinant DNA techniques which are familiar to those skilled in the art.

Alternatively or in addition, polyclonal antigen-specific heavy chain-only antibodies may be generated by immunisation of a transgenic animal according to the present invention.

Thus, in a further aspect, the present invention provides a method for the production of high affinity heavy chain-only antibodies by immunising a transgenic mammal according to the present invention with an antigen.

In a preferred embodiment of this aspect of the invention, the mammal is a rodent, preferably a mouse or a rat.

Production of Heavy Chain-Only Antibodies and Soluble VH Domain Fusion Proteins

Production systems for heavy chain-only antibodies and soluble VH domain fusion proteins include mammalian cells in culture (e.g. CHO cells), plants (e.g. maize), transgenic goats, rabbits, cattle, sheep, chickens and insect larvae suited to mass rearing technology. Other production systems, including virus infection (e.g. baculovirus in insect larvae and cell-lines) are alternatives to cell culture and germ-line approaches. Other production methods will also be familiar to those skilled in the art. Where there is a requirement for heavy chain-only IgA or IgM assembly, the co-expression of a "J chain" maybe beneficial. Suitable methods for the production of heavy chain-only antibody or soluble VH binding domains alone, or VH binding domain complexes are known in the art. For example, VH binding domains and VH binding domain complexes have been produced in bacterial systems and heavy chain-only homodimers have been produced in hybridomas and transfected mammalian cells (see Reichmann and Muyldermans, (1999) J. Immunol. Methods, 231, 25-38).

Methods are also well established for the expression of engineered human VH binding domains derived using phage display technology (Tanha et al. (2001) J. Biol. Chem., 276, 24774-24789 and references therein).

The present invention also provides a polynucleotide sequence consisting of the heterologous heavy chain locus, an isolated polynucleotide encoding a heavy chain-only antibody of the invention and a vector comprising a heterologous heavy chain locus, or fragment thereof, or isolated polynucleotide encoding a heavy chain-only antibody according to the present invention. The invention also provides for polynucleotide sequences encoding soluble VH domains and VH domain fusion proteins and a vector comprising such sequences.

The present invention also provides a host cell transformed with a heterologous heavy chain-only locus, or fragment thereof, or isolated polynucleotide encoding the heavy chain-only antibody, soluble VH domain, or VH domain fusion protein according to the present invention.

Uses of the Heavy Chain-Only Antibodies, Soluble VH Domains, and VH Domain Polypeptide Complexes and Polyproteins of the Invention The soluble high affinity heavy chain-only antibodies, VH domain fusion proteins, VH domains polypeptide complexes and soluble VH domains of the present invention are particularly suited to use as both parenteral and non-parenteral medicines. Within the context of the invention, preferably these are entirely of human origin, but optionally and less preferentially may comprise V, D or J gene segments from other species.

The enhanced solubility of heavy chain-only antibodies comprising soluble VH domains, isolated soluble VH domains and soluble VH domain binding complexes and polyproteins of the invention are especially suited to use as reagents, and diagnostics in addition to therapy.

All are suitable for pharmaceutical use in humans, and so the invention provides a pharmaceutical composition comprising a heavy chain-only antibody comprising soluble VH domains, isolated soluble VH domains, soluble VH domain binding complexes or soluble VH domain polyproteins. The invention also provides the use of a heavy chain-only antibody comprising soluble VH domains, isolated soluble VH domains, soluble VH domain binding complexes or soluble VH domain polyproteins of the present invention in the preparation of a medicament for the prophylaxis and/or treatment of disease.

The pharmaceutical compositions and medicaments will typically be formulated before administration to patients.

For example, a heavy chain-only antibody comprising soluble VH domains, isolated soluble VH domains, soluble VH domain binding complexes or soluble VH domain polyproteins may be mixed with stabilisers, particularly if they are to be lyophilised. Addition of sugars (e g mannitol, sucrose or trehalose) is typical to give stability during lyophilisation, and a preferred stabiliser is mannitol. Human serum albumin (preferably recombinant) can also be added as a stabiliser. Mixtures of sugars can also be used, e.g. sucrose and mannitol, trehalose and mannitol, etc.

Buffer may be added to the composition, e.g. a Tris buffer, a histidine buffer, a glycine buffer or, preferably, a phosphate buffer (e.g. containing sodium dihydrogen phosphate and disodium hydrogen phosphate). Addition of buffer to give a pH between 7.2 and 7.8 is preferred, and in particular a pH of about 7.5.

For reconstitution after lyophilisation, sterile water for injection may be used. It is also possible to reconstitute a lyophilised cake with an aqueous composition comprising human serum albumin (preferably recombinant).

Generally, the heavy chain-only antibody comprising soluble VH domains, isolated soluble VH domains, soluble VH domain binding complexes or soluble VH domain polyproteins will be utilised in purified form together with pharmacologically appropriate carriers.

The invention thus provides a method for treating a patient, comprising administering a pharmaceutical composition of the invention to the patient. The patient is preferably a human, and may be a child (e.g. a toddler or infant), a teenager or an adult, but will generally be an adult.

The invention also provides a heavy chain-only antibody comprising soluble VH domains, isolated soluble VH domains, soluble VH domain binding complexes and soluble VH domain polyproteins of the invention for use as a medicament.

The invention also provides the use of heavy chain-only antibodies comprising soluble VH domains, isolated soluble VH domains, soluble VH domain binding complexes and soluble VH domain polyproteins of the invention in the manufacture of a medicament for treating a patient.

These uses, methods and medicaments are preferably for the treatment of diseases or disorders which include but are not limited to: wound healing, cell proliferative disorders, including neoplasm, melanoma, lung, colorectal, osteosarcoma, rectal, ovarian, sarcoma, cervical, oesophageal, breast, pancreas, bladder, head and neck and other solid tumours; myeloproliferative disorders, such as leukemia, non-Hodgkin lymphoma, leukopenia, thrombocytopenia, angiogenesis disorder, Kaposis' sarcoma; autoimmune/inflammatory disorders, including allergy, inflammatory bowel disease, arthritis, psoriasis and respiratory tract inflammation, asthma, immunodisorders and organ transplant rejection; cardiovascular and vascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; developmental disorders; metabolic disorders including diabetes mellitus, osteoporosis, and obesity, AIDS and renal disease; infections including viral infection, bacterial infection, fungal infection and parasitic infection, pathological conditions associated with the placenta and other pathological conditions and for use in immunotherapy.

In a further aspect still, the present invention provides the use of a heavy chain-only antibody comprising soluble VH domains, isolated soluble VH domains, soluble VH domain binding complexes or soluble VH domain polyproteins of the present invention as a diagnostic, prognostic, or therapeutic imaging agent alone or in combination with suitable effector agents.

The present invention provides the use of a heavy chain-only antibody comprising soluble VH domains, isolated soluble VH domains, soluble VH domain binding complexes or soluble VH domain polyproteins as herein described as an intracellular binding reagent, or an abzyme. Preferred are antigen-specific soluble VH binding domains, soluble VH domain binding complexes and soluble VH domain polyproteins.

The present invention also provides the use of an antigen-specific heavy chain-only antibody or soluble VH binding domain according to the present invention as an enzyme inhibitor or receptor blocker. Preferred heavy chain-only antibody fragments are antigen-specific soluble VH binding domains.

The present invention also provides the use of one or more soluble VH domains fused to an effector molecule for use as a therapeutic, imaging agent, diagnostic, abzyme or reagent.

The invention is now described, by way of example only, in the following detailed description which refers to the following figures.

BRIEF DESCRIPTION OF THE DRAWINGS

FIG. 3. Elisa (top) and western blot (bottom) of the Luk-sPV immunised serum (V4 compared to wt normal mice) and a western blot of individually isolated VH domains using gel electrophoresis of the Luk-sPV protein, blotting it and detection with the various positive clones from the phage display screen.

FIG. 4. Example of two VH domain sequences after immunisation with Luks-PV, showing that both IgG2 and IgG3 are produced (class switching) and that the same VDJ rearrangement results in different mutations. FIG. 4 lists SEQ ID NOS: 3-6, from top to bottom.

FIG. 5. VH domain sequences derived using the V3-23 gene segment after immunisation with human CR1, showing that both IgG2 and IgG3 are produced (class switching) and that the same VDJ rearrangement results in different mutations, when compared to the germline sequence of the V3-23 segment shown on top. Parts of the sequences were obtained via hybridomas, the remainder via display libraries. FIG. 5 lists SEQ ID NOS:7-30, from top to bottom.

FIG. 6. VH domain sequences derived using the V3-11 gene segment after immunisation with human CR1, showing that both IgG2 and IgG3 are produced (class switching) and that the same VDJ rearrangement results in different mutations, when compared to the gem-line sequence of the V3-11 segment shown on top. Parts of the sequences were obtained via hybridomas (arrows), the remainder via display libraries. FIG. 6 lists SEQ ID NOS:31-56, from top to bottom.

FIG. 10. Solubility of a number of anti CR1 VH domains.

FIG. 11. Massive parallel sequencing to determine preferred mutations identifying sequence HVH3-23 (SEQ ID NO:3).

EXAMPLE 1

Generation of Anti Luk-sFV Antibodies

Figure 1:
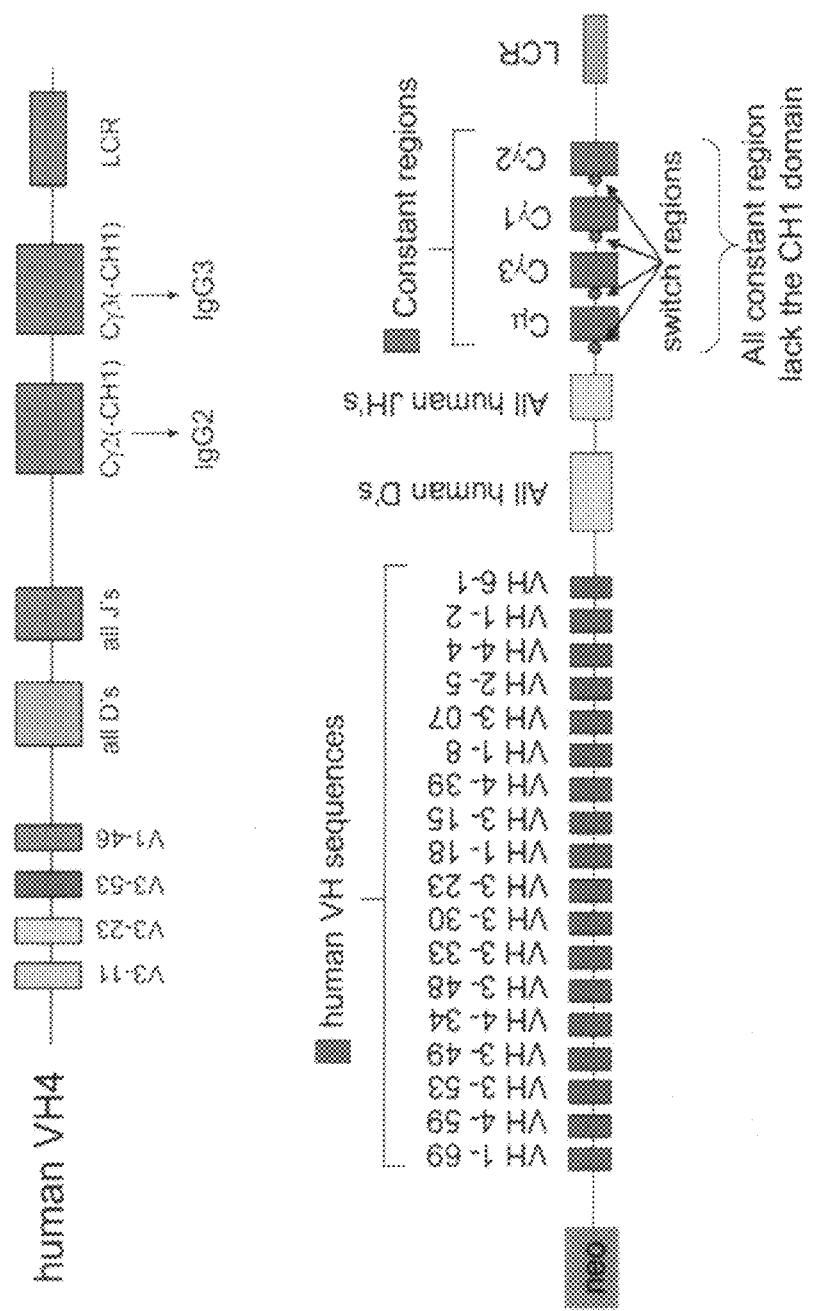
FIG. 1. Two human heavy chain-only immunoglobulin loci one carrying 4 VH gene segments the other carrying 18 VH gene segments. The loci comprising 18 VH gene segments comprises mouse constant effector regions (—CH1) cover more than 90% of the VH gene segment usage in normal human tetravalent antibodies.

Immunisation with the Luks-PV protein from Staph A is carried out in transgenic mice containing a completely human heavy chain antibody locus as described in WO2006/008548. These mice carry 4 human VH segments, all of the human heavy chain D regions, all of the human JH regions and the human Cγ2 and Cγ3 regions (FIG. 1).

Figure 2:
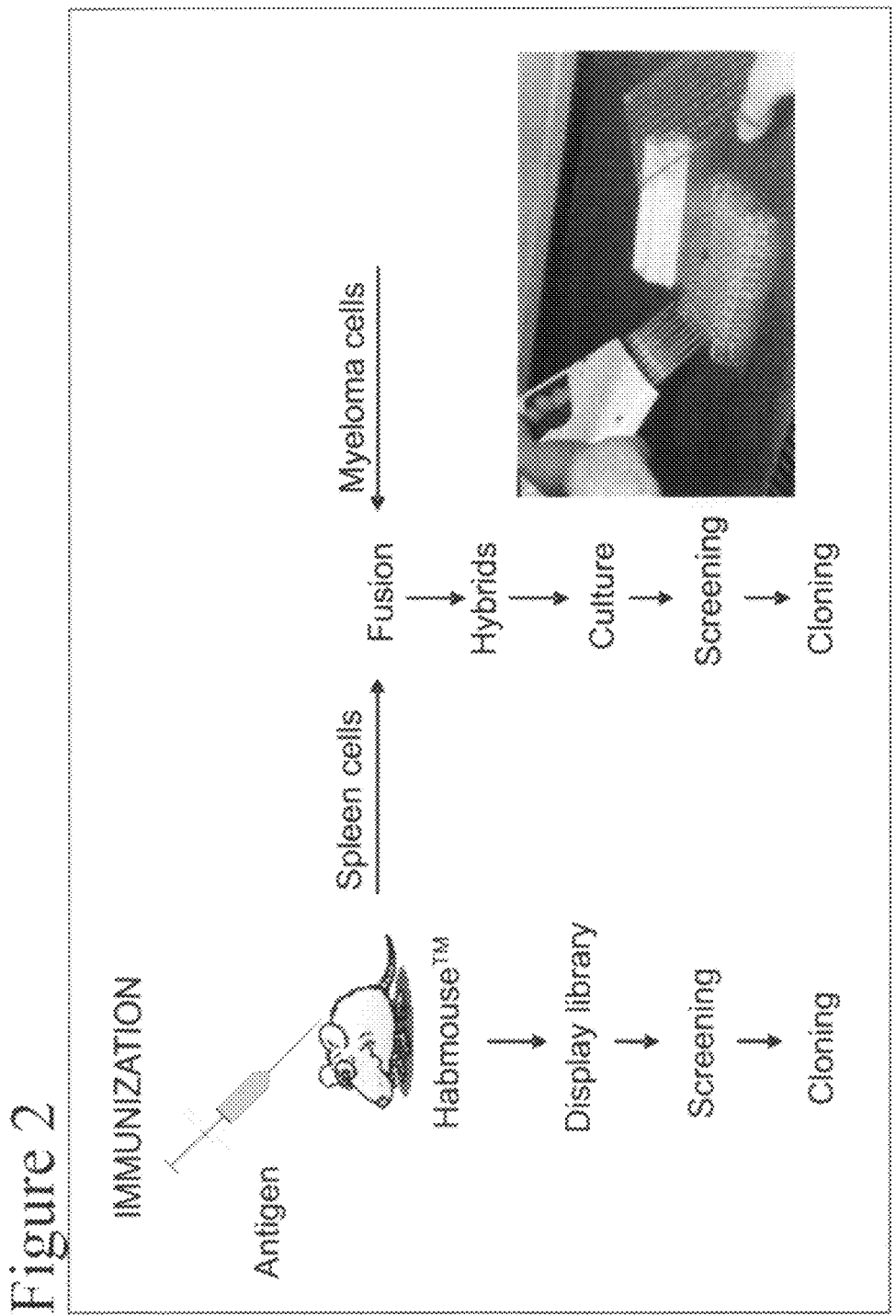
FIG. 2. Immunisation and isolation protocol for human VH domain by phage display or human heavy chain-only antibodies by standard hybridoma technology.

The CH1 domains have been deleted from the human Cγ constant regions to allow the production of human heavy chain-only antibodies as described (Janssens et al (2006) PNAS, 103, 15130-15135). The mice are immunised using standard protocols and the antibodies are isolated as schematically shown in FIG. 2.

Figure 3:
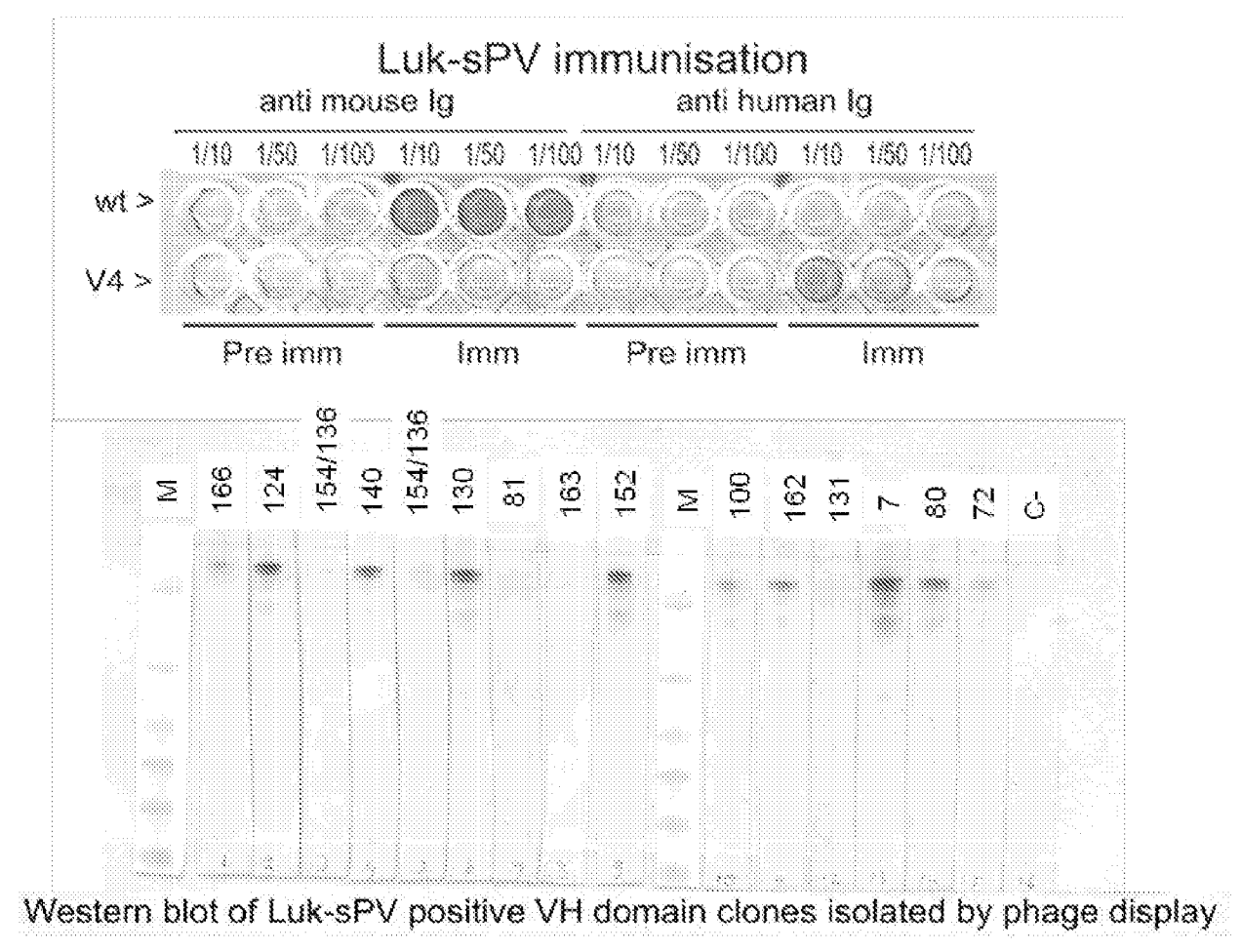

The mice are immunised four times by standard protocols and the serum checked for a positive response by standard ELISA (FIG. 3).

After immunisation, the spleen cells are collected and the mRNA reverse transcribed and amplified into cDNA with VH domain-specific primers by standard methods (see e.g. Janssens et al (2006) PNAS, 103, 15130-15135). The resulting VH fragments are cloned into a phage display vector. After 3 rounds of screening and panning by standard display protocols, the VH domains (VH-D-J) are cloned into a bacterial expression vector. Positive clones are confirmed by Western blotting and the cloned DNA is subsequently sequenced by standard methods, resulting in amino acid sequence definition of the VH domain regions shown in FIG. 4.

Alternatively, the antibodies can be obtained by standard hybridoma technology. The VH domains obtained by phage display technology can be engineered back onto a heavy chain constant effector region of choice (devoid of CH1 functionality) by standard cloning methods to produce a full heavy chain-only antibody of choice in terms of the constant region (e.g. Cα rather than Cγ). Similarly, heavy chain-only antibodies obtained by hybridoma technology can be cloned out by standard cDNA and PCR technology. This allows the isolation of VH domains alone.

Thus, both approaches can be used to derive antigen-specific VH domains or antigen-specific heavy chain-only antibodies.

EXAMPLE 2

Generation of Anti Human CR1 Antibodies

Example 2 is very similar to Example 1 except that the immunisation is carried out with CR1 as the antigen, a protein that is normally expressed on the surface of human red blood cells. The immunisation was also carried out by injection of murine red blood cells that express human CR1 on their cell surface. The result of the different immunisations is very similar. Immunisation is carried out in transgenic mice containing a completely human heavy chain antibody locus as described in WO 2006/008548. These mice carry 4 human VH segments, all of the human heavy chain D regions all of the JH regions and the human Cγ2 and Cγ3 regions (FIG. 1).

The CH1 regions have been deleted from the human Cγ constant regions to allow the production of human heavy chain-only antibodies as described (Janssens et al (2006)

PNAS, 103, 15130-15135). The mice are immunised using standard protocols and the antibodies are isolated as schematically shown in FIG. 2.

After immunisation the spleen cells are collected and the mRNA reversed transcribed and amplified into cDNA with VH domain specific primers by standard methods (e.g (Janssens et al (2006) PNAS, 103, 15130-15135). The resulting VH fragments are cloned into a phage display vector. After 3 rounds of screening and panning by standard display protocols, the VH domains (VH-D-J) are cloned into a bacterial expression vector. The cloned sequence is subsequently sequenced by standard methods, resulting in the VH domain region shown in FIGS. 5 and 6. Alternatively, the antibodies can be obtained by standard hybridoma technology (FIGS. 5 and 6). The VH domains obtained by phage display technology can be engineered back onto a constant effector region of choice (devoid of CH1 functionality) by standard cloning methods to produce a full heavy chain-only antibody (e.g. Cα rather than Cγ). Similarly, the heavy chain-only antibody obtained by hybridoma technology can be cloned out by standard cDNA and PCR technology which allows the isolation of its VH domain only. Thus, both approaches can be used to derive antigen-specific VH domains or antigen-specific heavy chain-only antibodies.

EXAMPLE 3

Figure 7:
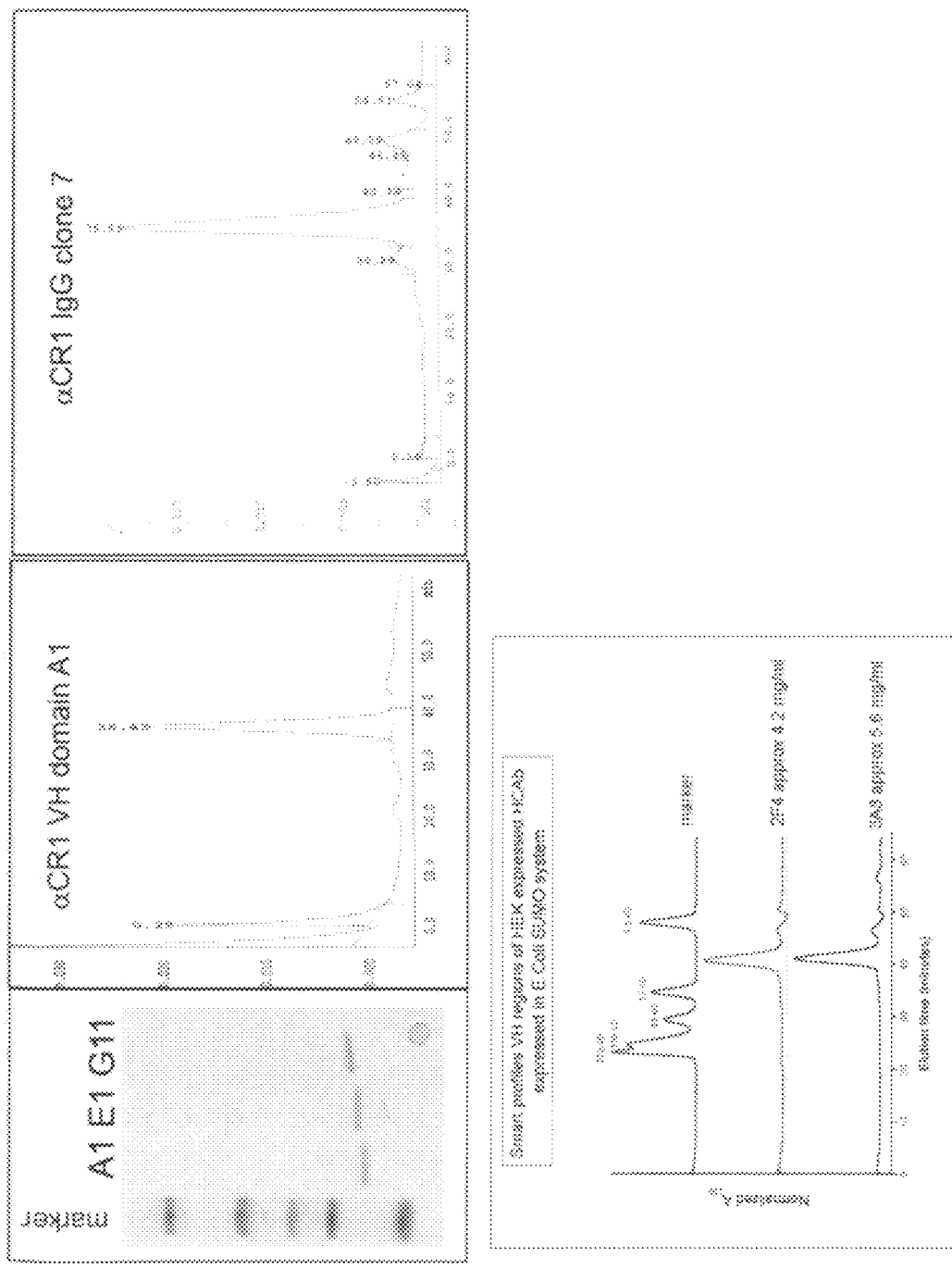
FIG. 7. Example of gel electrophoresis (left) of VH domains (αCR1) after purification and expression in the SUMO hybrid protein system (InVitrogen). The example shows three different length VH domains of the correct molecular weight. The marker lane is on the left. The middle panel shows the elution profile of VH domains on a Sephadex 75 Smart system. The panel on the right is the same but for a complete heavy chain-only IgG on a Sephadex 200. The bottom panel shows the elution profiles of two other VH domains concentrated to >4 mg/ml.

Expression of VH Domains and Heavy Chain-Only Antibodies, Affinity and Solubility The VH domains of Examples 1 and 2 can be expressed in a bacterial expression system to obtain large quantities of purified VH domains. For example, the VH domain can be expressed as hybrid protein in bacteria using the SUMO hybrid expression system (InVitrogen). When purified, these run as a single fragment on denaturing gel electrophoresis gels (FIG. 7). When run on a Smart Sephadex chromatography system under non-denaturing condition, these VH domains run predominantly as a single main peak of the correct molecular weight (FIG. 7), with little evidence of soluble aggregates.

Heavy chain-only antibody derived from hybridoma supernatants also run predominantly as a single main peak, with evidence of a small percentage of antibody dimer at the leading edge of the peak.

Figure 8:
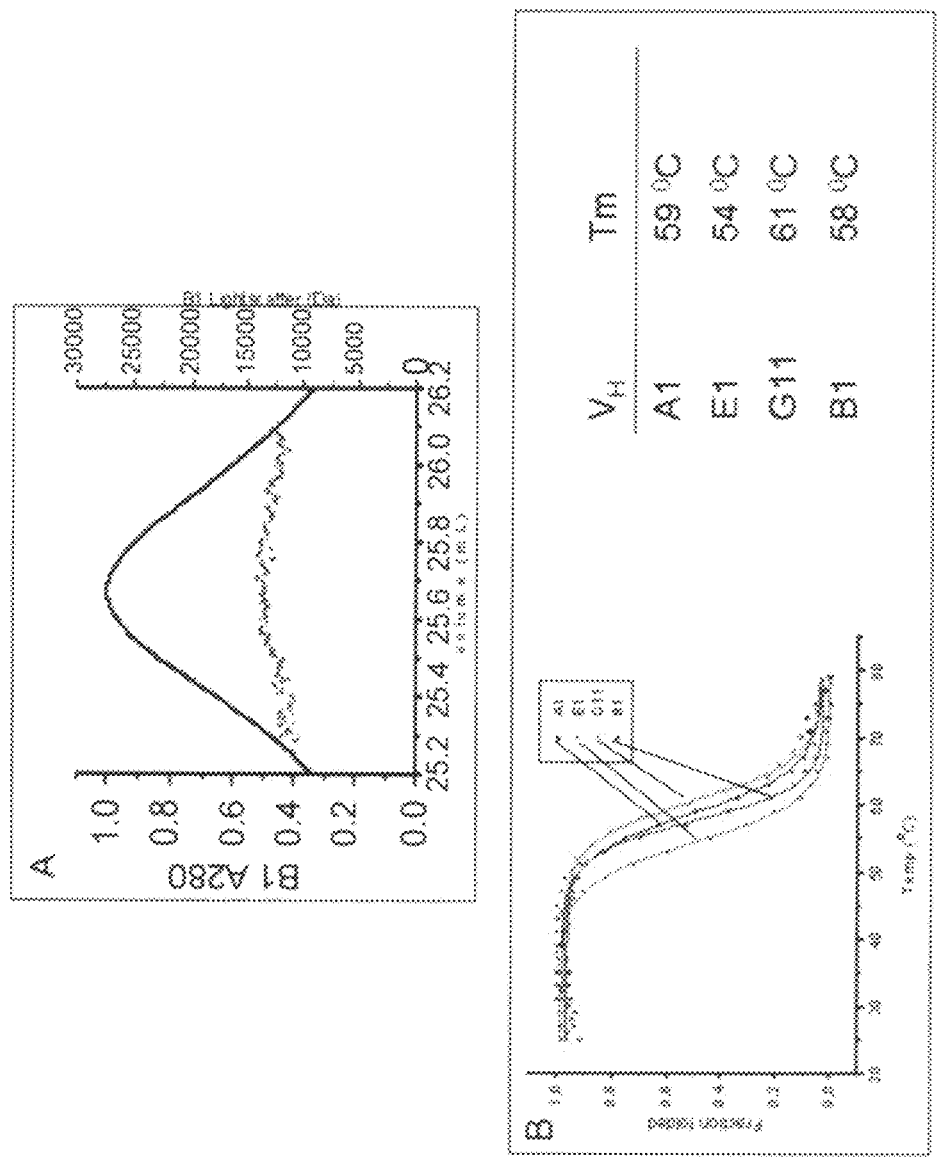
FIGS. 8a and b. A. Light scattering plot and B. Thermal stability of VH domains.

The single peak of the VH domains suggests that they are soluble monomers, which was confirmed by running scatter plots (FIG. 8A), because the peak of light scattering coincides with the peak of protein absorption during the run. Finally, when heated, the VH domains are stable up to 55° C. as measured by standard Circular Dichroism analysis (FIG. 8B).

Figure 9:
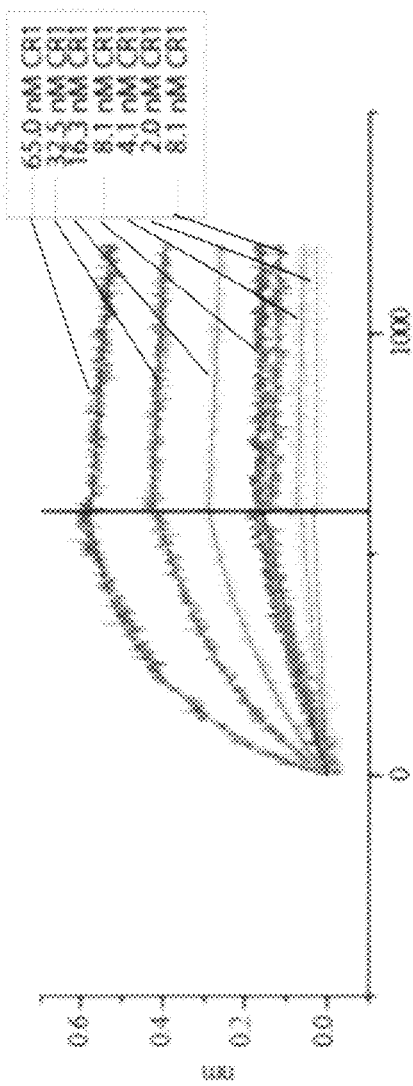
FIG. 9. Affinity measurements of a number of αCR1 heavy chain-only antibodies (left) and the binding and dissociation profiles of one of the antibodies on an Octet system to obtain the binding affinity.

Finally the soluble VH domains and HCAbs were for tested for their binding affinity using a BiaCore and an Octet system. Affinities obtained were in the low nanomolar range or better (FIG. 9).

A number of the VH domains derived from HCAbs were also concentrated by vacuum centrifugation and colloidal matter removed by high speed centrifugation. This yielded solubility numbers which are a minimum estimate because the small quantities of sample prevented further concentration. All the VH domains tested showed solubility in excess of 4 mg/ml (FIG. 10).

EXAMPLE 4

Mass Sequencing to Determine the Mutation Patterns

From an inspection of all the sequences collected from the antibodies binding Luk-sPV, CR1 and other antigens, it became apparent that the VDJ recombination and maturation (hypermutation) of soluble human VH domains derived from HCAb transgenes expressed in murine B-cells was very different from that observed in camel and llama VHH domains, or human VH domains derived from normal tetrameric heavy and light chain antibodies. A massive parallel sequencing (Roche 454 sequencing) was therefore carried out to follow the process from recombination to hypermutation. This was used to verify that the process is indeed different, and to understand which parameters and part(s) of the antibody are important for the generation of a high affinity, soluble human heavy chain-only antibody following the initial choice of a particular VDJ recombination. The results provide an overview of how the process takes place (FIG. 11).

This analysis shows that the mouse is capable of introducing a large variety of amino acid substitutions across the VH domain of the expressed transgene. The bulk are at the position of CDR1 and CDR2. However, substitutions are also apparent within FR1 and FR2 and distributed across FR3. CDR/FR interface regions appeared as hot spots for substitutions. From this analysis, it is clear that the mutation process, in terms of positions and the amino-acid substitutions, is very different from that seen in camelid VHH domains and VH domains present in normal tetrameric human antibodies.

EXAMPLE 5

Comparative Analysis of the Individual Framework and CDR Regions Present in Soluble VH Domains, VHH Domains and VH Domains Derived from Tetrameric Antibodies All mutations of the soluble human antigen-binding VH domains were tabulated and the different regions (FR1, CDR1, FR2, CDR2, FR3, CDR3) analysed in comparison to VHH domains from camelid heavy chain-only antibodies, llama heavy chain-only antibodies and human VH domains obtained from normal tetrameric human antibodies.

This comparison comprised 10 known camel VHH domain sequences, 58 known llama VHH domain sequences and more than 4000 known human VH domain sequences derived from normal tetrameric antibodies, all obtained from the literature and public antibody databases.

The FR1 region of the soluble human VH domains (FIG. 12) shows an increase in the net charge when compared to camel and llama and an increase in hydrophobicity when compared to camel, llama and VH domains derived from normal human tetrameric antibodies, while the number of charged amino acids has increased.

The CDR1 region (FIG. 12) has very little change in net charge (some decrease compared to llama) and an increase in hydrophobicity relative to the equivalent VH domain from human tetrameric antibodies, llama and camel VHH domains. The number of charged amino acids shows little significant difference.

The FR2 region of the soluble human VH domain (FIG. 13) shows no difference in the net charge when compared to camel and llama VHH domains and a substantial increase in hydrophobicity when compared to camel and llama VHH domains, while the number of charged amino acids has decreased compared to camel and llama VHH domains. In both aspects, it is similar to human VH domains derived from tetrameric antibodies. The CDR2 region (FIG. 13) has a similar net charge to llama, which is higher than camel and human tetrameric antibodies, and very similar hydrophobicity to the others, while the number of charged amino acids is similar to human VH domains derived from tetrameric antibodies but somewhat lower than the others.

Figure 14:
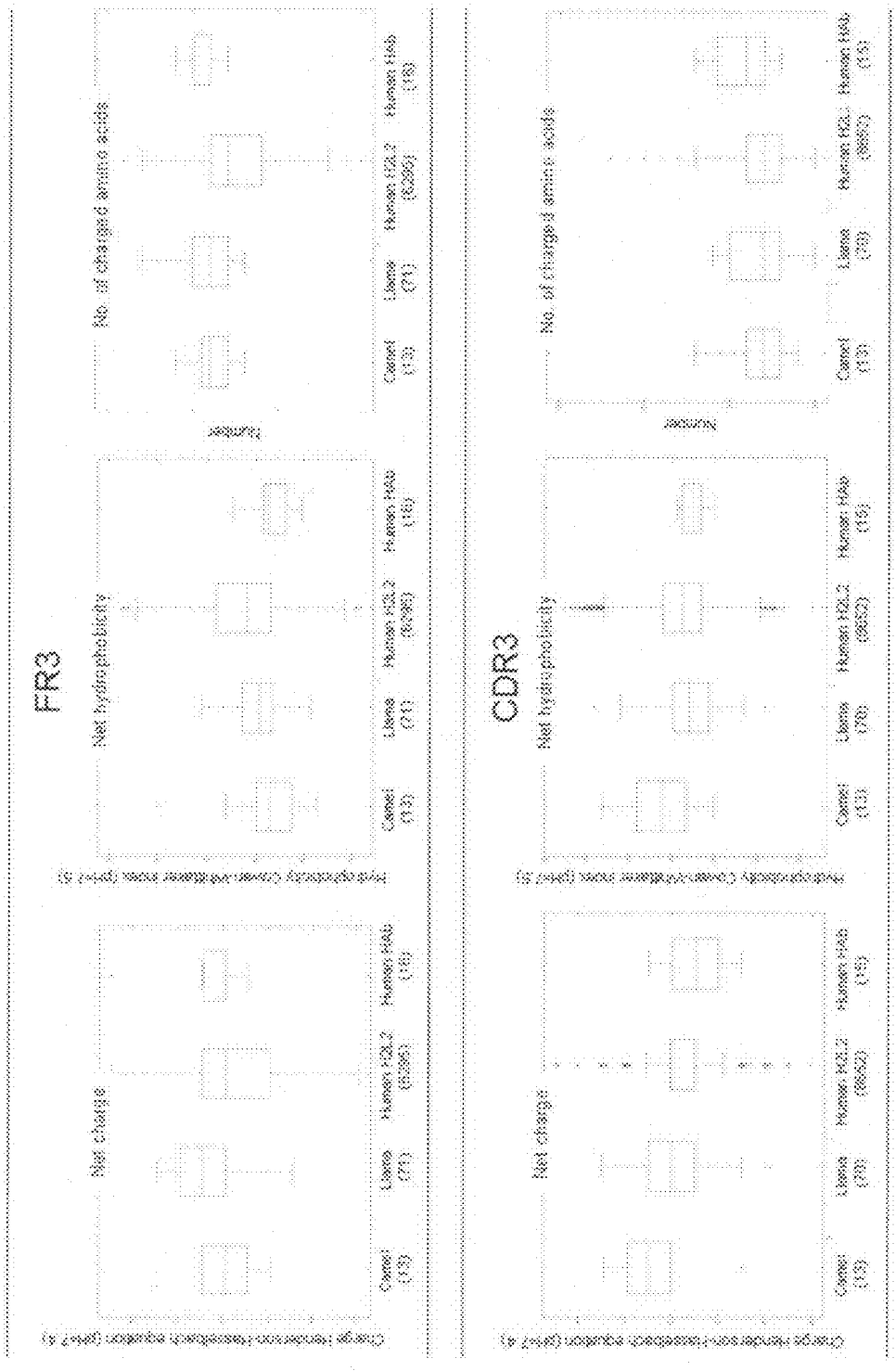
FIG. 14. Box-plot analysis of the framework 3 (FR3) and CDR3 regions of human heavy chain-only antibodies (HCAb) compared to the same regions from camel, llama and human heavy chains from normal tetrameric heavy/light chain antibodies. Net charge was determined by the Henderson-Hasselbach equation at pH=7.4; net hydrophobicity was determined by the Cowan-Whittaker index at pH=7.5. The numbers below the different antibodies are the number of unique input sequences.

The FR3 region of the soluble human VH domain (FIG. 14) shows an increase in net charge when compared to human VH domains derived from tetrameric antibodies and a decrease in hydrophobicity when compared to human VH domains derived from tetrameric antibodies, while the number of charged amino acids has increased compared to human VH domains derived from tetrameric antibodies. In all aspects, it is similar to camel and llama VHH domains. The CDR3 region of the soluble human VH domains (FIG. 14) have a decreased net charge relative to the llama and camelid VHH domains and human VH domains derived from tetrameric antibodies, whilst the number of charged amino acids is increased when compared to all others. The CDR3 region of soluble human VH domains has a very similar hydrophobicity to llama VHH, but lower than that observed in VH domains present in normal human tetrameric antibodies and normal camel tetravalent antibodies.

The results show that, of the initial VDJ recombination, there is selection of recombination events with a higher number of charged amino acids when compared to human tetrameric (CDR3) antibodies. This is followed by affinity maturation in the CDR1 and CDR2 regions and in all three framework regions (FR1, FR2, FR3). This results in human heavy chain-only antibodies with soluble VH domains which have an increase in hydrophobicity in FR1, but a decrease in FR3 when compared to VH domains derived from human tetrameric antibodies. There is very little difference in FR2 or the CDR1 and CDR2 regions. The overall pattern therefore shows that hydrophobicity is spread differently across the soluble VH domain (shifted towards FR1 and away from FR3 and CDR3) relative to VH domains derived from tetrameric antibodies which are less soluble and have a tendency to aggregate. This analysis does not show whether particular mutations are made in particular positions or regions of the VH domain (see Example 6), but that there are features relating to charge distribution and hydrophobicity across the soluble human VH domains which distinguishes them from llama and camelid VHH domains and human VH domains derived from tetrameric antibodies.

EXAMPLE 6

3D Structures

Figure 15:
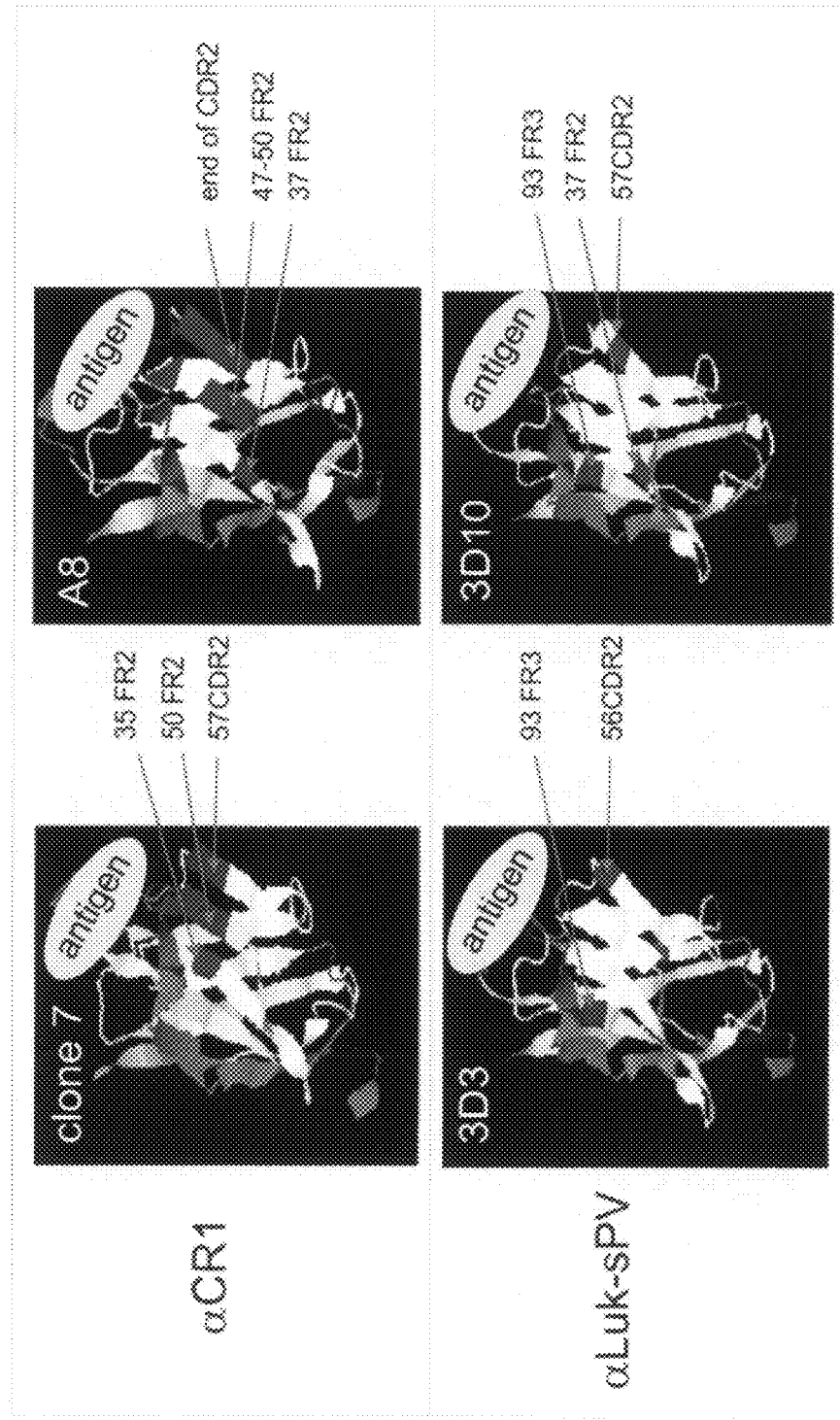
FIG. 15. 3D structure of VH domains binding either human CR1 or staph. A Luk-sPV. The antigen-binding site is in the top right position and the former VL interaction domain is facing the reader. The amino acid changes are indicated by colour in the 3D structure.

The analysis of Example 4 indicated that the changes in the framework regions (FR1, FR2, FR3) of the soluble human VH domain after an initial VDJ rearrangement were largely focussed on particular positions when placed on the three dimensional structure of a human VH domain derived from a tetrameric antibody (FIG. 15).

In the soluble human VH domain, FR1 mutations were seen from amino acids 13-18, with a prevalence for a change at position 13, resulting in increased hydrophobicity, even though the number of charged amino acids, but not the net charge, is increased. Importantly, the changes around position 13 are located in a small loop that is increased in hydrophilicity, presumably increasing solubility.

In FR2 of soluble human VH domains, there is a clear focus around position 35 and one around position 50, without an overall change in hydrophobicity when compared to VH domains derived from human tetrameric antibodies.

The changes in FR3 of the soluble VH domains relative to VH domains derived from human tetrameric antibodies coincide with the end of the CDR2 region and the region around the very end of FR3 (immediately next to CDR3).

Figure 16:
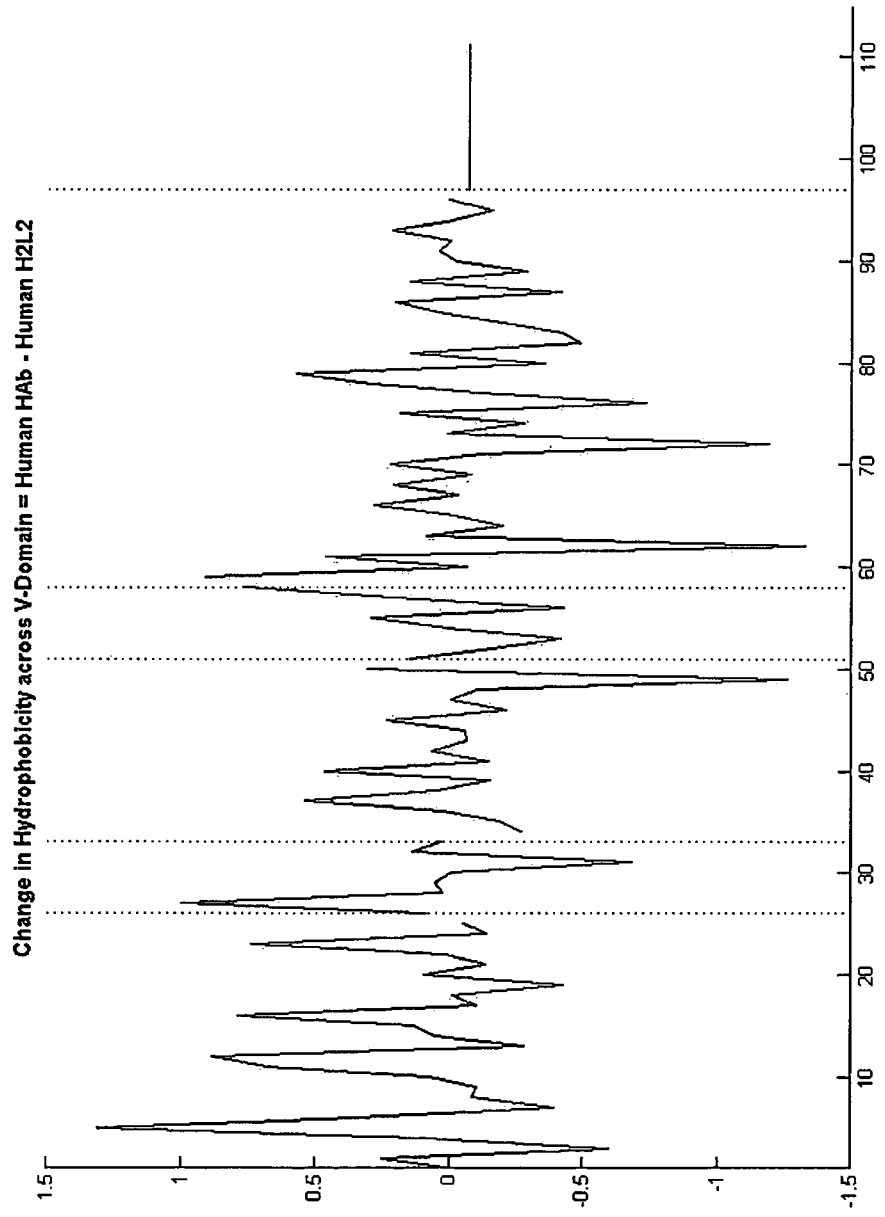
FIG. 16. Differences in average hydrophobicity at each position of the VH domain (except CDR3) indicating a shift towards more hydrophobicity in the heavy chain-only antibodies, in particular in the N terminus of the VH domain. A number of hotspots in terms of hydrophobicity differences are apparent at positions 49, 62 and 72 compared with the average human tetrameric VH.

When these changes observed in soluble human VH domains derived from HCAbs are superimposed on the 3D structure of the VH domain, it is immediately apparent that the FR2 mutations occur in the β-pleated sheets that normally make up the interaction surface of VH with the VL domain in tetrameric antibodies. In FR1, the changes also result in a more hydrophobic domain. The results suggest that the N-terminal half of the VH domain has an increased hydrophobicity to increase the stability/solubility of the VH domain and compensate for the absence of light chain. In contrast, the C terminal half is less hydrophobic. The most important changes are a "redistribution" of the hydrophobicity pattern (N terminus more hydrophobic, C terminus less hydrophobic, FIG. 16) and framework mutations that affect the former light chain interface.

The overall shift in hydrophobicity and changes in specific motifs carried out by the mouse immune system allow for the generation of high affinity, soluble heavy chain-only antibodies and soluble VH domains with structural features which distinguish them from VH domains prone to aggregation derived from human tetrameric antibodies.

EXAMPLE 7

Generation and Expression Cloning of Human Anti HA Antibodies

The immunisation procedures used in Example 7 are as described in Examples 1 and 2 except that the immunisation is carried out with influenza HA (H3N2) as the antigen Immunisation is carried out by injection of the protein into transgenic mice comprising a completely human heavy chain antibody locus as described in Janssens et al (2006) PNAS, 103, 15130-15135. These mice carry 4 human VH segments, all of the human heavy chain D regions, all of the JH regions and the human Cγ2 and Cγ3 regions (FIG. 1).

Figure 17:
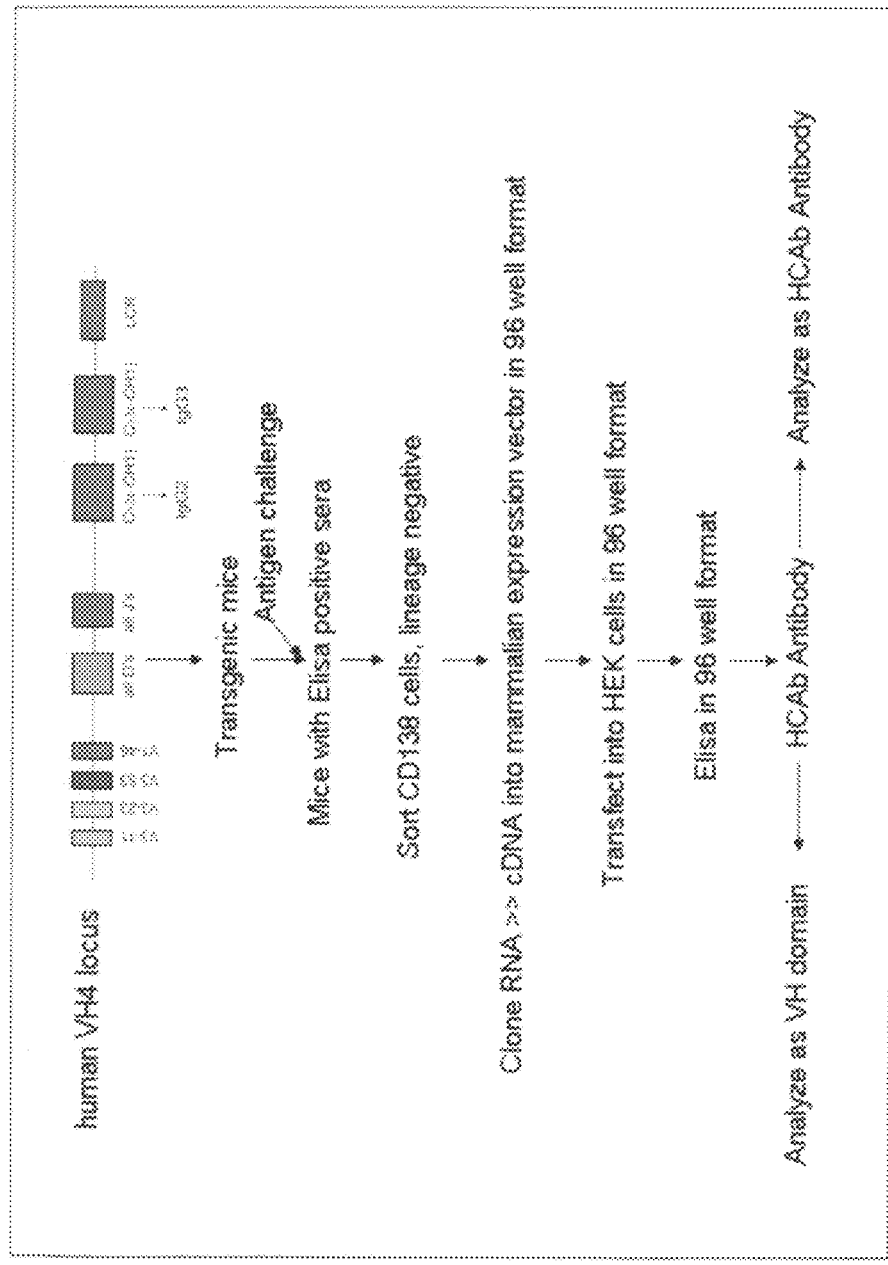
FIG. 17. Immunisation and isolation protocol of human HCAb by sorting CD138 positive cells and direct expression cloning into HEK cells.

The CH1 regions have been deleted from the human Cγ constant regions to allow the production of human heavy chain-only antibodies as described (Janssens et al (2006) PNAS, 103, 15130-15135). The mice are immunised using standard protocols and the antibodies are isolated as schematically shown in FIG. 17.

Figure 12:
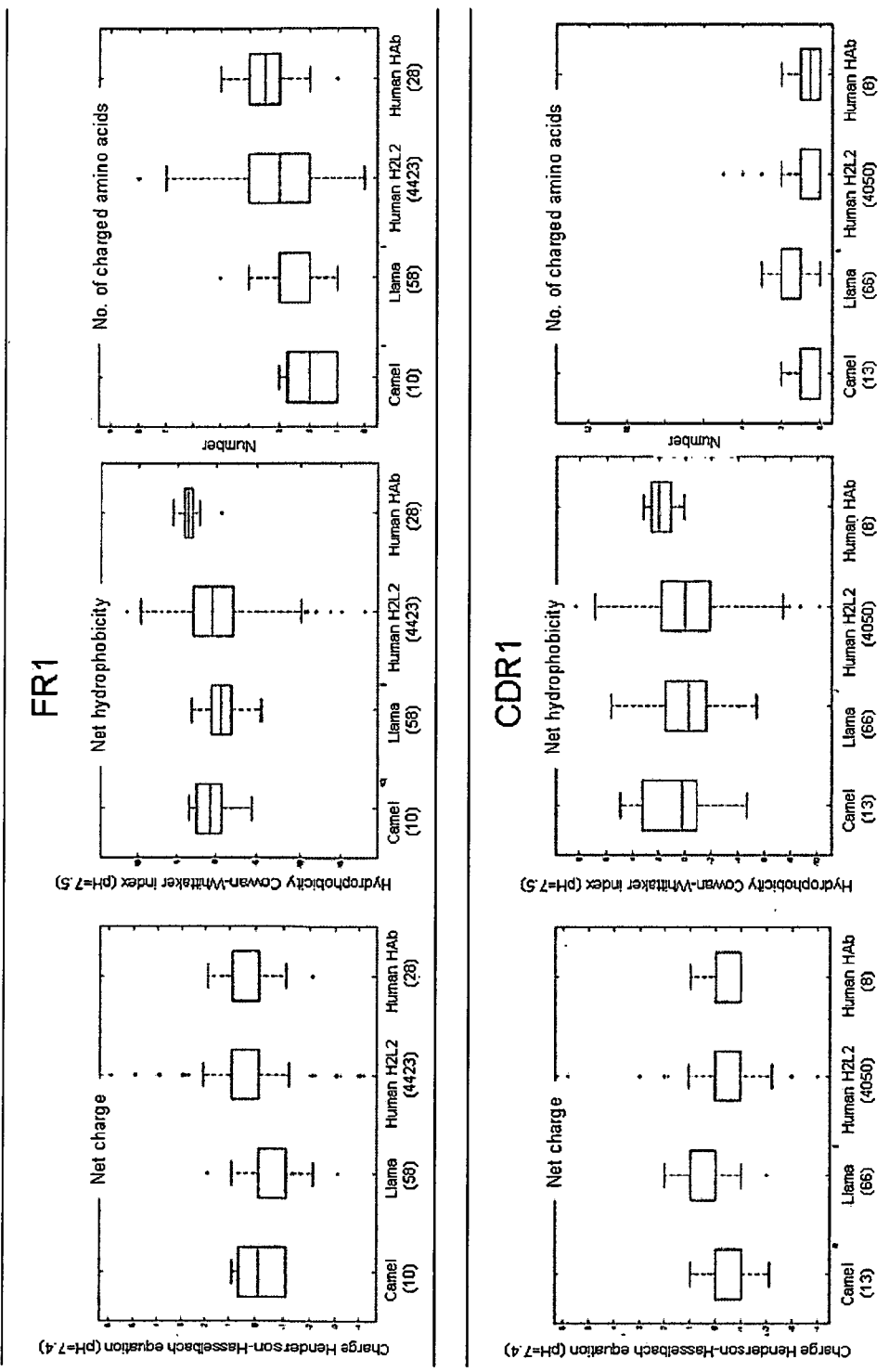
FIG. 12. Box-plot analysis of the framework 1 (FR1) and CDR1 regions of human heavy chain-only antibodies (HCAb) compared to the same regions from camel, llama and human heavy chains from normal tetrameric heavy/light chain antibodies. Net charge was determined by the Henderson-Hasselbach equation at pH=7.4; net hydrophobicity was determined by the Cowan-Whittaker index at pH=7.5. The numbers below the different antibodies are the number of unique input sequences.
Figure 13:
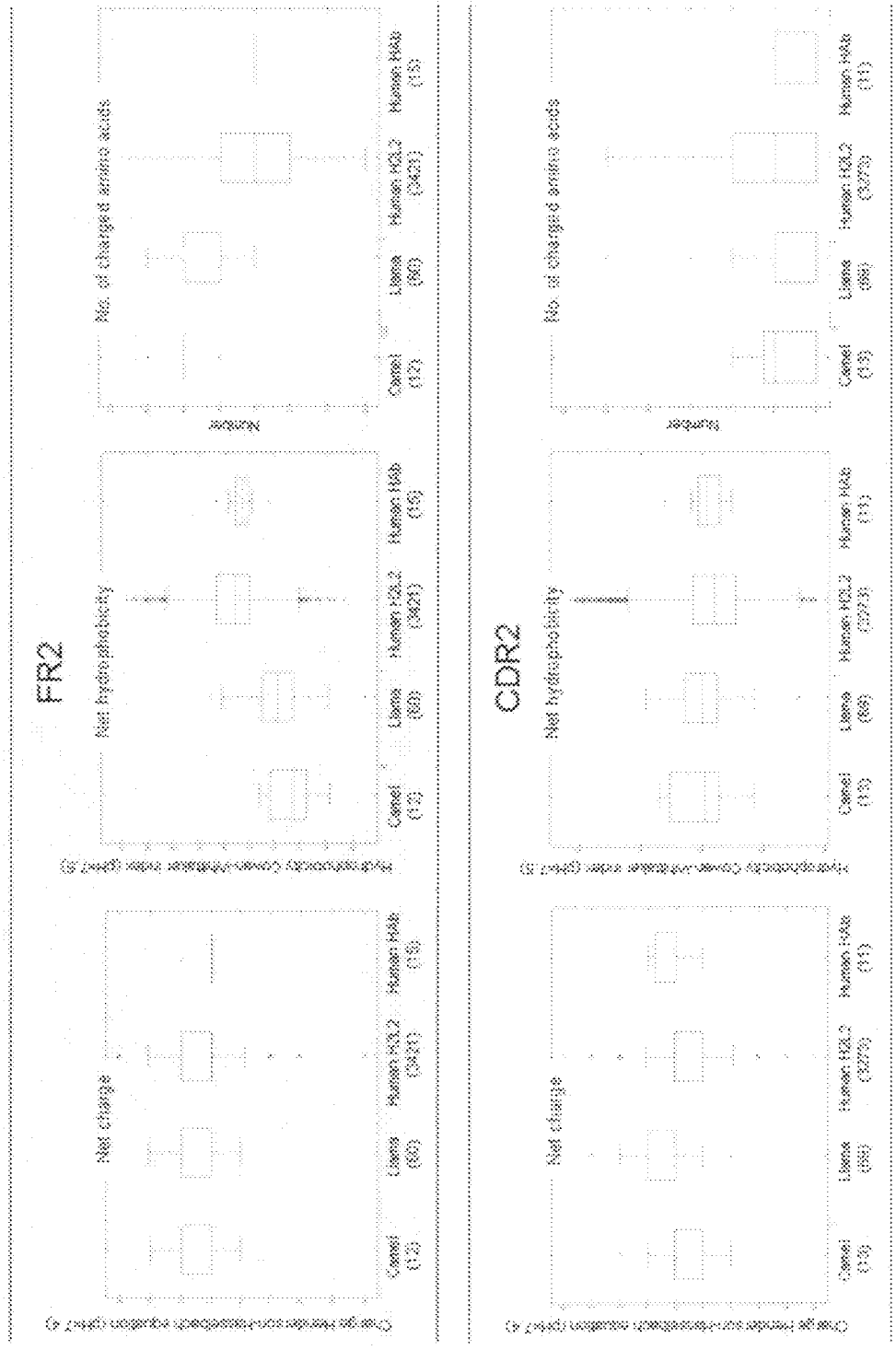
FIG. 13. Box-plot analysis of the framework 2 (FR2) and CDR2 regions of human heavy chain-only antibodies (HCAb) compared to the same regions from camel, llama and human heavy chains from normal tetrameric heavy/light chain antibodies. Net charge was determined by the Henderson-Hasselbach equation at pH=7.4; net hydrophobicity was determined by the Cowan-Whittaker index at pH=7.5. The numbers below the different antibodies are the number of unique input sequences.
Figure 18:
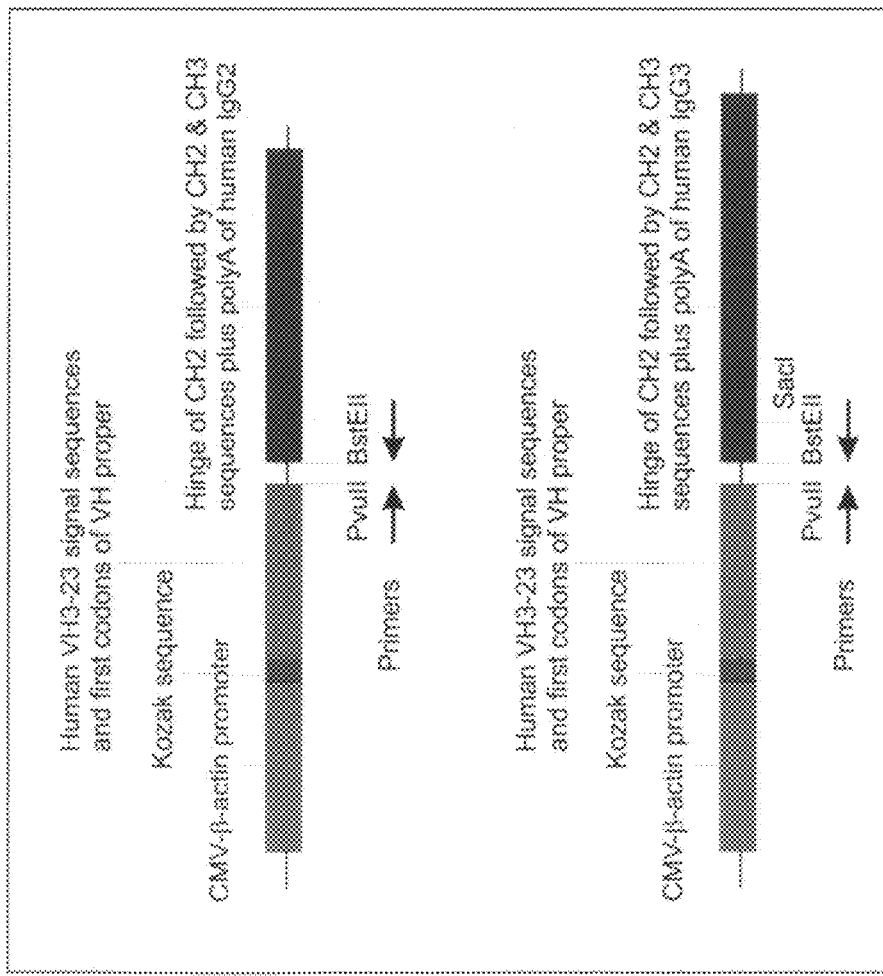
FIG. 18. Vector for mammalian cell expression of HCAb. The vector has a standard pUC backbone (not shown) with an ampicillin resistance gene and a mammalian resistance gene (hygromycin). The relevant part contains a standard CMV enhancer and chicken β-actin promoter (InVitrogen) followed by a Kozak ribosome binding site followed by the signal sequence of VH3-23. The back end of the cassette consists of either an IgG2 or IgG3 constant region starting with the hinge and CH2 domains. The VH cDNAs are cloned between these two regions after amplification, with the primers indicated by the arrows.
Figure 19:
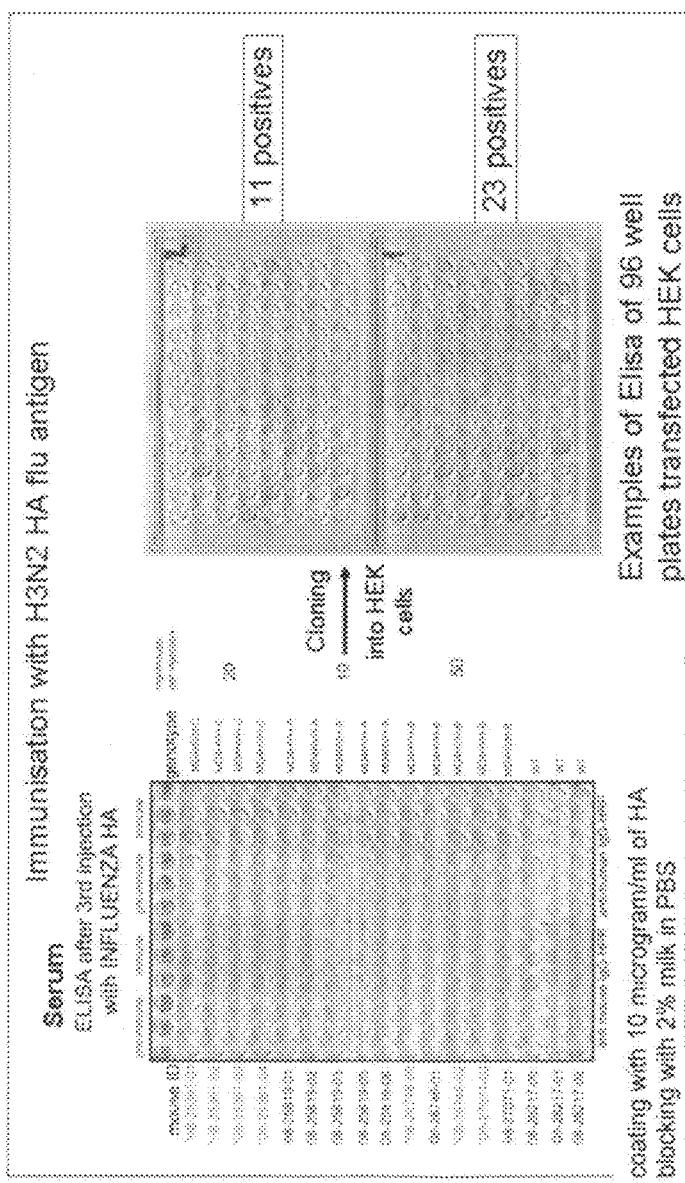
FIG. 19. Example and summary of the direct expression cloning of HCAb into HEK cells. The top panel on the left shows a standard ELISA to determine which of the immunised mice were positively responding to the HA antigen immunisation (the mice in red were used for the HEK cell expression cloning). The top panel on the right shows two examples of an ELISA carried out on the transfected HEK cells in the 96 well format.
Figure 20:
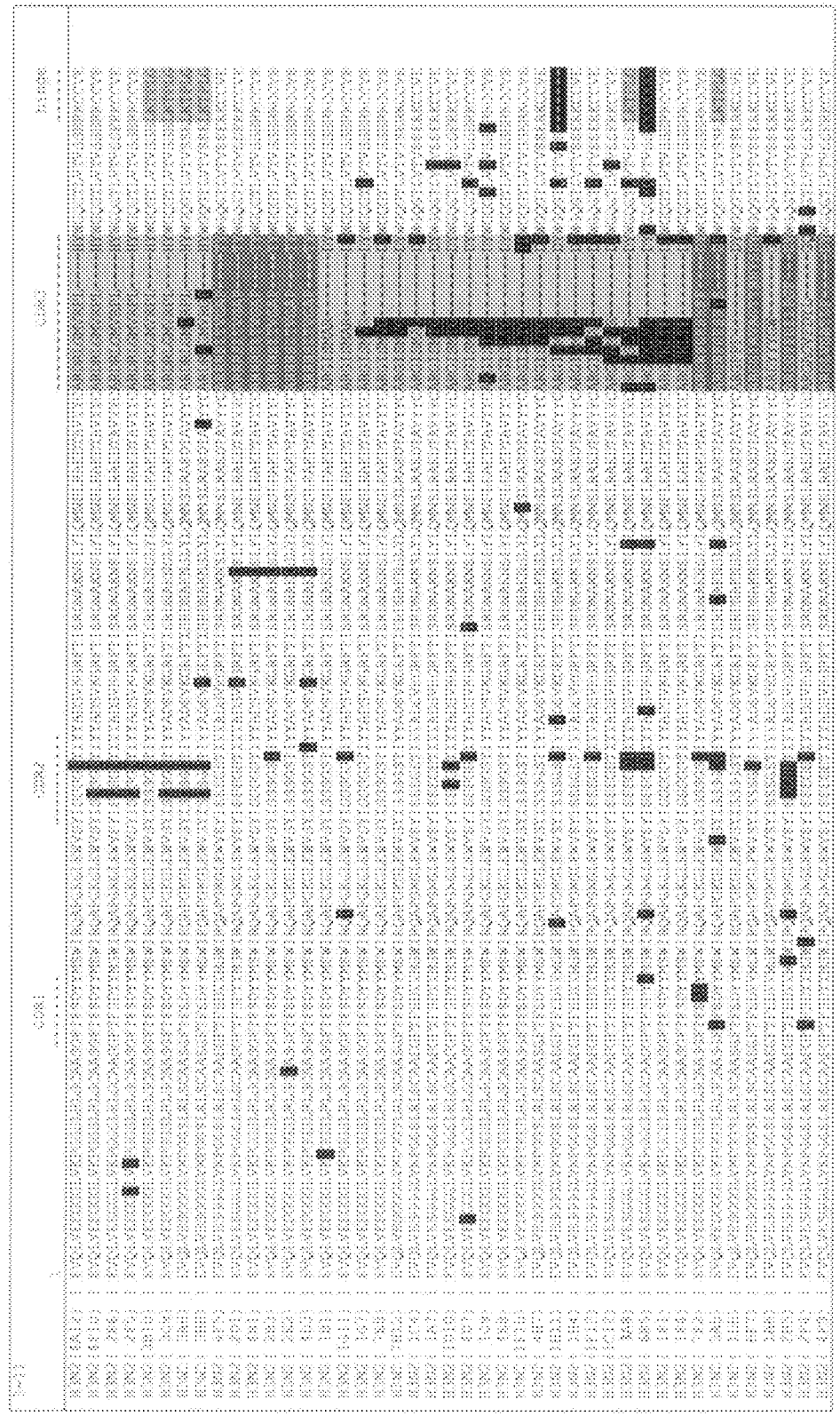
FIG. 20. Sequence analysis of the ELISA-positive HCAb derived from the 3-11 VH germline sequence, listing SEQ ID NOS:57-99, from top to bottom.
Figure 21:
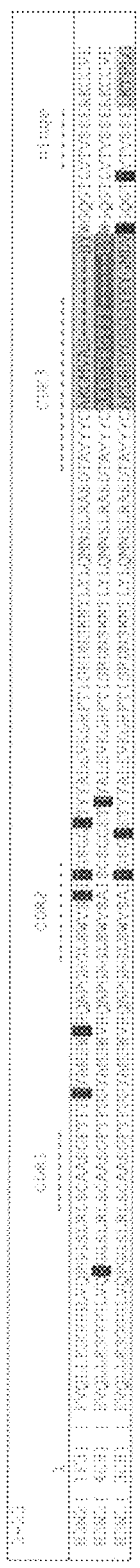
FIG. 21. Sequence analysis of the ELISA-positive HCAb derived from the 3-23 VH germline sequence, listing SEQ ID NOS:100-102, from top to bottom.
Figure 22:
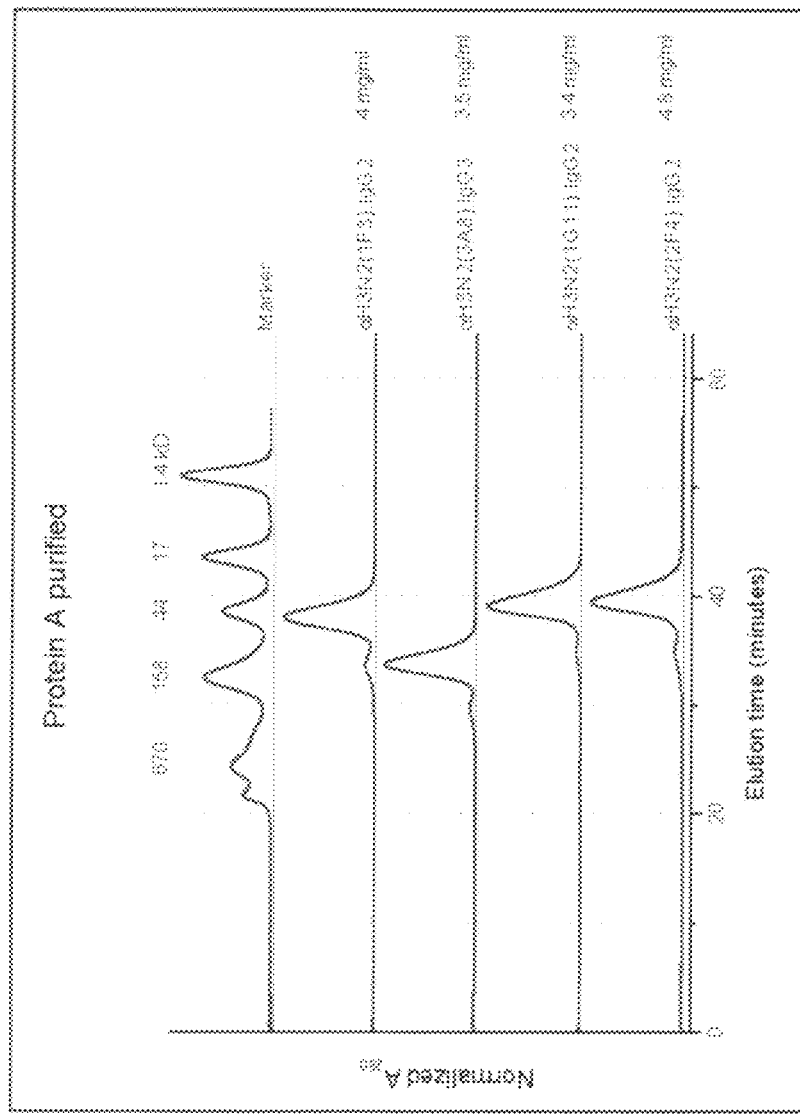
FIG. 22. Elution profile of complete heavy chain-only IgGs on Sephadex 200 Smart columns.
Figure 23:
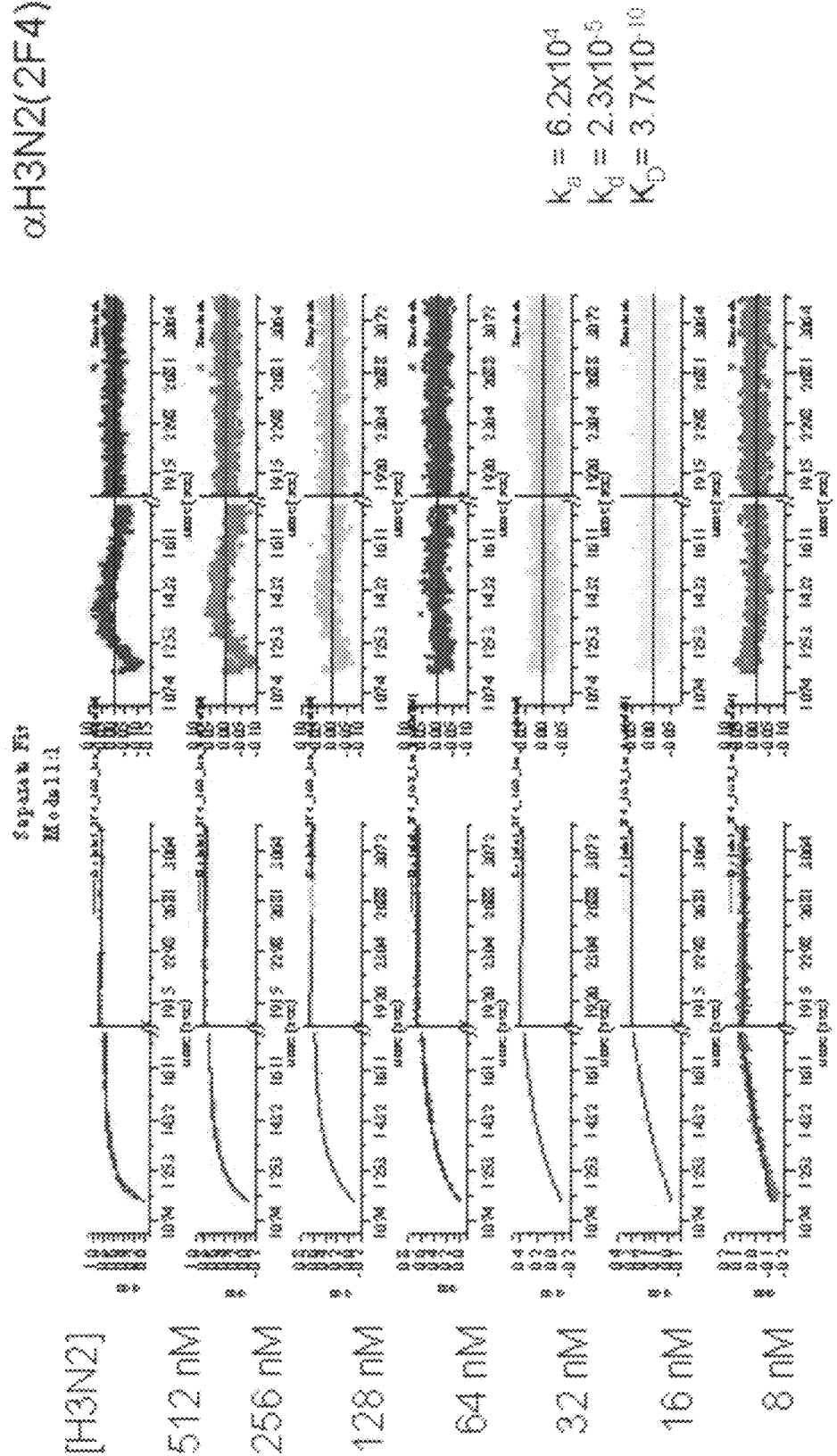
FIGS. 23 and 24. Affinity measurements of two of the anti-HA HCAb on Octet.
Figure 24:
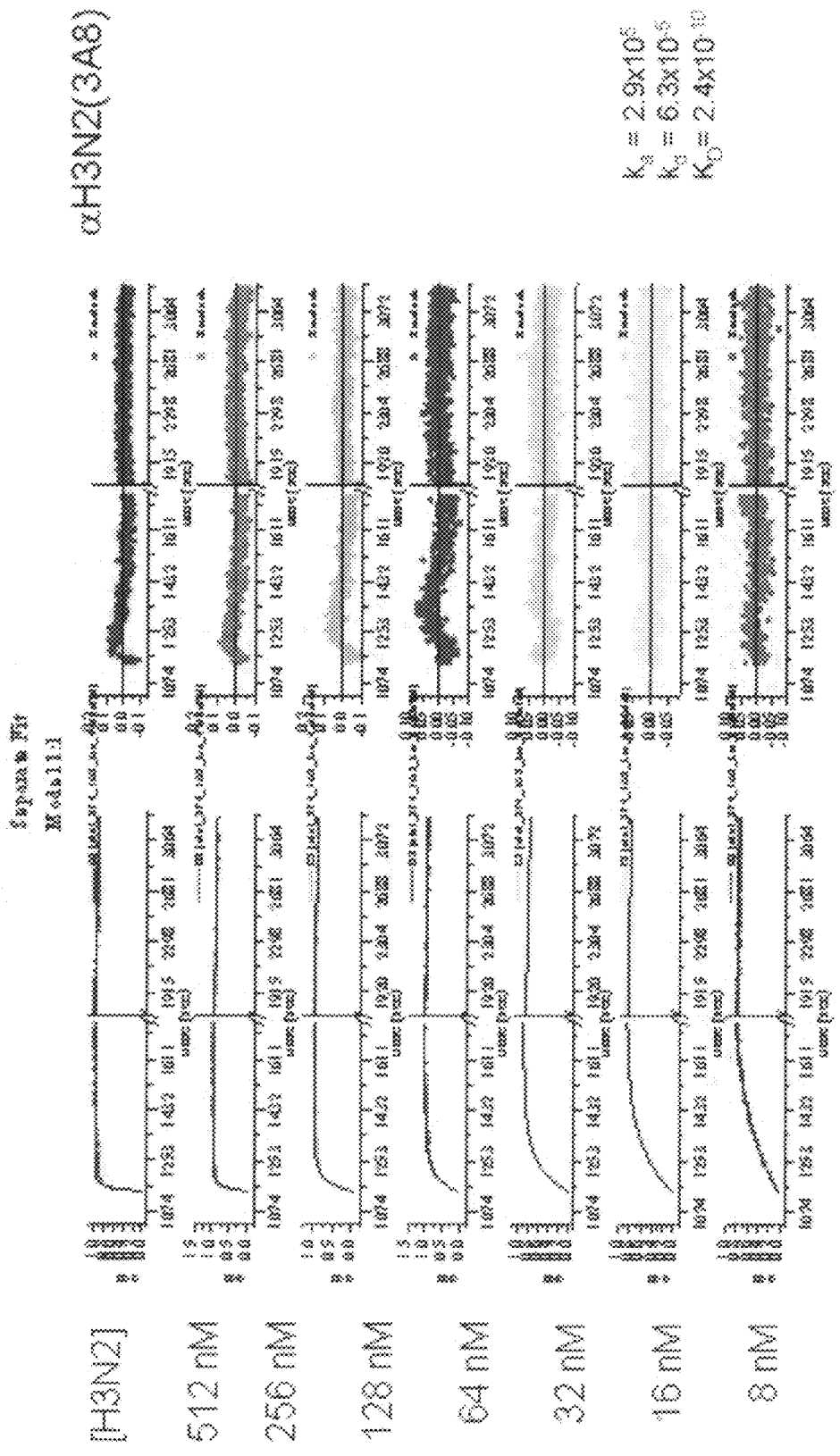
Figure 25:
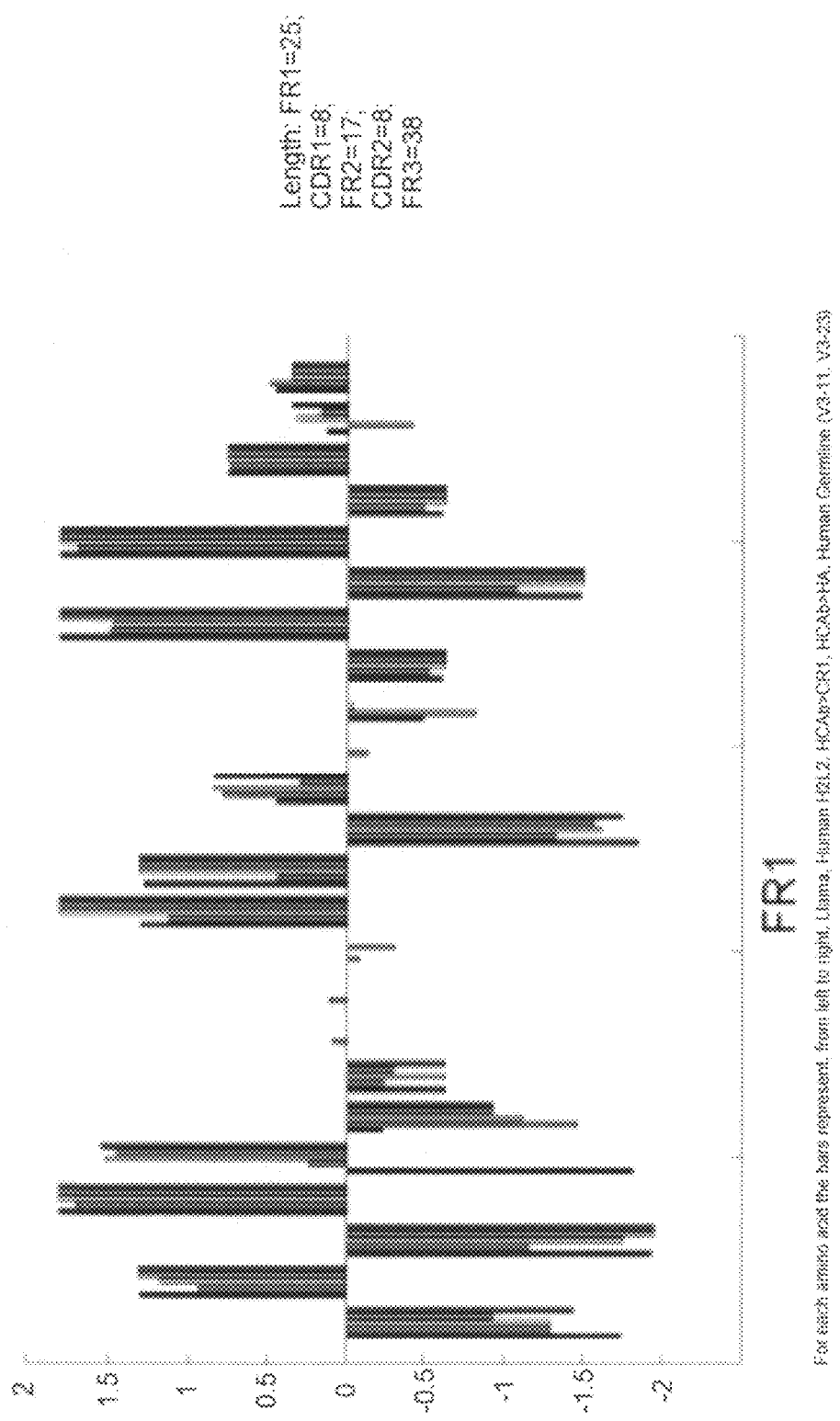
FIGS. 25-28. Amino acids across the VH regions (FR1 (FIG. 25), CDR1 and FR2 (FIG. 26), CDR2 (FIG. 27), and FR3 (FIG. 28)) of the anti-HA HCAb in comparison to those seen in human anti-CR1 HCAb (see above), human tetrameric and llama HCAb.

After immunisation, the plasma cells are collected and sorted (FACS) for the presence of the CD138 antigen and the absence of lineage markers by standard methods (see Sanderson et al (1989) Cell Regulation 1, 27-35; Kim et al (1994) Mol. Biol. Cell, 5, 797-805 and see magnetic sorting Kit for mouse CD138+ plasma cell isolation from Miltenyi Biotec). The cells are collected and the mRNA reverse transcribed and amplified into cDNA with VH domain-specific primers by standard methods (e.g Janssens et al (2006) PNAS, 103, 15130-15135). The primers used are on the 5' end and are designed to introduce a PvuII site for cloning purposes (FIG. 18). The primers at the 3' end are from the IgG2 or IgG3 CH2 hinge region and are designed to have a BstEII site. Where this is not possible, the primer for the IgG3 contains a SacI site for cloning purposes (FIG. 18). The resulting VH fragments are cloned into two mammalian expression vectors containing a CMV enhancer and a chicken β-actin promoter followed by a Kozak and signal sequence of VH3-23 ending at its PvuII site in the VH segment proper. In the first vector (FIG. 18), this is followed by human IgG2 starting at the hinge region (from the BstEII site) of CH2 with CH2, CH3, a stop codon and polyA sequence. In the second vector, all IgG2 sequences are replaced by the equivalent human IgG3 sequences. The latter allows the cloning of HCAbs that do not contain a BstEII site using the SacI site as an alternative. The remainder of the plasmid has a standard mammalian cell selectable marker such as a hygromycin resistance cassette in a pUC based plasmid. Obviously, the human IgG2 or 3 could be replaced by any other CH1-deficient constant region from human or any other species. Equally obviously, the same is true for the VH part of the vector. The cDNA is then cloned between the PvuII and BstEII (or the PvuII and SacI) sites and the vector transfected in E. coli by standard techniques. Colonies are picked into 96 (or 384) well microtiter plates containing bacterial growth medium. The plates (typically >10) are incubated to allow the bacteria to grow and DNA is prepared in each well. The DNA from each well, i.e. each complete plate, is subsequently added to a new 96 well plate containing mammalian HEK cells (or other cells for expression purposes) for transformation by standard transfection reagents and methods. The transformed cells are grown under selection based on the selection marker present on the expression plasmid (e.g. hygromycin). The medium containing the expressed antibody is subsequently analysed for the presence of antigen-specific HCAb by standard ELISA assays. This can be carried out in the same 96 well format, but could also be done in other formats e.g. by microarrays, to save on the amount of antigen to be used. Positive wells immediately identify the plasmids that contain a human HCAb that codes for an antigen-specific HCAb. FIG. 19 shows the ELISA of the sera from the mice that were immunized and examples of the ELISA of the transfected HEK cells in the 96 well format. It also summarizes the HA cloning experiment, less than one millionth of the cDNA was used in the experiment using 960 wells in total. This yielded 28 different antigen-specific antibodies falling in 13 groups by sequence analysis derived from two of the VH regions VH3-11 (FIG. 21) and VH3-23 (FIG. 22). Both IgG2 (SSERKCCVE) and IgG3 (SSELKTPLG) are used, the VH regions have undergone hypermutation and, similar to humans, the J4 region is used most frequently, although others are also used. The secreted HCAb are soluble and are monomers, as determined by their elution profiles on a standard SMART column (FIG. 23). The affinities of the antibodies range form nanomolar to subnanomolar affinity as determined by standard binding and dissociation profiles on an Octet (FIG. 24) or BiaCore analysis. Analysis of the mutations and comparison to other immunoglobulin sequences (FIG. 25) results in the same properties of the different regions as shown in FIGS. 11-13.

As described above soluble VH domains can be isolated from soluble HCAb derived from plasma cells.

EXAMPLE 8

Generation and Expression Cloning of Human HCAb from Single Cells

Figure 26:
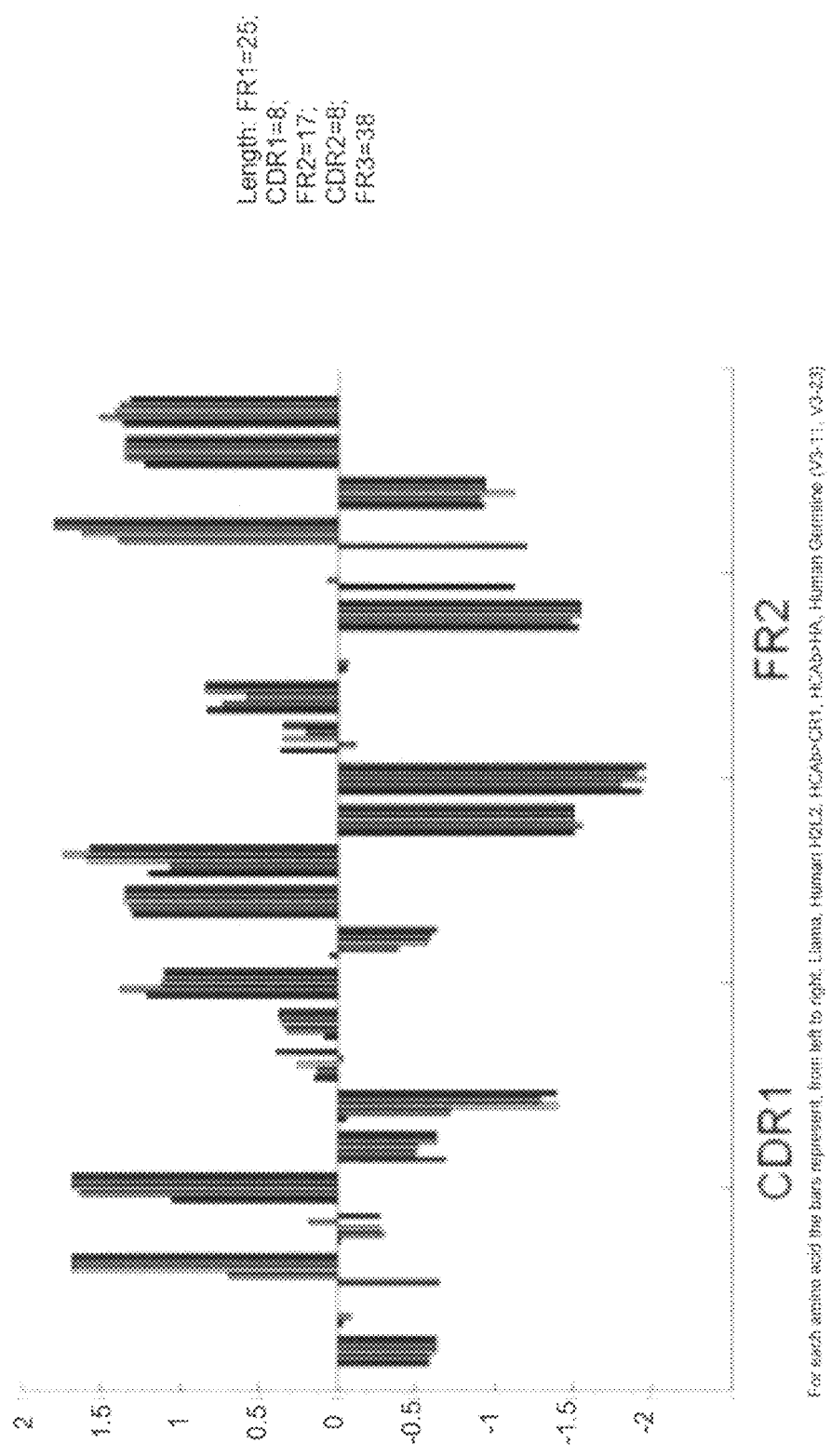
Figure 27:
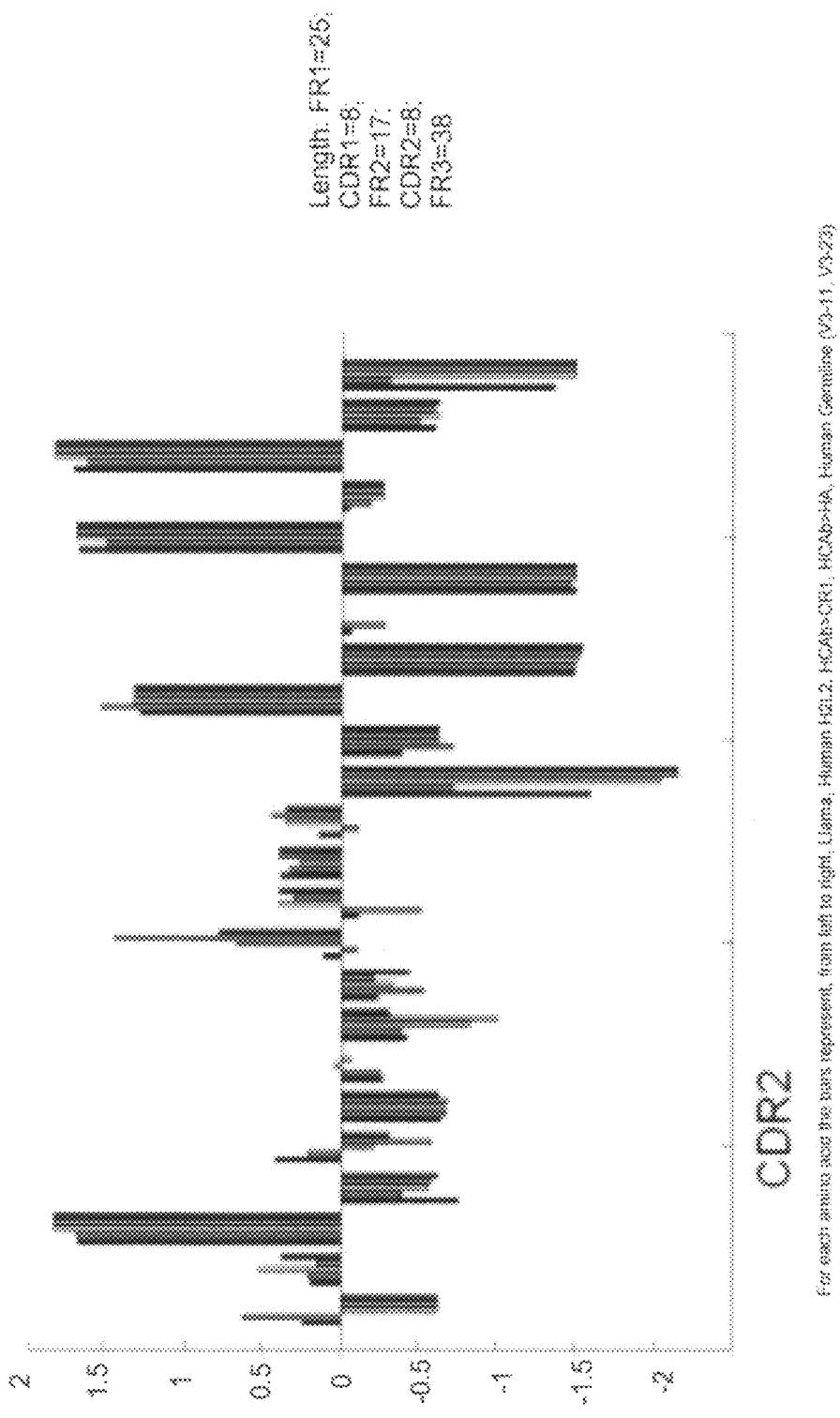
Figure 28:
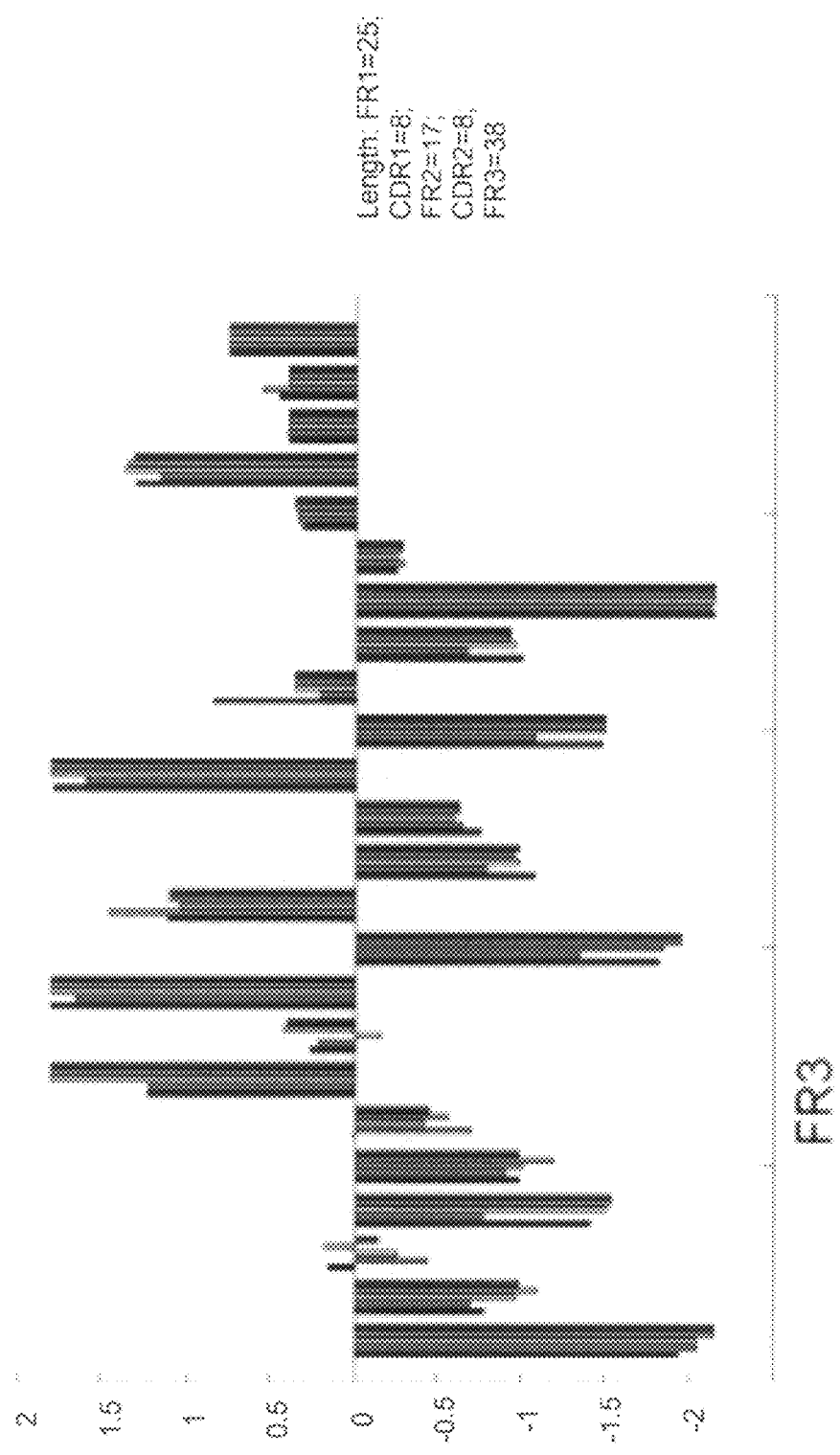
Figure 29:
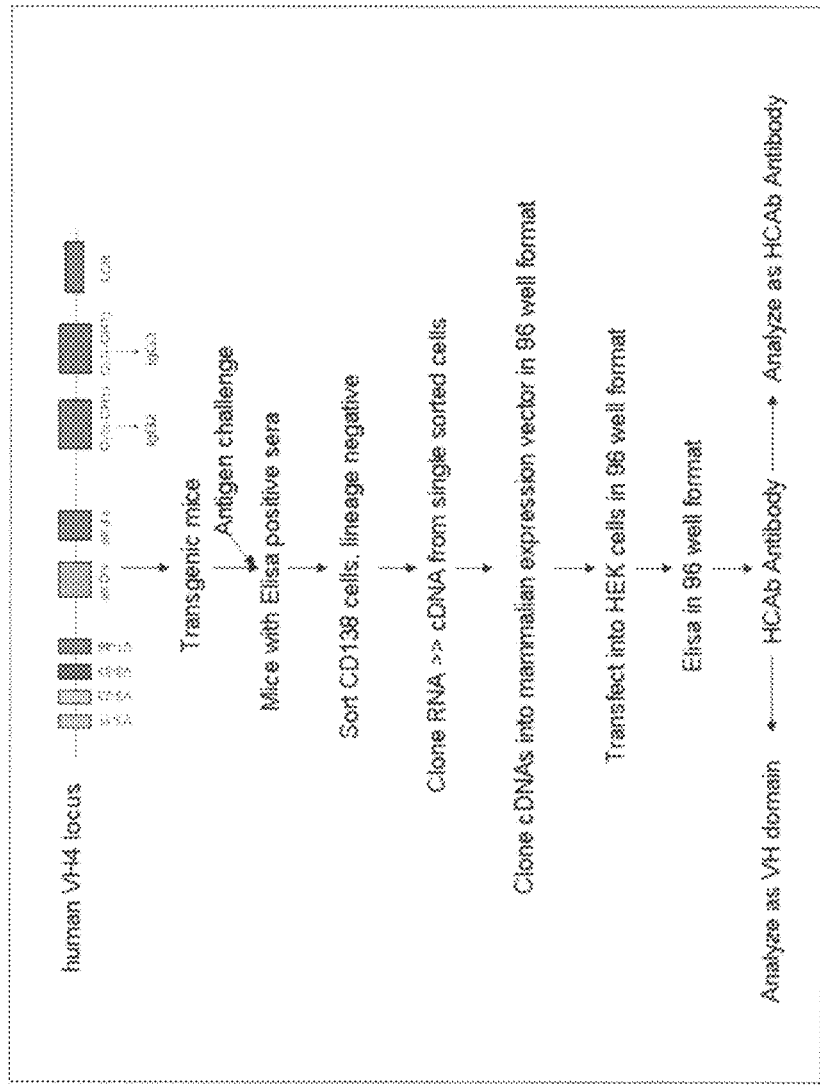
FIG. 29. Immunisation and isolation protocol of human HCAb after single cell sorting and direct expression cloning into HEK cells.
Figure 30:
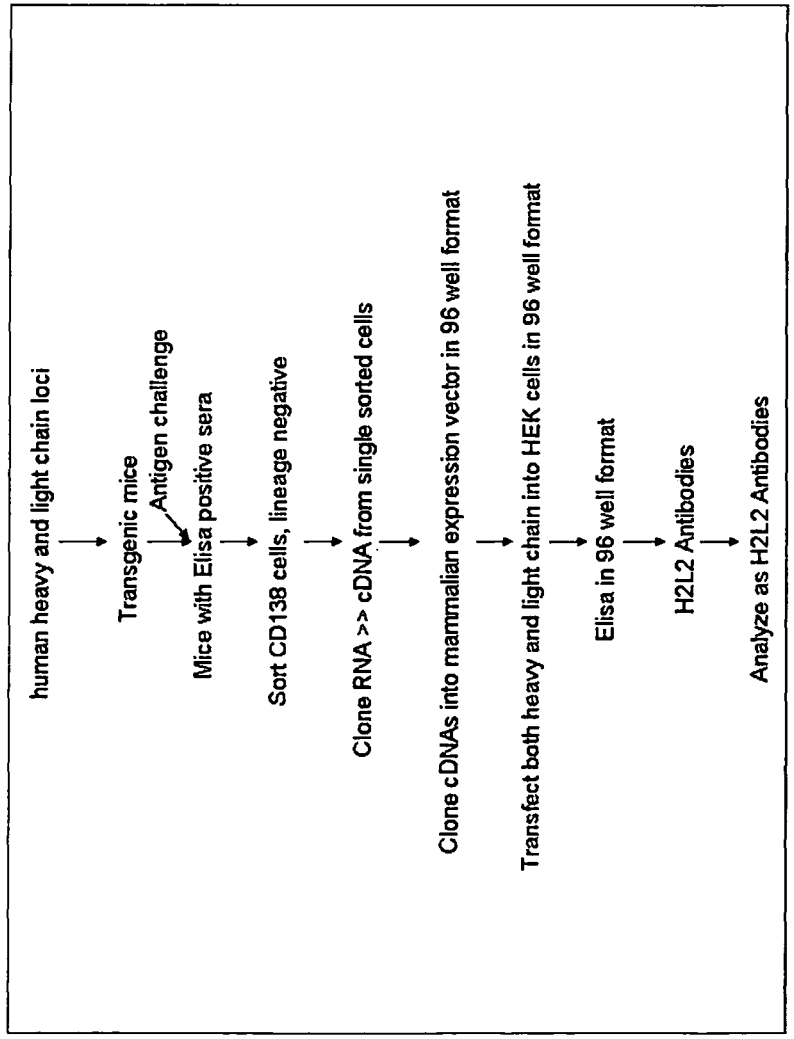
FIG. 30. Immunisation and isolation protocol of normal tetrameric human heavy and light chain antibodies after single cell sorting and direct expression cloning into HEK cells.

A variant of the scheme described above by cloning directly into HEK cells would be to sort the CD138+ lineage negative cells and derive the cDNA from single cells that could be cloned directly into HEK or other mammalian cells (FIG. 26). These would be analysed by very similar methods as described above.

EXAMPLE 9

Generation and Expression Cloning of Normal Human Heavy and Light Chain (Tetrameric) Antibodies from Single Cells A variant of the method shown in example 8 can also be used to clone transgene-expressed normal tetrameric antibodies directly by expression cloning into HEK or other mammalian cells. In the variant, single cells are again isolated by sorting. The RNA is isolated from single cells and both the VH and VL domains are cloned via PCR amplification into a heavy and light chain expression vector analogous to what is described above. The individual combination of the cloned heavy and light chain expression plasmids are transfected together into HEK or other mammalian cells. The formats, the screening and the analysis are entirely analogous to that described above for the HCAb 96 well format (examples 8 and 9).

We claim:

1. A transgenic non-human mammal comprising a transgene, the transgene comprising at least one heterologous immunoglobulin heavy chain locus comprising human VH gene segments, one or more human D gene segments, human J gene segments, and at least one mouse constant region gene segment wherein the human VH gene segments comprise up to 20 VH gene segments and all of said human VH gene segments are naturally occurring, the human D gene segments comprise at least 5 human D gene segments, the human J gene segments comprise all six human J gene segments, and the mouse constant region gene segment comprises a Cγ lacking CH1.

2. The transgenic non-human mammal according to claim 1, wherein said locus further comprises a selectable marker.

3. The transgenic non-human mammal according to claim 1, wherein the mammal is a rodent.

4. The transgenic non-human mammal according to claim 3, wherein the rodent is a mouse.

5. A method of producing a heavy chain-only antibody which binds specifically to an antigen comprising:
   (a) immunising the non-human transgenic mammal of claim 1 with the antigen, wherein the mammal expresses heavy chain-only antibodies which lack CH1 functionality in the transcribed and processed heavy chain mRNA;
   (b) isolating long-lived plasma cells or memory B-cells from the immunised mammal;
   (c) isolating an mRNA population from cells derived from step (b);
   (d) cloning a cDNA population derived from the mRNA isolated in step (c) into an expression vector and expressing the cDNA in a cell-line of choice; and
   (e) selecting at least one cell-line which produces a heavy chain-only antibody which binds specifically to the antigen.

6. A method of producing a heavy chain-only antibody which binds specifically to an antigen comprising:
   (a) immunising the non-human transgenic mammal of claim 1 with the antigen, wherein the mammal expresses heavy chain-only antibodies which lack CH1 functionality in the transcribed and processed heavy chain mRNA;
   (b) isolating long-lived plasma cells or memory B-cells from the immunised mammal;
   (c) isolating an mRNA population from cells derived from step (b);
   (d) cloning a cDNA population comprising VH domains derived from the mRNA isolated in step (c) into expression vector of choice such that a VH fusion protein, which may comprise a heavy chain effector region, is expressed in a cell-line of choice; and
   (e) selecting at least one cell-line which produces a VH fusion protein which binds specifically to the antigen.

7. A method of deriving a human, antibody from a hybrid antibody comprising:
   (a) carrying out the steps of claim 5 or 6;
   (b) cloning and sequencing the $V_H$ domain from the cell line;
   (c) recloning selected sequences comprising the $V_H$ binding domain coding sequences with human constant effector domains of choice; and
   (e) expressing the recloned sequences using an expression vector in a cell type of choice.

8. A vector comprising an immunoglobulin heavy chain locus comprising human VH gene segments, one or more human D gene segments, human J gene segments, and at least one mouse constant region gene segment wherein the human VH gene segments comprise up to 20 VH gene segments and all of said human VH gene segments are naturally occurring, the human D gene segments comprise at least 5 human D gene segments, the human J gene segments comprise all six human J gene segments, and the mouse constant region gene segment comprises a Cγ lacking CH1.

* * * * *

SEQUENCE LISTING

```
<160> NUMBER OF SEQ ID NOS: 102

<210> SEQ ID NO 1
<211> LENGTH: 9
<212> TYPE: PRT
<213> ORGANISM: Homo sapiens

<400> SEQUENCE: 1

Ser Ser Glu Arg Lys Cys Cys Val Glu
1               5

<210> SEQ ID NO 2
<211> LENGTH: 9
<212> TYPE: PRT
<213> ORGANISM: Homo sapiens

<400> SEQUENCE: 2

Ser Ser Glu Leu Lys Thr Pro Leu Gly
1               5

<210> SEQ ID NO 3
<211> LENGTH: 98
<212> TYPE: PRT
<213> ORGANISM: Homo sapiens
```

<400> SEQUENCE: 3

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```

<210> SEQ ID NO 4
<211> LENGTH: 95
<212> TYPE: PRT
<213> ORGANISM: Lama glama

<400> SEQUENCE: 4

```
Gln Val Gln Leu Leu Glu Ser Gly Gly Glu Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Val Arg Gln Ala Pro Gly Gln Arg Leu Val Ala
        35                  40                  45

Ala Ile Thr Ser Gly Gly Ser Thr Asn Tyr Ala Asp Ser Val Lys Gly
    50                  55                  60

Arg Phe Thr Ile Ser Arg Asp Asn Ala Lys Asn Thr Val Tyr Leu Gln
65                  70                  75                  80

Met Asn Ser Leu Lys Pro Glu Asp Thr Ala Val Tyr Tyr Cys Asn
                85                  90                  95
```

<210> SEQ ID NO 5
<211> LENGTH: 130
<212> TYPE: PRT
<213> ORGANISM: Homo sapiens

<400> SEQUENCE: 5

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asn Ser Thr Tyr Tyr Ala Asp Ser Val
    50                  55                  60

Glu Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Ile Tyr Tyr Cys
                85                  90                  95

Ala Lys Asp Arg Thr Gly Gly Pro Gly Gly Phe Asp Tyr Trp Gly
            100                 105                 110

Gln Gly Thr Leu Val Thr Val Ser Ser Glu Arg Lys Cys Cys Val Glu
```

Ala Ala
    130

<210> SEQ ID NO 6
<211> LENGTH: 130
<212> TYPE: PRT
<213> ORGANISM: Homo sapiens

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ala Ile Ser Gly Ser Ala Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Asp Arg Thr Gly Gly Pro Gly Gly Gly Phe Asp Tyr Trp Gly
            100                 105                 110

Gln Gly Thr Leu Val Thr Val Ser Ser Glu Leu Lys Thr Pro Leu Gly
        115                 120                 125

Ala Ala
    130

<210> SEQ ID NO 7
<211> LENGTH: 96
<212> TYPE: PRT
<213> ORGANISM: Homo sapiens

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

<210> SEQ ID NO 8
<211> LENGTH: 128
<212> TYPE: PRT
<213> ORGANISM: Homo sapiens

<400> SEQUENCE: 8

Met Ala Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Val Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Asp Leu Gln Met Asn Ser Leu Arg Ala Glu Asp Thr Ala Val Tyr
                85                  90                  95

Tyr Cys Ala Lys Gly Asp Met Ile Asn Ser Ser Arg Trp Tyr Arg Gly
            100                 105                 110

Glu Gly Thr Leu Val Thr Val Ser Ser Glu Leu Lys Thr Pro Leu Gly
        115                 120                 125

<210> SEQ ID NO 9
<211> LENGTH: 128
<212> TYPE: PRT
<213> ORGANISM: Homo sapiens

<400> SEQUENCE: 9

Met Ala Gln Val Gln Leu Leu Gln Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Asp Leu Gln Met Asn Ser Leu Arg Ala Glu Asp Thr Ala Val Tyr
                85                  90                  95

Tyr Cys Ala Lys Gly Asp Met Ile Asn Ser Ser Arg Trp Tyr Arg Gly
            100                 105                 110

Glu Gly Thr Leu Val Thr Val Ser Ser Glu Leu Lys Thr Pro Leu Gly
        115                 120                 125

<210> SEQ ID NO 10
<211> LENGTH: 128
<212> TYPE: PRT
<213> ORGANISM: Homo sapiens

<400> SEQUENCE: 10

Met Ala Glu Val Lys Leu Val Gln Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Val Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Asp Leu Gln Met Asn Ser Leu Arg Ala Glu Asp Thr Ala Val Tyr
                85                  90                  95

Tyr Cys Ala Lys Gly Asp Met Val Asn Ser Ser Arg Trp Tyr Arg Gly
            100                 105                 110

Glu Gly Thr Leu Val Thr Val Ser Ser Glu Leu Lys Thr Pro Leu Gly
        115                 120                 125

<210> SEQ ID NO 11
<211> LENGTH: 128
<212> TYPE: PRT
<213> ORGANISM: Homo sapiens

<400> SEQUENCE: 11

Met Ala Gln Val Lys Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Val Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Asp Leu Gln Met Asn Ser Leu Arg Ala Glu Asp Thr Ala Val Tyr
                85                  90                  95

Tyr Cys Ala Lys Gly Asp Met Ile Asn Ser Ser Arg Trp Tyr Arg Gly
            100                 105                 110

Glu Gly Thr Leu Val Thr Val Ser Ser Glu Leu Lys Thr Pro Leu Gly
        115                 120                 125

<210> SEQ ID NO 12
<211> LENGTH: 128
<212> TYPE: PRT
<213> ORGANISM: Homo sapiens

<400> SEQUENCE: 12

Met Ala Glu Val Lys Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Val Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Asp Leu Gln Met Asn Ser Leu Arg Ala Glu Asp Thr Ala Val Tyr
                85                  90                  95

Tyr Cys Ala Lys Gly Asp Met Ile Asn Ser Ser Arg Trp Tyr Arg Gly
            100                 105                 110

Glu Gly Thr Leu Val Thr Val Ser Ser Glu Leu Lys Thr Pro Leu Gly
        115                 120                 125

<210> SEQ ID NO 13
<211> LENGTH: 127
<212> TYPE: PRT
<213> ORGANISM: Homo sapiens

<400> SEQUENCE: 13

Met Ala Glu Val Gln Leu Val Glu Ser Gly Gly Gly Leu Val Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Val Arg Gln Ala Pro Gly Lys Gly Leu Glu Trp
        35                  40                  45

Val Ser Val Ile Ser Gly Ser Gly Gly Ser Thr Tyr Tyr Ala Asp Ser
 50                  55                  60

Val Lys Gly Arg Phe Thr Ile Ser Arg Asp Asn Ser Lys Asp Thr Leu
 65                  70                  75                  80

Asp Leu Gln Met Asn Ser Leu Arg Ala Glu Asp Ala Ala Val Tyr Tyr
                85                  90                  95

Cys Ala Lys Gly Asp Met Ile Asn Ser Ser Arg Trp Tyr Arg Gly Glu
                100                 105                 110

Gly Thr Leu Val Thr Val Ser Ser Glu Leu Lys Thr Pro Leu Gly
            115                 120                 125

<210> SEQ ID NO 14
<211> LENGTH: 128
<212> TYPE: PRT
<213> ORGANISM: Homo sapiens

<400> SEQUENCE: 14

Met Ala Gln Val Gln Leu Val Glu Ser Gly Gly Gly Leu Val Gln Pro
 1               5                  10                  15

Gly Gly Ser Leu Arg Leu Ser Cys Ala Ala Ser Gly Phe Thr Phe Gly
            20                  25                  30

Ser Tyr Ala Met Ser Trp Val Arg Gln Ala Pro Gly Lys Gly Leu Glu
        35                  40                  45

Trp Val Ser Val Ile Ser Gly Ser Gly Gly Ser Thr Tyr Tyr Ala Asp
 50                  55                  60

Ser Val Lys Gly Arg Phe Thr Ile Ser Arg Asp Asn Ser Lys Asn Thr
 65                  70                  75                  80

Leu Asp Leu Gln Met Asn Ser Leu Arg Ala Glu Asp Thr Ala Val Tyr
                85                  90                  95

Tyr Cys Ala Lys Gly Asp Met Val Asn Ser Ser Arg Trp Tyr Arg Gly
                100                 105                 110

Glu Gly Thr Leu Val Thr Val Ser Ser Glu Leu Lys Thr Pro Leu Gly
            115                 120                 125

<210> SEQ ID NO 15
<211> LENGTH: 128
<212> TYPE: PRT
<213> ORGANISM: Homo sapiens

<400> SEQUENCE: 15

Met Ala Glu Val Lys Leu Leu Glu Ser Gly Gly Gly Leu Val Lys Pro
 1               5                  10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Val Ile Ser Gly Ser Gly Gly Ser Thr Tyr Tyr Ala Asp
 50                  55                  60

Ser Val Lys Gly Arg Phe Thr Ile Ser Arg Asp Asn Ser Lys Asn Thr
 65                  70                  75                  80

Leu Asp Leu Gln Met Asn Ser Leu Arg Ala Glu Asp Thr Ala Val Tyr
                85                  90                  95

```
Tyr Cys Ala Lys Gly Asp Met Val Asn Ser Ser Arg Trp Tyr Arg Gly
                100                 105                 110

Glu Gly Thr Leu Val Thr Val Ser Ser Glu Leu Lys Thr Pro Leu Gly
        115                 120                 125
```

<210> SEQ ID NO 16
<211> LENGTH: 128
<212> TYPE: PRT
<213> ORGANISM: Homo sapiens

<400> SEQUENCE: 16

```
Met Ala Gln Val Gln Leu Val Glu Ser Gly Gly Gly Leu Val Pro Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Val Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Asp Leu Gln Met Asn Ser Leu Arg Ala Glu Asp Thr Ala Val Tyr
                85                  90                  95

Tyr Cys Ala Lys Gly Asp Met Ile Asn Ser Ser Arg Trp Tyr Arg Gly
                100                 105                 110

Glu Gly Thr Leu Val Thr Val Ser Ser Glu Leu Lys Thr Pro Leu Gly
        115                 120                 125
```

<210> SEQ ID NO 17
<211> LENGTH: 128
<212> TYPE: PRT
<213> ORGANISM: Homo sapiens
<220> FEATURE:
<221> NAME/KEY: VARIANT
<222> LOCATION: 52, 54, 94, 107, 108, 122
<223> OTHER INFORMATION: Xaa = Any Amino Acid

<400> SEQUENCE: 17

```
Met Asp Gln Val Lys Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Xaa Ile Xaa Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Asp Leu Gln Met Asn Ser Leu Arg Ala Glu Asp Thr Xaa Val Tyr
                85                  90                  95

Tyr Cys Ala Lys Gly Asp Met Val Asn Ser Xaa Xaa Trp Tyr Arg Gly
                100                 105                 110

Glu Gly Thr Leu Val Thr Val Ser Ser Xaa Leu Lys Thr Pro Leu Gly
        115                 120                 125
```

<210> SEQ ID NO 18
<211> LENGTH: 128
<212> TYPE: PRT
<213> ORGANISM: Homo sapiens

<400> SEQUENCE: 18

Met Ala Gln Val Lys Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Val Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Asp Leu Gln Met Asn Ser Leu Arg Ala Glu Asp Thr Ala Val Tyr
                85                  90                  95

Tyr Cys Ala Lys Gly Asp Met Val Asn Ser Ser Arg Trp Tyr Arg Gly
            100                 105                 110

Glu Gly Thr Leu Val Thr Val Ser Ser Glu Leu Lys Thr Pro Leu Gly
            115                 120                 125

<210> SEQ ID NO 19
<211> LENGTH: 128
<212> TYPE: PRT
<213> ORGANISM: Homo sapiens

<400> SEQUENCE: 19

Met Ala Gln Val Lys Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Pro Glu
        35                  40                  45

Trp Val Ser Val Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Asp Leu Gln Met Asn Ser Leu Arg Ala Glu Asp Thr Ala Val Tyr
                85                  90                  95

Tyr Cys Ala Lys Gly Asp Met Ile Asn Ser Ser Arg Trp Tyr Arg Gly
            100                 105                 110

Glu Gly Thr Leu Val Thr Val Ser Ser Glu Leu Lys Thr Pro Leu Gly
            115                 120                 125

<210> SEQ ID NO 20
<211> LENGTH: 128
<212> TYPE: PRT
<213> ORGANISM: Homo sapiens

<400> SEQUENCE: 20

Met Ala Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Val Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Asn Leu Gln Met Asn Ser Leu Arg Ala Glu Asp Thr Ala Val Tyr
                85                  90                  95

Tyr Cys Ala Lys Gly Asp Met Val Asn Ser Ser Arg Trp Tyr Arg Gly
            100                 105                 110

Glu Gly Thr Leu Val Thr Val Ser Ser Glu Leu Lys Thr Pro Leu Gly
        115                 120                 125

<210> SEQ ID NO 21
<211> LENGTH: 128
<212> TYPE: PRT
<213> ORGANISM: Homo sapiens

<400> SEQUENCE: 21

Met Ala Glu Val Lys Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Ser Gly Ser Gly Ser Thr Tyr Tyr Ala Asp
50                  55                  60

Ser Val Lys Gly Arg Phe Thr Ile Ser Arg Asp Asn Ser Lys Asn Thr
65                  70                  75                  80

Leu Asp Leu Gln Met Asn Ser Leu Arg Ala Glu Asp Thr Ala Val Tyr
                85                  90                  95

Tyr Cys Ala Lys Gly Asp Met Ile Asn Ser Ser Arg Trp Tyr Arg Gly
            100                 105                 110

Glu Gly Thr Leu Val Thr Val Ser Ser Glu Leu Lys Thr Pro Leu Gly
        115                 120                 125

<210> SEQ ID NO 22
<211> LENGTH: 133
<212> TYPE: PRT
<213> ORGANISM: Homo sapiens

<400> SEQUENCE: 22

Met Ala Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Ser Gly Ser Gly Asp Ser Thr Tyr His Ala Asp
50                  55                  60

Ser Val Lys Gly Arg Phe Thr Ile Ser Arg Asp Asn Ser Lys Asn Thr
65                  70                  75                  80

Leu Ser Leu Gln Met Asn Ser Leu Arg Ala Glu Asp Thr Ala Val Tyr
                85                  90                  95

Tyr Cys Ala Lys Asp Leu Asn Tyr Gly Ile Leu Thr Gly Tyr Tyr Asp
            100                 105                 110

Val Asp Tyr Trp Gly Gln Gly Thr Leu Val Thr Val Ser Ser Glu Leu
        115                 120                 125

Lys Thr Pro Leu Gly
    130

<210> SEQ ID NO 23
<211> LENGTH: 133
<212> TYPE: PRT
<213> ORGANISM: Homo sapiens

<400> SEQUENCE: 23

Met Ala Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Ser Gly Ser Gly Asp Ser Thr Tyr Asn Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Leu Asn Tyr Gly Ile Leu Thr Gly Tyr Tyr Asp
            100                 105                 110

Val Asp Tyr Trp Gly Gln Gly Thr Leu Val Thr Val Ser Ser Glu Leu
        115                 120                 125

Lys Thr Pro Leu Gly
    130

<210> SEQ ID NO 24
<211> LENGTH: 131
<212> TYPE: PRT
<213> ORGANISM: Homo sapiens

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Tyr Asn Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Asn Tyr Gly Ile Leu Thr Gly Tyr Tyr Asp Val Asp
            100                 105                 110

Tyr Trp Gly Gln Gly Thr Leu Val Thr Val Ser Ser Glu Leu Lys Thr
        115                 120                 125

Pro Leu Gly
    130

<210> SEQ ID NO 25
<211> LENGTH: 124
<212> TYPE: PRT
<213> ORGANISM: Homo sapiens

<400> SEQUENCE: 25

Glu Val Gln Leu Leu Glu Ser Gly Gly Gly Leu Val Gln Pro Gly Gly

```
1               5                   10                  15
Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Gly Ser Gly Gly Ser Thr Tyr Tyr Ala Asp Ser Val Lys Gly Arg
        50                  55                  60

Phe Thr Ile Ser Arg Asp Asn Ser Lys Asn Thr Leu Tyr Leu Gln Met
65                  70                  75                  80

Asn Ser Leu Arg Ala Glu Asp Thr Ala Val Tyr Tyr Cys Ala Lys Asp
                85                  90                  95

Tyr Tyr Tyr Gly Ser Gly Ile Phe Asp Tyr Trp Gly Gln Gly Thr Leu
                100                 105                 110

Val Thr Val Ser Ser Glu Arg Lys Cys Cys Val Glu
            115                 120
```

<210> SEQ ID NO 26
<211> LENGTH: 124
<212> TYPE: PRT
<213> ORGANISM: Homo sapiens

<400> SEQUENCE: 26

```
Glu Ala Gln Leu Leu Glu Ser Gly Gly Gly Leu Val Gln Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Gly Ser Gly Gly Ser Thr Tyr Tyr Ala Asp Ser Val Lys Gly Arg
        50                  55                  60

Phe Thr Ile Ser Arg Asp Asn Ser Asn Asn Thr Leu Tyr Leu Gln Met
65                  70                  75                  80

Asn Ser Leu Arg Ala Glu Asp Thr Ala Val Tyr Tyr Cys Ala Lys Asp
                85                  90                  95

Tyr Tyr Tyr Gly Ser Gly Ile Phe Asp Tyr Trp Gly Gln Gly Thr Leu
                100                 105                 110

Val Thr Val Ser Ser Glu Arg Lys Cys Cys Val Glu
            115                 120
```

<210> SEQ ID NO 27
<211> LENGTH: 124
<212> TYPE: PRT
<213> ORGANISM: Homo sapiens

<400> SEQUENCE: 27

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ile Trp Val Arg Gln Ala Pro Gly Lys Gly Leu Glu Trp Val
            35                  40                  45

Ser His Ser Gly Ser Thr Thr Tyr Tyr Ala Asp Ser Val Lys Gly Arg
        50                  55                  60

Phe Thr Ile Ser Arg Asp Asn Ser Lys Ser Thr Leu Tyr Leu Gln Met
65                  70                  75                  80

Asn Ser Leu Arg Ala Glu Asp Thr Ala Val Tyr Tyr Cys Ala Lys Asp
```

```
                    85                  90                  95
Tyr Tyr Tyr Gly Ser Gly Ile Phe Asp Tyr Trp Gly Gln Gly Thr Leu
                100                 105                 110

Val Thr Val Ser Ser Glu Arg Lys Cys Cys Val Glu
                115                 120

<210> SEQ ID NO 28
<211> LENGTH: 124
<212> TYPE: PRT
<213> ORGANISM: Homo sapiens

<400> SEQUENCE: 28

Glu Val Gln Leu Leu Glu Ser Gly Gly Gly Leu Val Gln Pro Gly Gly
1               5                   10                  15

Ser Pro Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Gly Ser Gly Gly Ser Thr Tyr Tyr Ala Asp Ser Val Lys Gly Arg
    50                  55                  60

Phe Thr Ile Ser Arg Asp Asn Ser Lys Asn Thr Leu Tyr Leu Gln Met
65                  70                  75                  80

Asn Ser Leu Arg Ala Glu Asp Thr Ala Val Tyr Tyr Cys Ala Lys Asp
                85                  90                  95

Tyr Tyr Tyr Gly Ser Gly Ile Phe Asp Tyr Trp Gly Gln Gly Thr Leu
                100                 105                 110

Val Thr Val Ser Ser Glu Arg Lys Cys Cys Val Glu
                115                 120

<210> SEQ ID NO 29
<211> LENGTH: 124
<212> TYPE: PRT
<213> ORGANISM: Homo sapiens

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Gly Ser Gly Gly Ser Thr Tyr Tyr Ala Asp Ser Val Lys Gly Arg
    50                  55                  60

Phe Thr Ile Ser Arg Asp Asn Ser Lys Asn Thr Leu Tyr Leu Gln Met
65                  70                  75                  80

Asn Ser Leu Arg Ala Glu Asp Thr Ala Val Tyr Tyr Cys Ala Lys Asp
                85                  90                  95

Tyr Tyr Tyr Gly Ser Gly Ile Phe Asp Tyr Trp Gly Gln Gly Thr Leu
                100                 105                 110

Val Thr Val Ser Ser Glu Arg Lys Cys Cys Val Glu
                115                 120

<210> SEQ ID NO 30
<211> LENGTH: 124
<212> TYPE: PRT
<213> ORGANISM: Homo sapiens

<400> SEQUENCE: 30
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Ser Gly Asp Ser Thr His Tyr Ala Asp Ser Val Lys Gly Arg
    50                  55                  60

Phe Thr Ile Ser Arg Asp Asn Ser Lys Asn Thr Leu Tyr Leu Gln Met
65                  70                  75                  80

Asn Ser Leu Arg Ala Glu Asp Thr Ala Val Tyr Tyr Cys Ala Lys Asp
            85                  90                  95

Phe Tyr Tyr Gly Ser Gly Ile Phe Asp Tyr Trp Gly Gln Gly Thr Leu
            100                 105                 110

Val Thr Val Ser Ser Glu Arg Lys Cys Cys Val Glu
            115                 120

<210> SEQ ID NO 31
<211> LENGTH: 96
<212> TYPE: PRT
<213> ORGANISM: Homo sapiens

<400> SEQUENCE: 31

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

<210> SEQ ID NO 32
<211> LENGTH: 128
<212> TYPE: PRT
<213> ORGANISM: Homo sapiens

<400> SEQUENCE: 32

Leu Ala Arg Gln Leu Leu Glu Ser Gly Gly Gly Leu Val Lys Pro Gly
1               5                   10                  15

Gly Ser Gln Arg Leu Ser Cys Ala Ala Ser Gly Phe Thr Phe Ser Asp
            20                  25                  30

Tyr Tyr Met Ser Trp Val Arg Gln Ala Pro Gly Lys Gly Leu Gln Trp
        35                  40                  45

Ile Ser Tyr Ile Ser Gly Asn Gly Arg Thr Ile Tyr Tyr Ala Asp Ser
    50                  55                  60

Val Lys Gly Arg Phe Thr Ile Ser Arg Asp Asn Ala Arg Asn Ser Leu
65                  70                  75                  80

Tyr Leu Gln Met Asn Ser Leu Arg Ala Glu Asp Thr Ala Val Tyr Tyr
            85                  90                  95

Cys Thr Arg Gly Gly Thr Val Asp Pro Tyr Thr Phe Asp Ile Trp Gly
            100                 105                 110
```

Gln Gly Thr Met Val Thr Val Ser Ser Glu Leu Lys Thr Pro Leu Gly
            115                 120                 125

<210> SEQ ID NO 33
<211> LENGTH: 127
<212> TYPE: PRT
<213> ORGANISM: Homo sapiens

<400> SEQUENCE: 33

Gln Val Gln Leu Val Glu Ser Gly Gly Gly Leu Val Lys Pro Gly Gly
1               5                   10                  15

Ser Gln Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Gln Trp Ile
        35                  40                  45

Ser Tyr Ile Ser Gly Asn Gly Arg Thr Ile Tyr Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Gly Gly Thr Val Asp Pro Tyr Thr Phe Asp Ile Trp Gly Gln
            100                 105                 110

Gly Thr Met Val Thr Val Ser Ser Glu Leu Lys Thr Pro Leu Gly
        115                 120                 125

<210> SEQ ID NO 34
<211> LENGTH: 129
<212> TYPE: PRT
<213> ORGANISM: Homo sapiens

<400> SEQUENCE: 34

Leu Asp Glu Val Lys Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Asp Tyr Tyr Val Ser Trp Ile Arg Gln Ala Pro Gly Lys Gly Leu Gln
        35                  40                  45

Trp Ile Ser Tyr Ile Ser Ser Ser Gly Ser Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Phe Leu Gln Met Asn Ser Leu Arg Ala Glu Asp Thr Ala Val Tyr
                85                  90                  95

Tyr Cys Thr Arg Gly Gly Thr Glu Asp Pro Tyr Thr Phe Asp Ile Trp
            100                 105                 110

Gly Gln Gly Thr Met Val Thr Val Ser Ser Glu Leu Lys Thr Pro Leu
        115                 120                 125

Gly

<210> SEQ ID NO 35
<211> LENGTH: 133
<212> TYPE: PRT
<213> ORGANISM: Homo sapiens

<400> SEQUENCE: 35

Met Ala Glu Val Gln Leu Val Glu Ser Gly Gly Gly Leu Val Lys Pro

```
1               5                   10                  15
Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Pro Gly Lys Gly Leu Glu
            35                  40                  45

Trp Val Ser Tyr Ile Ser Ser Gly Arg Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Gly Met Val Arg Gly Val Thr Asp Tyr Tyr Asp
                100                 105                 110

Leu Asp Val Trp Gly Gln Gly Thr Thr Val Thr Val Ser Ser Glu Leu
                115                 120                 125

Lys Thr Pro Leu Gly
        130
```

<210> SEQ ID NO 36
<211> LENGTH: 133
<212> TYPE: PRT
<213> ORGANISM: Homo sapiens

<400> SEQUENCE: 36

```
Met Ala Gln Val Lys Leu Val Glu Ser Gly Gly Gly Leu Val Glu Pro
1               5                   10                  15

Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Pro Gly Lys Gly Leu Glu
            35                  40                  45

Trp Val Ser Tyr Ile Ser Ser Gly Arg Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Gly Leu Arg Ala Glu Asp Thr Ala Val Tyr
                85                  90                  95

Tyr Cys Ala Arg Asp Gly Met Val Arg Gly Val Thr Asp Tyr Tyr Asp
                100                 105                 110

Leu Asp Val Trp Gly Gln Gly Thr Thr Val Thr Val Ser Ser Glu Leu
                115                 120                 125

Lys Thr Pro Leu Gly
        130
```

<210> SEQ ID NO 37
<211> LENGTH: 128
<212> TYPE: PRT
<213> ORGANISM: Homo sapiens

<400> SEQUENCE: 37

```
Met Ala Gln Val Lys Leu Leu Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Gln Gly Lys Gly Leu Glu
            35                  40                  45

Trp Val Ser Tyr Ile Ser Ser Ser Gly Arg Thr Ile Tyr Tyr Ala Thr
```

```
                 50                  55                  60
Ser Val Lys Gly Arg Phe Thr Ile Ser Arg Thr His Ala Lys Asn Ser
 65                  70                  75                  80

Leu Tyr Leu Gln Met Asn Ser Leu Arg Ala Lys Asp Thr Ala Val Tyr
                 85                  90                  95

Tyr Cys Ala Arg Asp Gly Met Val Arg Gly Val Thr Asp Tyr Tyr Asp
                100                 105                 110

Leu Asp Val Trp Gly Gln Gly Thr Thr Val Thr Val Ser Ser Glu Leu
            115                 120                 125

<210> SEQ ID NO 38
<211> LENGTH: 133
<212> TYPE: PRT
<213> ORGANISM: Homo sapiens

<400> SEQUENCE: 38

Met Ala Glu Val Gln Leu Leu Glu Ser Gly Gly Gly Leu Val Lys Pro
 1               5                  10                  15

Gly Gly Ser Leu Arg Leu Ser Cys Ala Ala Ser Gly Phe Thr Phe Ser
                 20                  25                  30

Asp Tyr Tyr Met Ser Trp Ile Arg Gln Ala Pro Gly Lys Gly Leu Glu
            35                  40                  45

Trp Val Ser Tyr Ile Ser Ser Gly Arg Thr Ile Tyr Tyr Ala Asp
 50                  55                  60

Ser Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                 85                  90                  95

Tyr Cys Ala Arg Asp Gly Met Val Arg Gly Val Thr Asp Tyr Tyr Asp
                100                 105                 110

Leu Asp Val Trp Gly Gln Gly Thr Thr Val Thr Val Ser Ser Glu Leu
            115                 120                 125

Lys Thr Pro Leu Gly
        130

<210> SEQ ID NO 39
<211> LENGTH: 133
<212> TYPE: PRT
<213> ORGANISM: Homo sapiens

<400> SEQUENCE: 39

Met Ala Glu Val Lys Leu Leu Gln Ser Gly Gly Gly Leu Val Lys Pro
 1               5                  10                  15

Gly Gly Ser Leu Arg Leu Ser Cys Ala Ala Ser Gly Phe Thr Phe Ser
                 20                  25                  30

Asp Tyr Tyr Met Ser Trp Ile Arg Gln Ala Pro Gly Lys Gly Pro Glu
            35                  40                  45

Trp Val Ser Tyr Ile Ser Ser Gly Arg Thr Ile Tyr Tyr Ala Asp
 50                  55                  60

Ser Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                 85                  90                  95

Tyr Cys Ala Arg Asp Gly Met Phe Arg Gly Val Thr Asp Tyr Tyr Asp
                100                 105                 110

Leu Asp Val Trp Gly Gln Gly Thr Thr Val Thr Val Ser Ser Glu Leu
```

```
                       115                 120                 125

Lys Thr Pro Leu Gly
        130

<210> SEQ ID NO 40
<211> LENGTH: 133
<212> TYPE: PRT
<213> ORGANISM: Homo sapiens

<400> SEQUENCE: 40

Met Ala Gln Val Gln Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Pro Gly Lys Gly Leu Glu
        35                  40                  45

Trp Val Ser Tyr Ile Ser Ser Gly Arg Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Gly Met Val Arg Gly Val Thr Asp Tyr Tyr Asp
            100                 105                 110

Leu Asp Val Trp Gly Gln Gly Thr Thr Val Thr Val Ser Pro Glu Leu
        115                 120                 125

Lys Thr Pro Leu Gly
        130

<210> SEQ ID NO 41
<211> LENGTH: 133
<212> TYPE: PRT
<213> ORGANISM: Homo sapiens

<400> SEQUENCE: 41

Met Ala Gln Val Lys Leu Leu Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Pro Gly Lys Gly Leu Glu
        35                  40                  45

Trp Val Ser Tyr Ile Ser Ser Ser Gly Arg Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Gly Met Phe Arg Gly Val Thr Asp Tyr Tyr Asp
            100                 105                 110

Leu Asp Val Trp Gly Gln Gly Thr Thr Val Thr Val Ser Ser Glu Leu
        115                 120                 125

Lys Thr Pro Leu Gly
        130

<210> SEQ ID NO 42
<211> LENGTH: 133
<212> TYPE: PRT
```

<213> ORGANISM: Homo sapiens

<400> SEQUENCE: 42

Met Ala Glu Val Gln Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Pro Gly Lys Gly Leu Glu
        35                  40                  45

Trp Val Ser Tyr Ile Ser Ser Ser Gly Arg Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Gly Met Val Arg Gly Val Thr Asp Tyr Tyr Asp
            100                 105                 110

Leu Asp Val Trp Gly Gln Gly Thr Thr Val Thr Val Ser Ser Glu Leu
        115                 120                 125

Lys Thr Pro Leu Gly
    130

<210> SEQ ID NO 43
<211> LENGTH: 133
<212> TYPE: PRT
<213> ORGANISM: Homo sapiens

<400> SEQUENCE: 43

Met Ala Glu Val Gln Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Pro Gly Lys Gly Leu Glu
        35                  40                  45

Trp Val Ser Tyr Ile Ser Ser Ser Gly Arg Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Gly Met Val Arg Gly Val Thr Asp Tyr Tyr Asp
            100                 105                 110

Leu Asp Val Trp Gly Gln Gly Thr Thr Asp Thr Val Ser Ser Glu Leu
        115                 120                 125

Lys Thr Pro Leu Gly
    130

<210> SEQ ID NO 44
<211> LENGTH: 133
<212> TYPE: PRT
<213> ORGANISM: Homo sapiens

<400> SEQUENCE: 44

Met Ala Glu Val Lys Leu Val Gln Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Pro Gly Lys Gly Leu Glu
            35                  40                  45

Trp Val Ser Tyr Ile Ser Ser Gly Arg Thr Ile Tyr Tyr Ala Asp
    50                  55                  60

Ser Val Lys Gly Arg Phe Thr Ile Ser Arg Asp Asn Ala Lys Ser Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Gly Met Val Arg Gly Val Thr Asp Tyr Tyr Asp
                100                 105                 110

Leu Asp Val Trp Gly Gln Gly Thr Thr Val Thr Val Ser Ser Glu Leu
            115                 120                 125

Lys Thr Pro Leu Gly
        130

<210> SEQ ID NO 45
<211> LENGTH: 133
<212> TYPE: PRT
<213> ORGANISM: Homo sapiens

<400> SEQUENCE: 45

Met Ala Glu Val Gln Leu Val Gln Ser Gly Gly Gly Leu Val Arg Pro
1               5                   10                  15

Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Pro Gly Lys Gly Leu Glu
            35                  40                  45

Trp Val Ser Tyr Ile Ser Ser Gly Arg Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Gly Met Val Arg Gly Val Thr Asp Tyr Tyr Asp
                100                 105                 110

Leu Asp Val Trp Gly Gln Gly Thr Thr Val Thr Val Ser Ser Glu Leu
            115                 120                 125

Lys Thr Pro Leu Gly
        130

<210> SEQ ID NO 46
<211> LENGTH: 133
<212> TYPE: PRT
<213> ORGANISM: Homo sapiens

<400> SEQUENCE: 46

Met Ala Glu Val Lys Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Pro Gly Lys Gly Leu Glu
            35                  40                  45

Trp Val Ser Tyr Ile Ser Ser Gly Ser Thr Ile Tyr Tyr Ala Asp
    50                  55                  60

Ser Val Lys Gly Arg Phe Thr Ile Ser Arg Asp Asn Ala Lys Asn Ser
65                  70                  75                  80

```
Leu Tyr Leu Gln Met Asn Ser Leu Arg Ala Glu Asp Thr Ala Val Tyr
                85                  90                  95

Tyr Cys Ala Arg Asp Gly Met Val Arg Gly Val Thr Asp Tyr Tyr Asp
            100                 105                 110

Leu Asp Val Trp Gly Gln Gly Thr Thr Val Thr Val Ser Ser Glu Leu
        115                 120                 125

Lys Thr Pro Leu Gly
        130

<210> SEQ ID NO 47
<211> LENGTH: 133
<212> TYPE: PRT
<213> ORGANISM: Homo sapiens
<220> FEATURE:
<221> NAME/KEY: VARIANT
<222> LOCATION: 84, 85, 120
<223> OTHER INFORMATION: Xaa = Any Amino Acid

<400> SEQUENCE: 47

Met Ala Glu Val Lys Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Pro Gly Lys Gly Leu Glu
        35                  40                  45

Trp Val Ser Tyr Ile Ser Ser Gly Arg Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Xaa Xaa Asn Ser Leu Arg Ala Glu Asp Thr Ala Val Tyr
                85                  90                  95

Tyr Cys Ala Arg Asp Gly Met Val Arg Gly Val Thr Asp Tyr Tyr Asp
            100                 105                 110

Leu Asp Val Trp Gly Gln Gly Xaa Thr Val Thr Val Ser Ser Glu Leu
        115                 120                 125

Lys Thr Pro Leu Gly
        130

<210> SEQ ID NO 48
<211> LENGTH: 133
<212> TYPE: PRT
<213> ORGANISM: Homo sapiens

<400> SEQUENCE: 48

Met Ala Glu Val Lys Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Pro Gly Lys Gly Leu Glu
        35                  40                  45

Trp Val Ser Tyr Ile Ser Ser Gly Arg Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Gly Met Val Arg Gly Val Thr Asp Tyr Tyr Asp
```

100                 105                 110
Leu Asp Val Trp Gly Gln Gly Thr Thr Val Thr Val Ser Ser Glu Leu
            115                 120                 125
Lys Thr Pro Leu Gly
        130

<210> SEQ ID NO 49
<211> LENGTH: 133
<212> TYPE: PRT
<213> ORGANISM: Homo sapiens

<400> SEQUENCE: 49

Met Ala Glu Val Lys Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Asp Tyr Tyr Met Gly Trp Ile Arg Gln Ala Pro Gly Lys Gly Leu Glu
        35                  40                  45

Trp Val Ser Tyr Ile Ser Ser Ser Gly Arg Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Gly Met Val Arg Gly Val Thr Asp Tyr Tyr Asp
            100                 105                 110

Leu Asp Val Trp Gly Gln Gly Thr Thr Val Thr Val Ser Ser Glu Leu
        115                 120                 125

Lys Thr Pro Leu Gly
    130

<210> SEQ ID NO 50
<211> LENGTH: 133
<212> TYPE: PRT
<213> ORGANISM: Homo sapiens

<400> SEQUENCE: 50

Met Ala Glu Val Lys Leu Val Glu Ser Gly Gly Gly Leu Val Lys Pro
1               5                   10                  15

Gly Gly Ser Leu Arg Leu Ser Cys Thr Ala Ser Gly Phe Thr Phe Ser
            20                  25                  30

Asp Tyr Tyr Met Ser Trp Ile Arg Gln Ala Pro Gly Lys Gly Leu Glu
        35                  40                  45

Trp Val Ser Tyr Ile Ser Ser Ser Gly Arg Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Gly Met Val Arg Gly Val Thr Asp Tyr Tyr Asp
            100                 105                 110

Leu Asp Val Trp Gly Gln Gly Thr Thr Val Thr Val Ser Ser Glu Leu
        115                 120                 125

Lys Thr Pro Leu Gly
    130

```
<210> SEQ ID NO 51
<211> LENGTH: 132
<212> TYPE: PRT
<213> ORGANISM: Homo sapiens

<400> SEQUENCE: 51

Met Ala Glu Val Lys Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Asp Tyr Tyr Met Ser Ile Arg Gln Ala Pro Gly Lys Gly Leu Glu Trp
        35                  40                  45

Val Ser Tyr Ile Ser Ser Ser Gly Arg Thr Ile Tyr Tyr Ala Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Asp Gly Met Val Arg Gly Val Thr Asp Tyr Tyr Asp Leu
            100                 105                 110

Asp Val Trp Gly Gln Gly Thr Thr Val Thr Val Ser Ser Glu Leu Lys
        115                 120                 125

Thr Pro Leu Gly
    130

<210> SEQ ID NO 52
<211> LENGTH: 132
<212> TYPE: PRT
<213> ORGANISM: Homo sapiens

<400> SEQUENCE: 52

Met Ala Gln Val Gln Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Pro Gly Lys Gly Leu Glu
        35                  40                  45

Trp Val Ser Tyr Ile Ser Ser Ser Gly Ser Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Gly Gly Pro His Asn Ser Arg Ser Tyr His Pro Leu
            100                 105                 110

Asp Tyr Trp Gly Gln Gly Thr Leu Val Thr Val Ser Ser Glu Arg Lys
        115                 120                 125

Cys Cys Val Glu
    130

<210> SEQ ID NO 53
<211> LENGTH: 128
<212> TYPE: PRT
<213> ORGANISM: Homo sapiens

<400> SEQUENCE: 53

Met Ala Glu Val Gln Leu Val Glu Ser Gly Gly Gly Leu Val Lys Pro
1               5                   10                  15
```

Gly Gly Ser Leu Arg Leu Ser Cys Ala Ala Ser Gly Phe Thr Leu Ser
            20                  25                  30

Asp Tyr Tyr Met Ser Trp Ile Arg Gln Ala Pro Gly Lys Gly Leu Glu
        35                  40                  45

Trp Ile Ser Tyr Ile Ser Ser Gly Thr Ile Arg Asn Tyr Ala Asp
 50                  55                  60

Ser Val Lys Gly Arg Phe Thr Ile Ser Arg Asp Asn Ala Lys Asn Ser
 65                  70                  75                  80

Met Tyr Leu Gln Met Asn Ser Leu Arg Ala Glu Asp Thr Ala Val Tyr
                85                  90                  95

Tyr Cys Thr Arg Gly Trp Gly Ser Asp Glu Ala Leu Asp Ile Trp Gly
            100                 105                 110

Pro Gly Thr Met Val Thr Val Ser Ser Glu Leu Lys Thr Pro Leu Gly
        115                 120                 125

<210> SEQ ID NO 54
<211> LENGTH: 129
<212> TYPE: PRT
<213> ORGANISM: Homo sapiens

<400> SEQUENCE: 54

Met Ala Gln Val Gln Leu Val Glu Ser Gly Gly Gly Leu Val Lys Pro
 1               5                   10                  15

Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Pro Gly Lys Gly Leu Gln
        35                  40                  45

Trp Leu Ser Tyr Ile Ser Gly Ser Gly Ser Thr Ile Tyr Tyr Ala Asp
 50                  55                  60

Ser Val Lys Gly Arg Phe Thr Ile Ser Arg Asp Asn Ala Lys Asn Ser
 65                  70                  75                  80

Leu Ser Leu Gln Met Asn Ser Leu Arg Ala Glu Asp Thr Ala Val Tyr
                85                  90                  95

Tyr Cys Ala Arg Gly Gly Thr Val Asp Pro Tyr Thr Phe Asp Ile Trp
            100                 105                 110

Gly Gln Gly Thr Met Val Thr Val Ser Ser Glu Leu Lys Thr Pro Leu
        115                 120                 125

Gly

<210> SEQ ID NO 55
<211> LENGTH: 129
<212> TYPE: PRT
<213> ORGANISM: Homo sapiens

<400> SEQUENCE: 55

Met Ala Gln Val Gln Leu Val Glu Ser Gly Gly Gly Leu Val Lys Pro
 1               5                   10                  15

Gly Gly Ser Leu Arg Leu Ser Cys Ala Ala Ser Gly Phe Thr Phe Ser
            20                  25                  30

Asp Tyr Tyr Met Ser Trp Ile Arg Gln Ala Pro Gly Lys Gly Leu Gln
        35                  40                  45

Trp Leu Ser Tyr Ile Ser Ser Ser Gly Ser Thr Ile Tyr Tyr Ala Asp
 50                  55                  60

Ser Val Lys Gly Arg Phe Thr Ile Ser Arg Asp Asn Ala Lys Asn Ser
 65                  70                  75                  80

Leu Phe Leu Gln Ile Asn Ser Leu Arg Ala Glu Asp Thr Ala Val Tyr
            85                  90                  95

Tyr Cys Ala Arg Gly Gly Thr Val Asp Pro Tyr Thr Phe Asp Ile Trp
        100                 105                 110

Gly Gln Gly Thr Met Val Thr Val Ser Ser Glu Leu Lys Thr Pro Leu
        115                 120                 125

Gly

<210> SEQ ID NO 56
<211> LENGTH: 123
<212> TYPE: PRT
<213> ORGANISM: Homo sapiens

<400> SEQUENCE: 56

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Ile Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Val Pro Ala Thr Asp Ser Trp Gly Gln Gly Thr Leu Val
        100                 105                 110

Thr Val Ser Ser Glu Arg Lys Cys Cys Val Glu
        115                 120

<210> SEQ ID NO 57
<211> LENGTH: 127
<212> TYPE: PRT
<213> ORGANISM: Homo sapiens

<400> SEQUENCE: 57

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Asn Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Leu Gly Met Val Arg Pro Leu His Tyr Trp Gly Gln
        100                 105                 110

Gly Thr Leu Val Thr Val Ser Ser Glu Arg Lys Cys Cys Val Glu
        115                 120                 125

<210> SEQ ID NO 58
<211> LENGTH: 127
<212> TYPE: PRT

-continued

<213> ORGANISM: Homo sapiens

<400> SEQUENCE: 58

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Asn Ser Gly Asn Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Leu Gly Met Val Arg Pro Leu His Tyr Trp Gly Gln
            100                 105                 110

Gly Thr Leu Val Thr Val Ser Ser Glu Arg Lys Cys Cys Val Glu
        115                 120                 125

<210> SEQ ID NO 59
<211> LENGTH: 127
<212> TYPE: PRT
<213> ORGANISM: Homo sapiens

<400> SEQUENCE: 59

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Gly Ser Gly Asn Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Leu Gly Met Val Arg Pro Leu His Tyr Trp Gly Gln
            100                 105                 110

Gly Thr Leu Val Thr Val Ser Ser Glu Arg Lys Cys Cys Val Glu
        115                 120                 125

<210> SEQ ID NO 60
<211> LENGTH: 127
<212> TYPE: PRT
<213> ORGANISM: Homo sapiens

<400> SEQUENCE: 60

Glu Val Gln Leu Val Glu Ser Gly Gly Asp Leu Val Glu Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Gly Ser Gly Asn Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Leu Gly Met Val Arg Pro Leu His Tyr Trp Gly Gln
            100                 105                 110

Gly Thr Leu Val Thr Val Ser Ser Glu Arg Lys Cys Cys Val Glu
        115                 120                 125

<210> SEQ ID NO 61
<211> LENGTH: 127
<212> TYPE: PRT
<213> ORGANISM: Homo sapiens

<400> SEQUENCE: 61

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Asn Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Leu Gly Met Val Arg Pro Leu His Tyr Trp Gly Gln
            100                 105                 110

Gly Thr Leu Val Thr Val Ser Ser Glu Leu Lys Thr Pro Leu Gly
        115                 120                 125

<210> SEQ ID NO 62
<211> LENGTH: 127
<212> TYPE: PRT
<213> ORGANISM: Homo sapiens

<400> SEQUENCE: 62

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Gly Ser Gly Asn Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Leu Gly Met Val Arg Pro Leu His Tyr Trp Gly Gln
            100                 105                 110

Gly Thr Leu Val Thr Val Ser Ser Glu Leu Lys Thr Pro Leu Gly
        115                 120                 125

<210> SEQ ID NO 63

```
<211> LENGTH: 127
<212> TYPE: PRT
<213> ORGANISM: Homo sapiens

<400> SEQUENCE: 63

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Gly Ser Gly Asn Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Leu Gly Met Asp Arg Pro Leu His Tyr Trp Gly Gln
            100                 105                 110

Gly Thr Leu Val Thr Val Ser Ser Glu Leu Lys Thr Pro Leu Gly
        115                 120                 125

<210> SEQ ID NO 64
<211> LENGTH: 127
<212> TYPE: PRT
<213> ORGANISM: Homo sapiens

<400> SEQUENCE: 64

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Gly Ser Gly Asn Thr Ile Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Arg Ala Gly Met Val Arg Gly Pro His Tyr Trp Gly Gln
            100                 105                 110

Gly Thr Leu Val Thr Val Ser Ser Glu Leu Lys Thr Pro Leu Gly
        115                 120                 125

<210> SEQ ID NO 65
<211> LENGTH: 127
<212> TYPE: PRT
<213> ORGANISM: Homo sapiens

<400> SEQUENCE: 65

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45
```

Ser Tyr Ile Ser Ser Ser Gly Ser Thr Ile Tyr Tyr Ala Asp Ser Val
        50                      55                      60

Lys Gly Arg Phe Thr Ile Ser Arg Asp Asn Ala Lys Asn Ser Leu Tyr
65                      70                      75                      80

Leu Gln Met Asn Ser Leu Arg Ala Glu Asp Thr Ala Val Tyr Tyr Cys
                      85                      90                      95

Ala Arg Arg Arg Ser Leu Thr Val Gly Ala Pro Thr Tyr Trp Gly Gln
                    100                   105                   110

Gly Thr Leu Val Thr Val Ser Ser Glu Arg Lys Cys Cys Val Glu
               115                   120                   125

<210> SEQ ID NO 66
<211> LENGTH: 127
<212> TYPE: PRT
<213> ORGANISM: Homo sapiens

<400> SEQUENCE: 66

Glu Val Gln Leu Val Glu Ser Gly Gly Gly Leu Val Lys Pro Gly Gly
1                      5                      10                      15

Ser Leu Arg Leu Ser Cys Ala Ala Ser Gly Phe Thr Phe Ser Asp Tyr
                    20                      25                      30

Tyr Met Ser Trp Ile Arg Gln Ala Pro Gly Lys Gly Leu Glu Trp Val
               35                      40                      45

Ser Tyr Ile Ser Ser Ser Gly Ser Thr Ile Tyr Tyr Ala Asp Ser Val
        50                      55                      60

Arg Gly Arg Phe Thr Ile Ser Arg Asp Asn Ala Lys Asp Ser Leu Tyr
65                      70                      75                      80

Leu Gln Met Asn Ser Leu Arg Ala Glu Asp Thr Ala Val Tyr Tyr Cys
                      85                      90                      95

Ala Arg Arg Ser Leu Thr Val Gly Ala Pro Thr Tyr Trp Gly Gln
                    100                   105                   110

Gly Thr Leu Val Thr Val Ser Ser Glu Arg Lys Cys Cys Val Glu
               115                   120                   125

<210> SEQ ID NO 67
<211> LENGTH: 127
<212> TYPE: PRT
<213> ORGANISM: Homo sapiens

<400> SEQUENCE: 67

Glu Val Gln Leu Val Glu Ser Gly Gly Gly Leu Val Lys Pro Gly Gly
1                      5                      10                      15

Ser Leu Arg Leu Ser Cys Ala Ala Ser Gly Phe Thr Phe Ser Asp Tyr
                    20                      25                      30

Tyr Met Ser Trp Ile Arg Gln Ala Pro Gly Lys Gly Leu Glu Trp Val
               35                      40                      45

Ser Tyr Ile Ser Ser Ser Gly Ser Thr Ile Tyr Tyr Ala Asp Ser Val
        50                      55                      60

Lys Gly Arg Phe Thr Ile Ser Arg Asp Asn Ala Lys Asp Ser Leu Tyr
65                      70                      75                      80

Leu Gln Met Asn Ser Leu Arg Ala Glu Asp Thr Ala Val Tyr Tyr Cys
                      85                      90                      95

Ala Arg Arg Arg Ser Leu Thr Val Gly Ala Pro Thr Tyr Trp Gly Gln
                    100                   105                   110

Gly Thr Leu Val Thr Val Ser Ser Glu Arg Lys Cys Cys Val Glu
               115                   120                   125

<210> SEQ ID NO 68
<211> LENGTH: 127
<212> TYPE: PRT
<213> ORGANISM: Homo sapiens

<400> SEQUENCE: 68

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Ile Ile Tyr Tyr Ala Asp Ser Val
    50                  55                  60

Lys Gly Arg Phe Thr Ile Ser Arg Asp Asn Ala Lys Asp Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Arg Ser Leu Thr Val Gly Ala Pro Thr Tyr Trp Gly Gln
            100                 105                 110

Gly Thr Leu Val Thr Val Ser Ser Glu Arg Lys Cys Cys Val Glu
        115                 120                 125

<210> SEQ ID NO 69
<211> LENGTH: 127
<212> TYPE: PRT
<213> ORGANISM: Homo sapiens

<400> SEQUENCE: 69

Glu Val Gln Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asp Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Arg Ser Leu Thr Val Gly Ala Pro Thr Tyr Trp Gly Gln
            100                 105                 110

Gly Thr Leu Val Thr Val Ser Ser Glu Arg Lys Cys Cys Val Glu
        115                 120                 125

<210> SEQ ID NO 70
<211> LENGTH: 127
<212> TYPE: PRT
<213> ORGANISM: Homo sapiens

<400> SEQUENCE: 70

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val

```
            35                  40                  45
Ser Tyr Ile Ser Ser Ser Gly Ser Thr Leu Tyr Tyr Ala Asp Ser Val
 50                  55                  60

Arg Gly Arg Phe Thr Ile Ser Arg Asp Asn Ala Lys Asp Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Arg Ser Leu Thr Val Gly Ala Pro Thr Tyr Trp Gly Gln
                100                 105                 110

Gly Thr Leu Val Thr Val Ser Ser Glu Arg Lys Cys Cys Val Glu
                115                 120                 125

<210> SEQ ID NO 71
<211> LENGTH: 124
<212> TYPE: PRT
<213> ORGANISM: Homo sapiens

<400> SEQUENCE: 71

Glu Val Gln Leu Val Glu Ser Gly Gly Gly Leu Val Lys Ser Gly Gly
 1               5                  10                  15

Ser Leu Arg Leu Ser Cys Ala Ala Ser Gly Phe Thr Phe Ser Asp Tyr
                 20                  25                  30

Tyr Met Ser Trp Ile Arg Gln Ala Pro Gly Lys Gly Leu Glu Trp Val
             35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ile Ser Met Ala Arg Asp Tyr Trp Gly Gln Gly Thr Leu
                100                 105                 110

Val Thr Val Ser Ser Glu Arg Lys Cys Cys Val Glu
                115                 120

<210> SEQ ID NO 72
<211> LENGTH: 124
<212> TYPE: PRT
<213> ORGANISM: Homo sapiens

<400> SEQUENCE: 72

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                 20                  25                  30

Tyr Met Ser Trp Ile Arg Gln Thr Pro Gly Lys Gly Leu Glu Trp Val
             35                  40                  45

Ser Tyr Ile Ser Ser Ser Gly Asn Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ile Ser Met Ala Arg Asp Ser Trp Gly Gln Gly Thr Leu
                100                 105                 110

Val Thr Val Ser Ser Glu Arg Lys Cys Cys Val Glu
```

-continued

```
              115                 120
```

<210> SEQ ID NO 73
<211> LENGTH: 124
<212> TYPE: PRT
<213> ORGANISM: Homo sapiens

<400> SEQUENCE: 73

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Ser Met Val Arg Asp Tyr Trp Gly Gln Gly Thr Pro
            100                 105                 110

Val Thr Val Ser Ser Glu Arg Lys Cys Cys Val Glu
        115                 120
```

<210> SEQ ID NO 74
<211> LENGTH: 124
<212> TYPE: PRT
<213> ORGANISM: Homo sapiens

<400> SEQUENCE: 74

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Ser Met Val Gly Asp Asn Trp Gly Gln Gly Thr Leu
            100                 105                 110

Val Thr Val Ser Ser Glu Arg Lys Cys Cys Val Glu
        115                 120
```

<210> SEQ ID NO 75
<211> LENGTH: 124
<212> TYPE: PRT
<213> ORGANISM: Homo sapiens

<400> SEQUENCE: 75

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30
```

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ile Ser Met Val Gly Asp Tyr Trp Gly Gln Gly Thr Leu
             100                 105                 110

Val Thr Val Ser Ser Glu Arg Lys Cys Cys Val Glu
             115                 120

<210> SEQ ID NO 76
<211> LENGTH: 124
<212> TYPE: PRT
<213> ORGANISM: Homo sapiens

<400> SEQUENCE: 76

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ile Ser Met Ala Gly Asp Ser Trp Gly Gln Gly Thr Leu
             100                 105                 110

Val Thr Val Ser Ser Glu Arg Lys Cys Cys Val Glu
             115                 120

<210> SEQ ID NO 77
<211> LENGTH: 124
<212> TYPE: PRT
<213> ORGANISM: Homo sapiens

<400> SEQUENCE: 77

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ile Ser Met Thr Gly Asp Tyr Trp Gly Gln Gly Thr Leu
             100                 105                 110

-continued

```
Val Asn Val Ser Ser Glu Arg Lys Cys Cys Val Glu
        115                 120

<210> SEQ ID NO 78
<211> LENGTH: 124
<212> TYPE: PRT
<213> ORGANISM: Homo sapiens

<400> SEQUENCE: 78

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Gly Gly Asp Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Ser Met Thr Gly Asp Tyr Trp Gly Gln Gly Thr Leu
            100                 105                 110

Val Asn Val Ser Ser Glu Arg Lys Cys Cys Val Glu
        115                 120

<210> SEQ ID NO 79
<211> LENGTH: 124
<212> TYPE: PRT
<213> ORGANISM: Homo sapiens

<400> SEQUENCE: 79

Glu Val Gln Leu Val Glu Phe Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Asn Ile Tyr Tyr Ala Asp Ser Val
    50                  55                  60

Lys Gly Arg Phe Thr Ile Thr Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Ser Met Thr Gly Asp Tyr Trp Gly Gln Gly Thr Gln
            100                 105                 110

Val Thr Val Ser Ser Glu Arg Lys Cys Cys Val Glu
        115                 120

<210> SEQ ID NO 80
<211> LENGTH: 124
<212> TYPE: PRT
<213> ORGANISM: Homo sapiens

<400> SEQUENCE: 80

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Ile Ser Thr Thr Gly Asp Tyr Trp Gly Gln Gly Ala Leu
            100                 105                 110

Val Ser Val Ser Ser Asp Arg Lys Cys Cys Val Glu
            115                 120

<210> SEQ ID NO 81
<211> LENGTH: 124
<212> TYPE: PRT
<213> ORGANISM: Homo sapiens

<400> SEQUENCE: 81

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Ser Leu Thr Gly Asp Tyr Trp Gly Gln Gly Thr Leu
            100                 105                 110

Val Thr Val Ser Ser Glu Arg Lys Cys Cys Val Glu
            115                 120

<210> SEQ ID NO 82
<211> LENGTH: 124
<212> TYPE: PRT
<213> ORGANISM: Homo sapiens

<400> SEQUENCE: 82

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95
```

Ala Arg Gly Ile Ser Leu Thr Gly Thr Asp Trp Gly Gln Gly Thr Leu
            100                 105                 110

Val Thr Val Ser Ser Glu Arg Lys Cys Cys Val Glu
            115                 120

<210> SEQ ID NO 83
<211> LENGTH: 124
<212> TYPE: PRT
<213> ORGANISM: Homo sapiens

<400> SEQUENCE: 83

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Ile Ser Val Thr Gly Asp Ser Trp Gly Gln Gly Thr Leu
            100                 105                 110

Val Thr Val Ser Ser Glu Arg Lys Cys Cys Val Glu
            115                 120

<210> SEQ ID NO 84
<211> LENGTH: 117
<212> TYPE: PRT
<213> ORGANISM: Homo sapiens

<400> SEQUENCE: 84

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Arg Ala Pro Gly Lys Gly Leu Glu Trp Val
            35                  40                  45

Ser Tyr Ile Ser Ser Ser Gly Ser Asn Ile Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Ile Ala Met Thr Gly Asp Tyr Trp Gly Gln Gly Thr Gln
            100                 105                 110

Val Thr Val Thr Ser
            115

<210> SEQ ID NO 85
<211> LENGTH: 124
<212> TYPE: PRT
<213> ORGANISM: Homo sapiens

<400> SEQUENCE: 85

Glu Val Gln Leu Val Glu Ser Gly Gly Gly Leu Val Lys Pro Gly Gly

```
              1               5                  10                 15
Ser Leu Arg Leu Ser Cys Ala Ala Ser Gly Phe Thr Phe Ser Asp Tyr
                20                  25                 30

Tyr Met Ser Trp Ile Arg Gln Ala Pro Gly Lys Gly Leu Glu Trp Val
            35                  40                 45

Ser Tyr Ile Ser Ser Gly Ser Thr Ile Tyr Tyr Ala Asp Ser Val
        50                  55                 60

Lys Gly Arg Phe Thr Ile Ser Arg Asp Asn Ala Lys Asn Ser Leu Tyr
65                      70                 75                 80

Leu Gln Met Asn Ser Leu Arg Ala Glu Asp Thr Ala Val Tyr Tyr Cys
                85                  90                 95

Ala Arg Gly Ile Ala Met Val Glu Asp Ser Trp Gln Gly Thr Leu
                100                 105                110

Val Thr Val Ser Ser Glu Arg Lys Cys Cys Val Glu
        115                 120
```

<210> SEQ ID NO 86
<211> LENGTH: 124
<212> TYPE: PRT
<213> ORGANISM: Homo sapiens

<400> SEQUENCE: 86

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Asn Ile Tyr Tyr Ala Asp Ser Val
        50                  55                  60

Lys Gly Arg Phe Thr Ile Ser Arg Asp Asn Ala Lys Asn Ser Leu Tyr
65                      70                  75                  80

Leu Gln Met Asn Ser Leu Arg Ala Glu Asp Thr Ala Val Tyr Tyr Cys
                85                  90                  95

Ala Arg Gly Ile Ala Val Ala Glu Asp Val Trp Gly Asn Gly Thr Thr
                100                 105                 110

Val Thr Val Ser Ser Glu Arg Lys Cys Cys Val Glu
        115                 120
```

<210> SEQ ID NO 87
<211> LENGTH: 124
<212> TYPE: PRT
<213> ORGANISM: Homo sapiens

<400> SEQUENCE: 87

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                      70                  75                  80

Leu Gln Met Asn Ser Leu Arg Ala Glu Asp Thr Ala Val Tyr Tyr Cys
```

```
                        85                  90                  95
Ala Arg Gly Val Ala Met Val Arg Asp Ser Trp Gly Gln Gly Thr Leu
                100                 105                 110

Val Asn Val Ser Ser Glu Arg Lys Cys Cys Val Glu
            115                 120

<210> SEQ ID NO 88
<211> LENGTH: 124
<212> TYPE: PRT
<213> ORGANISM: Homo sapiens

<400> SEQUENCE: 88

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Asp Ile Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Thr Arg Gly Val Ser Leu Val Arg Asp Tyr Trp Gly Gln Gly Thr Gln
                100                 105                 110

Val Thr Val Ser Ser Glu Leu Lys Thr Pro Leu Gly
            115                 120

<210> SEQ ID NO 89
<211> LENGTH: 124
<212> TYPE: PRT
<213> ORGANISM: Homo sapiens
<220> FEATURE:
<221> NAME/KEY: VARIANT
<222> LOCATION: 33, 40, 62, 101, 104, 107, 111, 118, 119, 120, 121, 122,
      123, 124
<223> OTHER INFORMATION: Xaa = Any Amino Acid

<400> SEQUENCE: 89

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Xaa Met Ser Trp Ile Arg Gln Xaa Pro Gly Lys Gly Leu Glu Trp Val
        35                  40                  45

Ser Tyr Ile Ser Ser Ser Gly Asp Ile Ile Tyr Tyr Ala Xaa Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Thr Arg Gly Val Xaa Leu Val Xaa Asp Tyr Xaa Gly Gln Gly Xaa Gln
                100                 105                 110

Val Thr Val Ser Ser Xaa Xaa Xaa Xaa Xaa Xaa
            115                 120

<210> SEQ ID NO 90
```

```
<211> LENGTH: 124
<212> TYPE: PRT
<213> ORGANISM: Homo sapiens

<400> SEQUENCE: 90

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Val Lys Leu Thr Glu Asp Asn Trp Gly Gln Gly Thr Leu
            100                 105                 110

Val Thr Val Ser Ser Glu Arg Lys Cys Cys Val Glu
        115                 120

<210> SEQ ID NO 91
<211> LENGTH: 124
<212> TYPE: PRT
<213> ORGANISM: Homo sapiens

<400> SEQUENCE: 91

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Val Lys Leu Thr Glu Asp Asp Trp Gly Gln Gly Thr Leu
            100                 105                 110

Val Thr Val Ser Ser Glu Arg Lys Cys Cys Val Glu
        115                 120

<210> SEQ ID NO 92
<211> LENGTH: 127
<212> TYPE: PRT
<213> ORGANISM: Homo sapiens

<400> SEQUENCE: 92

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Asp
            20                  25                  30

Tyr Met Ser Trp Ile Arg Gln Ala Pro Gly Lys Gly Leu Glu Trp Val
        35                  40                  45
```

```
Ser Tyr Ile Ser Ser Ser Gly Ser Ile Tyr Tyr Ala Asp Ser Val
    50              55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Phe Gly Glu Ser His Ser Phe Asp Tyr Trp Gly Gln
                100                 105                 110

Gly Thr Leu Val Thr Val Ser Ser Glu Arg Lys Cys Cys Val Glu
                115                 120                 125
```

<210> SEQ ID NO 93
<211> LENGTH: 127
<212> TYPE: PRT
<213> ORGANISM: Homo sapiens

<400> SEQUENCE: 93

```
Glu Val Gln Leu Val Glu Ser Gly Gly Leu Val Lys Pro Gly Gly
1               5                   10                  15

Ser Leu Arg Leu Ser Cys Ala Ala Ser Gly Phe Ile Phe Ser Asp Tyr
                20                  25                  30

Tyr Met Ser Trp Ile Arg Gln Ala Pro Gly Lys Gly Leu Glu Trp Ile
                35                  40                  45

Ser Tyr Ile Ser Ser Ser Gly Asp Ser Ile Tyr Tyr Ala Asp Ser Val
    50              55                  60

Lys Gly Arg Phe Thr Ile Ser Arg Asp Asp Ala Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Gly Trp Phe Gly Glu Ser His Tyr Ser Asp Phe Trp Gly Gln
                100                 105                 110

Gly Thr Leu Val Thr Val Ser Ser Glu Leu Lys Thr Pro Leu Gly
                115                 120                 125
```

<210> SEQ ID NO 94
<211> LENGTH: 122
<212> TYPE: PRT
<213> ORGANISM: Homo sapiens

<400> SEQUENCE: 94

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
                35                  40                  45

Ser Tyr Ile Ser Ser Ser Gly Ser Thr Ile Tyr Tyr Ala Asp Ser Val
    50              55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Pro Phe Asp Tyr Trp Gly Gln Gly Thr Leu Val Thr
                100                 105                 110

Val Ser Ser Glu Arg Lys Cys Cys Val Glu
                115                 120
```

<210> SEQ ID NO 95
<211> LENGTH: 131
<212> TYPE: PRT
<213> ORGANISM: Homo sapiens

<400> SEQUENCE: 95

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Arg Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ile Ala Val Ala Gly Thr Thr Arg His Tyr Ser Asp
            100                 105                 110

Tyr Trp Gly Gln Gly Thr Leu Val Thr Val Ser Ser Glu Arg Lys Cys
        115                 120                 125

Cys Val Glu
    130
```

<210> SEQ ID NO 96
<211> LENGTH: 124
<212> TYPE: PRT
<213> ORGANISM: Homo sapiens
<220> FEATURE:
<221> NAME/KEY: VARIANT
<222> LOCATION: 106
<223> OTHER INFORMATION: Xaa = Any Amino Acid

<400> SEQUENCE: 96

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Tyr Gly Trp Gly Xaa Trp Gly Gln Gly Thr Leu
            100                 105                 110

Val Thr Val Ser Ser Glu Arg Lys Cys Cys Val Glu
        115                 120
```

<210> SEQ ID NO 97
<211> LENGTH: 128
<212> TYPE: PRT
<213> ORGANISM: Homo sapiens

<400> SEQUENCE: 97

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Thr Pro Gly Lys Gly Leu Glu Trp Val
            35                  40                  45

Ser Tyr Ile Ser Asp Asp Asn Thr Ile Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Gly Tyr Phe Gly Glu Leu Pro Gly Phe Asp Tyr Trp Gly
            100                 105                 110

Gln Gly Thr Leu Val Thr Val Ser Glu Arg Lys Cys Cys Val Glu
            115                 120                 125

<210> SEQ ID NO 98
<211> LENGTH: 126
<212> TYPE: PRT
<213> ORGANISM: Homo sapiens

<400> SEQUENCE: 98

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Asp Tyr
            20                  25                  30

Tyr Met Ser Trp Leu Arg Gln Ala Pro Gly Lys Gly Leu Glu Trp Val
            35                  40                  45

Ser Tyr Ile Ser Ser Ser Gly Ser Asn Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Ala Gly Val Phe Asp Tyr Leu Gly Gln Gly Gly Arg Gly
            100                 105                 110

Thr Leu Val Thr Val Ser Ser Glu Arg Lys Cys Cys Val Glu
            115                 120                 125

<210> SEQ ID NO 99
<211> LENGTH: 126
<212> TYPE: PRT
<213> ORGANISM: Homo sapiens

<400> SEQUENCE: 99

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

-continued

Leu Gln Met Asn Ser Leu Arg Ala Glu Asp Thr Ala Val Tyr Tyr Cys
                 85                  90                  95

Ala Arg Asp Leu Val Gly Ala Thr Asp Phe Asp Tyr Trp Gly Gln Gly
            100                 105                 110

Thr Leu Val Thr Val Ser Ser Glu Arg Lys Cys Cys Val Glu
        115                 120                 125

<210> SEQ ID NO 100
<211> LENGTH: 123
<212> TYPE: PRT
<213> ORGANISM: Homo sapiens

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Phe Arg Gln Ala Pro Gly Lys Gly Leu Glu Trp Val
        35                  40                  45

Ser Lys Ile Thr Gly Ser Gly Gly Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Met Val Ala Ser His Tyr Trp Gly Gln Gly Thr Leu Val
            100                 105                 110

Thr Val Ser Ser Glu Arg Lys Cys Cys Val Glu
        115                 120

<210> SEQ ID NO 101
<211> LENGTH: 126
<212> TYPE: PRT
<213> ORGANISM: Homo sapiens

<400> SEQUENCE: 101

Glu Val Gln Leu Leu Glu Ser Gly Gly Gly Leu Val Gln Arg Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Gly Asp Arg Gly Tyr Phe Phe Asp Tyr Trp Gly Gln Gly
            100                 105                 110

Thr Leu Val Thr Val Ser Ser Glu Arg Lys Cys Cys Val Glu
        115                 120                 125

<210> SEQ ID NO 102
<211> LENGTH: 131
<212> TYPE: PRT
<213> ORGANISM: Homo sapiens -continued

```
<400> SEQUENCE: 102

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Thr Gly Ser Gly Ser Ser Thr Tyr Tyr Ala Asp Ser Val
        50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                85                  90                  95

Ala Lys Asp Arg Pro Tyr Gly Ser Gly Ser Tyr Lys Tyr Gly Met Asp
            100                 105                 110

Val Gly Gly Gln Gly Thr Thr Val Thr Val Ser Ser Glu Leu Lys Thr
            115                 120                 125

Pro Leu Gly
    130
```